United States Patent [19]
Reagen et al.

[11] Patent Number: 5,451,645
[45] Date of Patent: Sep. 19, 1995

[54] PROCESS FOR OLEFIN POLYMERIZATION

[75] Inventors: William K. Reagen, Idaho Falls, Id.; Ted M. Pettijohn, Bartlesville, Okla.; Jeffrey W. Freeman, Bartlesville, Okla.; Elizabeth A. Benham, Bartlesville, Okla.

[73] Assignee: Phillips Petroleum Company, Bartlesville, Okla.

[21] Appl. No.: 109,855

[22] Filed: Aug. 20, 1993

Related U.S. Application Data

[63] Continuation of Ser. No. 807,309, Dec. 13, 1991, abandoned, which is a continuation-in-part of Ser. No. 698,631, May 10, 1991, abandoned, which is a continuation-in-part of Ser. No. 393,354, Aug. 10, 1989, abandoned.

[51] Int. Cl.$^6$ .................................................. C08F 4/69
[52] U.S. Cl. ...................................... 526/97; 526/114; 526/115; 526/119; 526/121; 526/127; 526/133; 526/137; 526/141
[58] Field of Search .................. 526/97, 114, 115, 119, 526/121, 125, 129, 133, 141, 161, 127, 137

[56] References Cited

U.S. PATENT DOCUMENTS

| | | | |
|---|---|---|---|
| 2,935,495 | 11/1956 | Kennedy | 526/159 |
| 3,100,764 | 8/1963 | Jezl et al. | 526/141 |
| 3,231,550 | 1/1966 | Manyik et al. | 526/153 |
| 3,242,099 | 3/1966 | Manjik et al. | 252/429 |
| 3,300,458 | 1/1967 | Manyjik et al. | 526/169 |
| 3,347,840 | 10/1967 | Manyjik | 526/169 |
| 3,462,403 | 8/1969 | Pendleton | 526/119 |
| 3,534,006 | 10/1970 | Kamaishi et al. | 526/141 |
| 3,887,494 | 6/1975 | Dietz | 252/452 |
| 3,900,457 | 8/1975 | Witt | 526/106 |
| 3,985,718 | 10/1976 | Chabert et al. | 526/113 |
| 4,053,436 | 10/1977 | Hogan | 252/452 |
| 4,151,122 | 4/1979 | McDaniel et al. | 252/458 |
| 4,294,724 | 10/1981 | McDaniel | 252/451 |
| 4,324,691 | 4/1982 | Hartshorn et al. | 252/429 |
| 4,392,990 | 7/1983 | Witt | 252/458 |
| 4,405,501 | 9/1983 | Witt | 252/452 |
| 4,434,281 | 2/1984 | Swift | 526/119 |
| 4,451,573 | 5/1984 | Ikegami et al. | 502/113 |
| 4,668,838 | 5/1987 | Briggs | 585/513 |
| 4,716,206 | 12/1987 | Fujita et al. | 526/139 |
| 4,721,762 | 1/1988 | Commereuc | 526/75 |
| 4,861,846 | 8/1989 | Cann et al. | 526/75 |

FOREIGN PATENT DOCUMENTS 2253029 12/1973 France.

OTHER PUBLICATIONS

Morrison, R. T. and Boyd, R. N., *Organic Chemistry* (1980) pp. 729 and 730.
Solomons, T. W. G., *Organic Chemistry* (1976) p. 818.
Satterfield, C. N., *Heterogeneous Catalysis in Practice* pp. 68–77.
Le Page, J. F. et al., *Applied Heterogeneous Catalysis* (1978) pp. 90–96.
Leach, B. E. (ed), *Applied Industrial Catalysis* (1984) pp. 13–14 and 25–37.
Hegedus, L. L. (Ed.), *Catalyst Design Progress and Perspectives* (1985) pp. 112–117.
Zeitschrift fur Naturforschung, Pyrrolylchromium Compounds, 21 b, p. 1239 (D. Tille, 1966).
Z. Anorg. Alleg. Chem., Organometal Compounds of Nitrogen Systems, 384, pp. 136–146 (D. Tille, 1971).
J. Chem. Soc., Chem. Commun., Selective Trimerization of Ethylene to Hex–1–ene, pp. 674–675 (J. Briggs, 1989).

*Primary Examiner*—Romulo H. Delmendo
*Attorney, Agent, or Firm*—Lynda S. Jolly

[57] ABSTRACT

Novel chromium-containing compounds are prepared by forming a mixture of a chromium salt, a metal amide, and an ether. These novel chromium-containing, or chromium pyrrolide, compounds, with a metal alkyl and an unsaturated hydrocarbon, can be used as a cocatalyst system in the presence of an olefin polymerization catalyst system to produce a comonomer in-situ. The resultant polymer, although produced from predominately one monomer, has characteristics of a copolymer.

29 Claims, 9 Drawing Sheets

PROCESS FOR OLEFIN POLYMERIZATION

This application is a Continuation of application Ser. No. 07/807,309, now abandoned, which is a continuation-in-part of application Ser. No. 07/698,631, filed May 10, 1991, now abandoned, the entirety of which is herein incorporated by reference; which is a continuation-in-part of Ser. No. 07/393,354, filed Aug. 10, 1989, now abandoned, the entirety of which is herein incorporated by reference.

BACKGROUND OF THE INVENTION

This invention relates to the polymerization of olefins, such as ethylene, in the presence of any polymerization catalyst and one or more novel chromium cocatalyst systems.

It is well known that olefins, such as ethylene, can be polymerized with catalyst systems employing supported, chromium catalyst or magnesium/titanium catalysts. Initially such catalysts were used primarily to form olefin homopolymers. It soon developed, however, that many applications required polymers which were more impact resistant than olefin homopolymers. Consequently, in order to produce polymer having short chain branching like the more flexible free radical polymerized olefin polymers, comonomers such as propylene, butene, hexene or other higher olefins were copolymerized with the olefin monomer to provide resins tailored to specific end uses. The copolymers, however, are more expensive to produce since inventories of different monomers must be kept and also the comonomers are generally more expensive than the usual short-chain monomers, such as ethylene or propylene. Linear olefin polymers, such as polyethylene, with short chain branching can be formed from a pure ethylene feed using the old free radical high pressure process, but the conditions necessary to do this make the product too expensive to be commercially competitive.

Additional control over the polymerization process and the resultant polymer is also desired. A process to consistently reduce the density of linear olefin polymers and to more efficiently produce and incorporate comonomers into the linear olefin polymer is economically advantageous. A shift in the polymer branch distribution, wherein the branch length is decreased and the amount of branching is increased, is also economically desirable.

SUMMARY OF THE INVENTION

Accordingly it is an object of this invention to provide a low cost route to linear olefin polymers having toughness imparted by short chain branching.

It is a further object of this invention to provide a process by which olefin polymers having the properties associated with copolymers can be obtained from a pure, single olefin feed.

It is yet a further object of this invention to provide an improved polymerization process.

It is a further object of this invention to provide a novel polymerization process to control polymer density.

It is yet a further object of this invention to provide a novel polymerization process to improve comonomer production and incorporation into olefin polymers.

It is a further object of this invention to provide a novel polymerization process to shift olefin distribution.

It is a further object of this invention to provide a novel polymerization process to control polymer short chain branching.

In accordance with this invention, an essentially pure, single olefin feed is contacted under polymerization conditions with a polymerization catalyst and an olefin trimerization and/or oligomerization cocatalyst system comprising the reaction product of a chromium salt, a metal amide, and an ether; an activating compound selected from the group consisting of metal alkyls, Lewis acids, and mixtures thereof; and an unsaturated hydrocarbon. In accordance with a second embodiment of this invention, an essentially pure, single olefin feed is contacted under polymerization conditions with a polymerization catalyst and an olefin trimerization and/or oligomerization cocatalyst system comprising the reaction product of a chromium source, a pyrrole-containing compound, a metal alkyl, and an unsaturated hydrocarbon. Additionally, hydrogen can be introduced into the polymerization reactor in an amount sufficient to accelerate the trimerization, oligomerization and/or polymerization processes.

DETAILED DESCRIPTION OF THE INVENTION

Polymerization Catalyst

Figure 1:
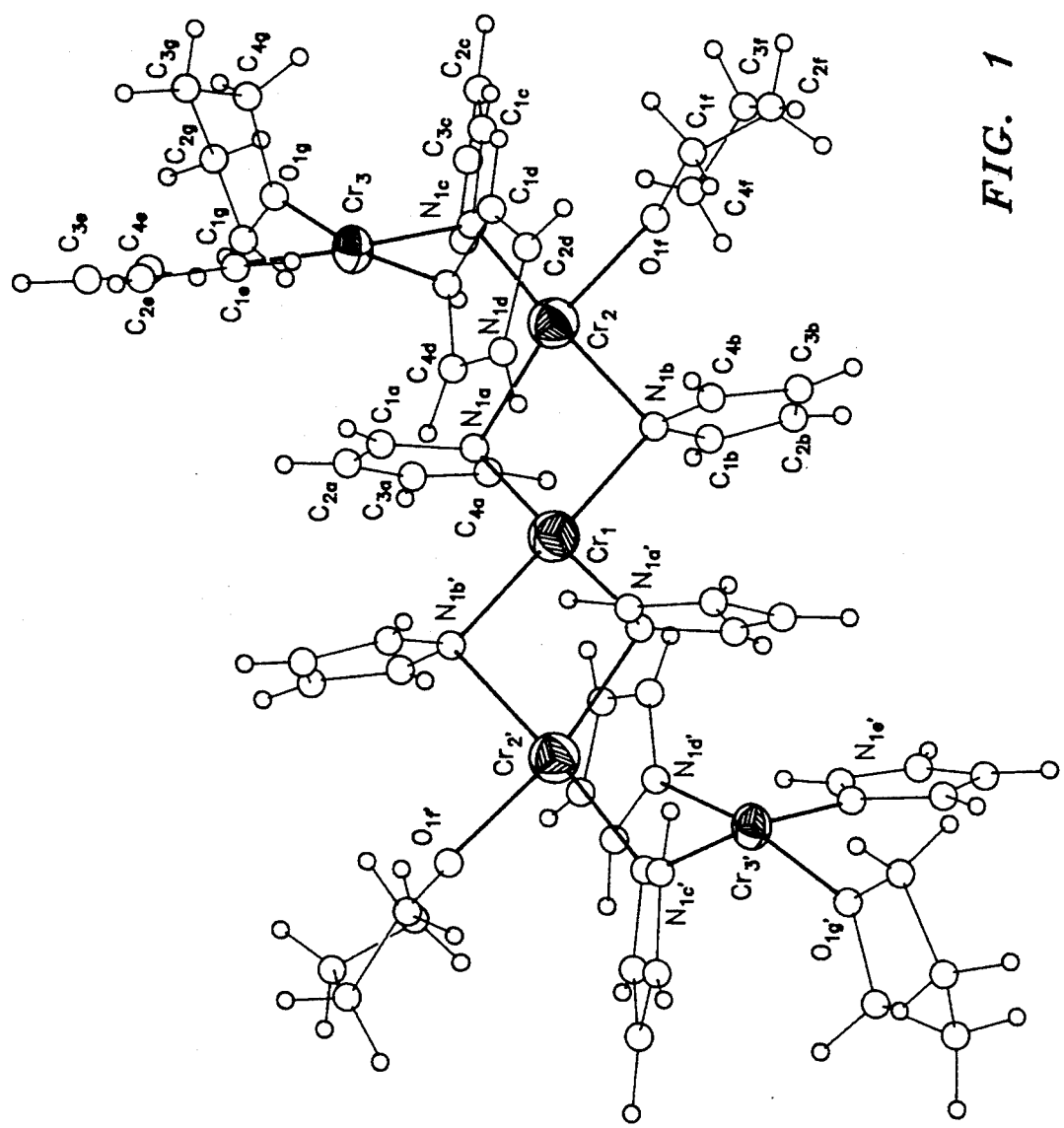
FIG. 1 is a computer generated ball and stick projection, with the exception of the chromium atoms which are represented as thermal ellipsoids, or a simplified structural representation or formula, of a molecule of Product I, $Cr_5(NC_4H_4)_{10}(OC_4H_8)_4$, as determined by single crystal x-ray crystallography.

The novel trimerization and/or oligomerization cocatalyst systems, including the inventive chromium compounds, can be used either supported or unsupported as a cocatalyst with any other olefin polymerization catalyst. Generally, polymerization catalysts systems are considered either chromium catalysts (also known as "Phillips Catalysts") or titanium, zirconium and/or vanadium-containing catalysts.

Any chromium catalyst system known in the art can be used. Commercially available chromium catalyst systems typically comprise chromium, at least a portion of which is in the hexavalent state, supported on an inorganic oxide; optionally, the polymerization catalyst system can further comprise a metal alkyl co-catalyst. Exemplary chromium catalyst systems include, but are not limited to those disclosed in U.S. Pat. Nos. 3,87,494; 3,900,457; 4,053,436; 4,151,122; 4,294,724; 4,392,990; and 4,405,501, herein incorporated by reference.

Any titanium, zirconium and/or vanadium-containing catalyst system known in the art can also be used. Commercially available titanium, zirconium and/or vanadium catalyst systems typically comprise complexes of transition metal halides with organometallic compounds. Exemplary magnesium/titanium catalysts include, but are not limited to, those disclosed in U.S. Pat. Nos. 4,394,291; 4,326,988; and 4,347,158, herein incorporated by reference.

The amount of novel trimerization and/or oligomerization cocatalyst systems, including the inventive chromium compounds used as a cocatalyst can be any amount sufficient to generate a comonomer that can be incorporated into the polymer product.

Chromium Compounds

The inventive chromium compounds, which can be used preferably for olefin trimerization and, optionally, olefin oligomerization and/or polymerization, can be produced by forming a reaction mixture comprising a chromium salt, a metal amide, and any electron pair donor solvent, such as, for example, an ether. As used in this disclosure, the inventive chromium compounds are referred to by a variety of interchangeable names, such as inventive or novel chromium compound(s), chromium complex(es), chromium pyrrole complex(es) and/or chromium pyrrolide(s).

The chromium salt can be one or more organic or inorganic chromium salts, wherein the chromium oxidation state is from 0 to 6. As used in this disclosure, chromium metal is included in this definition of a chromium salt. Generally, the chromium salt will have a formula of $CrX_n$, wherein X can be the same or different and can be any organic or inorganic radical, and n is an integer from 1 to 6. Exemplary organic radicals can have from about 1 to about 20 carbon atoms per radical, and are selected from the group consisting of alkyl, alkoxy, ester, ketone, and/or amido radicals. The organic radicals can be straight-chained or branched, cyclic or acyclic, aromatic or aliphatic, and can be made of mixed aliphatic, aromatic, and/or cycloaliphatic groups. Exemplary inorganic radicals include, but are not limited to halides, sulfates, and/or oxides.

Preferably, the chromium salt is a halide, such as, for example chromous fluoride, chromic fluoride, chromous chloride, chromic chloride, chromous bromide, chromic bromide, chromous iodide, chromic iodide, and mixtures thereof. Most preferably, the chromium salt is a chloride, such as, for example chromous chloride and/or chromic chloride, due to simple separation of the reaction by-products such as, for example, sodium chloride, as well as relatively low cost.

The metal amide can be any metal amide that will react with a chromium salt to form a chromium-amido complex. Broadly, the metal amide can be any heteroleptic or homoleptic metal complex or salt, wherein the amide radical can be any nitrogen-containing organic radical. The metal amide can be either affirmatively added to the reaction, or generated in-situ. Generally, the metal amide will have from about 1 to about 20 carbon atoms. Exemplary metal amides include, but are not limited to, primary and/or secondary amines, any alkali metal (Group IA, and including hydrogen, of the Periodic Table) amide and/or any alkaline earth metal (Group IIA of the Periodic Table) amide. The hydrocarbyl portion of the salt of the metal amide is selected from the group consisting of straight chain or branched, cyclic or acyclic, aromatic or aliphatic, and mixtures of two or more thereof. Preferably, the metal amide is selected from a Group IA metal, and including hydrogen, or Group IIA metal amide, due to ease of reaction with chromium halides.

Exemplary preferred metal amides include, but are not limited to, lithium dimethylamide, lithium diethylamide, lithium diisopropylamide, lithium dicyclohexylamide, sodium bis(trimethylsilyl)amide, sodium indolide, sodium pyrrolide, and mixtures of two or more thereof. Most preferably, the metal amide is a pyrrolide. As used in this disclosure, a pyrrolide is defined as a compound comprising a 5-membered, nitrogen-containing heterocycle, such as, for example, pyrrole, derivatives of pyrrole, and mixtures thereof. Exemplary pyrrolides are selected from the group consisting of hydrogen pyrrolide (pyrrole), lithium pyrrolide, sodium pyrrolide, potassium pyrrolide, cesium pyrrolide, and/or the salts of substituted pyrrolides, because of high reactivity and activity with the other reactants. Examples of salts of substituted pyrrolides include, but are not limited to sodium 2,5-dimethyl pyrrolide and/or 3,4-dimethyl pyrrolide. When the metal amide is a pyrrolide ligand, the resultant chromium compound is a chromium pyrrolide.

The electron pair donor solvent can be any electron pair donor solvent to effect a reaction between the chromium salt and the metal amide. While not wishing to be bound by theory, it is believed that the electron pair donor solvent can be a reaction solvent, as well as a possible reactant. Exemplary electron pair donor solvents include, but are not limited to, nitrogen-containing compounds; oxygen-containing compounds, such as, for example, ethers; phosphorous-containing compounds; and/or sulfur-containing compounds.

Exemplary nitrogen-containing compounds include, but are not limited to nitriles, such as, for example, acetonitrile; amines, such as, for example, pyridine, and/or derivatives of pyridine; and/or amides. Additional exemplary nitrogen-containing compounds include, but are not limited to, nitromethane, dimethylpyridine, dimethylformamide, N-methylformamide, aniline, nitrobenzene, tetramethyldiaminomethane, hexamethyldisilazane, and/or pyrrolidone.

Exemplary oxygen-containing compounds include, but are not limited to, acetone, ethyl acetate, methyl acetate, methanol, ethanol, ethyl methyl ketone, acetaldehyde, furan, and/or hexamethyldisiloxane.

Exemplary phosphorous-containing compounds include, but are not limited to, hexamethylphosphoramide, hexamethylphosphoroustriamide, triethylphosphite, tributylphosphine oxide, and/or triethylphosphine.

Exemplary sulfur-containing compounds include, but are not limited to, carbon disulfide, dimethylsulfoxide, tetramethylene sulfone, thiophene, and/or dimethylsulfide or mixtures thereof.

The ether in the reaction mixture can be one or more ether compounds to affect a reaction between the chromium salt and the metal amide. While not wishing to be bound by theory, it is believed that the ether can be a reaction solvent, as well as a possible reactant. The ether can be any aliphatic and/or aromatic compound containing an R-O-R functionality, wherein the R groups can be the same or different, but preferably is not hydrogen. Preferred ethers are aliphatic ethers, for safety reasons in that aromatic ethers are human toxins. Furthermore, the preferred ethers are those which facilitate a reaction between a chromium halide and a Group IA or Group IIA metal pyrrolide, and also can be easily removed from the reaction mixture. Exemplary compounds include, but are not limited to, tetrahydrofuran, dioxane, diethylether, dimethoxyethane (glyme), diglyme, triglyme, and mixtures of two or more thereof. Most preferably, the ether is selected from the group consisting of tetrahydrofuran, derivatives of tetrahydrofuran, dimethoxyethane, derivatives of dimethoxyethane, and mixtures thereof, for the reasons given above, as well as the reason that the preferred salt of an amine is soluble in these ethers.

The amount of each reactant used to prepare one or more of the novel chromium compounds can vary, based on the desired chromium compound product. Any amount of each reactant can be used to produce the novel chromium compounds, depending on the desired product. Different reaction stoichiometries can produce different chromium compounds. For example, the reaction of about one mole of chromium (II) with about two moles of sodium pyrrolide can produce different products than reacting about one mole of chromium (II) with an excess of sodium pyrrolide. Furthermore, as stated earlier, selection of different, although similar reactants, can produce different products. For example, using either tetrahydrofuran or dimethoxyethane can result in a different reaction product.

The three reactants can be combined in any manner under conditions suitable to form a solution comprising one or more of the inventive chromium compounds. The reaction preferably occurs in the absence of oxygen and moisture and therefore under an inert atmosphere, such as, for example nitrogen and/or argon. The reaction pressure can be any pressure sufficient to maintain the reactants in a liquid state. Generally, pressure within the range of from about atmospheric pressure to about three atmospheres are acceptable. For ease of operation atmospheric pressure is generally employed.

The reaction temperature can be any temperature which maintains the ether in a liquid form. In order to effectuate a more efficient reaction, temperatures near the boiling point of the ether are preferred. Most preferably, the reaction temperature is at the boiling point of the ether and the reaction mixture is refluxed for a period of time.

The reaction time can be any amount of time necessary for the reaction to occur. Depending on the reactants, as well as the reaction temperature and pressure, reaction time can vary from about 1 minute to about 1 week. Usually, reaction time ranges from about 3 hours to about 5 days. Under optimum conditions, the reaction time can be within the range of from about 3 to about 48 hours.

After the reaction is complete, a solid reaction product can be recovered by any method known in the art. Preferably, though not required, upon completion of the reaction, the reaction mixture first is filtered to remove any particulate reaction by-products such as, for example, salts, like sodium chloride, prior to any other treatment. Although removal of any reaction by-products is not necessary, such removal preferably is done in order to expedite later purification of the chromium product. After filtering, one exemplary method to recover a solid reaction product is to remove the excess ether from the reaction mixture. The excess electron pair donor solvent, such as, for example an ether, can be removed according to any method known in the art. Exemplary electron pair donor solvent, such as, for example an ether, removal methods include, but are not limited to, slow evaporation, under vacuum and/or a nitrogen purge.

Other electron pair donor solvents, such as, for example, an ether, removal procedures can be used either alone or in combination. For example, the reaction mixture can be filtered and then vacuum dried. Preferably, the reaction mixture is heated slowly and maintained at a temperature within the range of about 10° to about 300° C., preferably about 25° to about 200° C., under a vacuum, for safety, to remove the excess electron pair donor solvent, such as, for example an ether. The resultant solid reaction product is one or more of the inventive chromium compounds.

Alternatively, the reaction mixture can be filtered to remove any solid reaction by-product solids and the filtered reaction mixture can be contacted with a non-polar organic solvent. Addition of a non-polar organic solvent causes one or more of the inventive chromium compounds to form a solid precipitate. Exemplary non-polar organic solvents include, but are not limited to, pentane, hexane, cyclohexane, heptane, and mixtures thereof. Most preferably pentane is added to the filtered reaction mixture because of the availability and ease of use.

The precipitated inventive chromium compounds can be recovered by any method known in the art. The simplest procedure to remove the inventive precipitated chromium compounds is by filtration.

The reaction mixture and the resultant solid reaction products, as stated earlier, are kept in an oxygen-free atmosphere at all times. Preferably, due to availability and ease of use, an inert atmosphere such as, for example, nitrogen, is the ambient.

Numerous chromium compounds can be prepared in accordance to the invention, by varying the reactants and/or the quantity of each reactant employed. The recovered, novel chromium compound or compounds can be used for olefin trimerization and/or polymerization without further purification.

Optionally, the chromium compound can be purified in accordance with any method known in the art. For example, one of the simplest purification procedures is to wash the recovered solid with a non-polar organic solvent such as, for example, toluene. Preferably, a non-polar aliphatic organic solvent is used for best results. Exemplary wash solvents include, but are not limited to, pentane, hexane, cyclohexane, heptane, and mixtures thereof. Most preferably, pentane is the wash solvent.

Novel metal pyrrolides can also be prepared from salts of other metals. Exemplary metals include, but are not limited to, nickel, cobalt, iron, molybdenum, and copper. As with the previously described chromium salt, the metal oxidation state of the metal can be any oxidation state, including the elemental, or metallic, state. These novel metal pyrrolides can be prepared in a manner similar to the previously described chromium pyrrolides.

Catalyst Systems

Catalyst systems prepared in accordance with this invention can be used preferably for olefin trimerization and, optionally, olefin oligomerization and/or polymerization. Catalyst systems comprise a metal source, a pyrrole-containing compound, a metal alkyl, also called an activating compound, and an unsaturated hydrocarbon compound. Exemplary metal sources are selected from the group consisting of chromium, nickel, cobalt, iron, molybdenum, and copper. While this disclosure deals primarily with chromium salts and chromium sources, other metal sources, which can result in less active catalyst systems, can be substituted for the chromium salt or chromium source. Preferably, catalyst systems comprise a chromium source, a pyrrole-containing compound, a metal alkyl, also called an activating compound, and an unsaturated hydrocarbon compound for best resultant catalyst system activity and product selectivity. Optionally, for ease of use, a chromium pyrrolide can provide both the chromium source and the pyrrole-containing compound. As used in this disclosure, when a chromium pyrrolide is used to form a catalyst system, a chromium pyrrolide is considered to provide both the chromium source and the pyrrole-containing compound. Catalyst systems can further comprise a catalyst support.

In accordance with one embodiment of the invention, the inventive chromium compounds can be combined in a reaction mixture with a metal alkyl and an unsaturated hydrocarbon compound and can be used, either as a supported and/or unsupported catalyst system, for olefin trimerization, oligomerization and/or polymerization. The novel chromium compounds provide a chromium source, as well as a pyrrole-containing compound, for catalyst systems prepared in accordance with this first embodiment.

A supported chromium catalyst system can be prepared with any support useful to support a chromium catalyst. Exemplary catalyst supports include, but are not limited to, zeolites inorganic oxides, either alone or in combination, phosphated inorganic oxides, and mixtures thereof. Particularly preferred are supports selected from the group consisting of silica, silica-alumina, alumina, fluorided alumina, silated alumina, thoria, aluminophosphate, aluminum phosphate, phosphated silica, phosphated alumina, silica-titania, coprecipitated silica/titania, fluorided/silated alumina, and mixtures, thereof, being presently preferred, as well as any one or more of these supports which can contain chromium. The presently most preferred catalyst support, because of the greatest trimerization activity, is aluminophosphate, as disclosed in U.S. Pat. No. 4,364,855 (1982), herein incorporated by reference.

Supported chromium catalyst systems can be prepared according to any method known in the art. For example, the inventive chromium compound reaction mixture, which preferably has been filtered to remove any particulate reaction by-products and contains one or more of the novel chromium pyrrolide compounds, is combined and thoroughly contacted with a catalyst support. Excess electron pair donor solvent, such as, for example an ether, does not have to be removed prior to contacting the catalyst support. However, a solid chromium pyrrolide compound can be re-dissolved in an electron pair donor solvent, such as, for example an ether, if desired. The chromium pyrrolide/electron pair donor, such as, for example, an ether solution is usually a blue or blue/green color, although other colors can be observed.

The catalyst support usually is insoluble in the electron pair donor solvent, such as, for example, an ether/chromium pyrrolide complex solution. Any excess of the chromium pyrrolide in relation to the catalyst support is sufficient. However, usually, less than about 5 grams of chromium pyrrolide compound per gram of catalyst support is sufficient. Preferably, about 0.001 to about 1 gram of chromium pyrrolide compound per gram of support, and most preferably, 0.01 to 0.5 gram of chromium pyrrolide compound per gram of support is used for best support loading and most efficient use of the reagents. The amount of chromium pyrrolide compound per gram of support can be expressed in different, yet equivalent terms, such as, for example, moles of chromium per gram of support. Usually, less than about $8.6 \times 10^{-3}$ moles of chromium per gram of support is sufficient. Preferably, about $1.7 \times 10^{-6}$ to about $1.7 \times 10^{-5}$ to $8.6 \times 10^{-4}$ moles of chromium per gram of support are used, for reasons given above.

This mixture can be contacted and mixed at any time, temperature, and pressure to thoroughly contact the chromium pyrrolide compound and support. For ease of use, ambient temperatures and pressures are preferred. Mixing times can be up to about 24 hours, preferably, less than about 10 hours, and most preferably, from 1 second to 8 hours. Longer times usually provide no additional benefit and shorter times can be insufficient for thorough contacting.

After the support is added and thoroughly combined with the chromium pyrrolide, it can be collected by filtration, vacuum dried, then an activating compound, usually as a solution of one or more Lewis acids and/or metal alkyls, preferably in an unsaturated hydrocarbon compound solvent, is added to the support/chromium pyrrolide mixture. An active, supported catalyst system then can be collected by filtration. As used in this disclosure, a Lewis acid is defined as any compound that is an electron acceptor. Preferably, the activating compound is a compound that can be considered both a Lewis acid and a metal alkyl. The activating compound can have any number of carbon atoms. However, due to commercial availability and ease of use, the activating compound will usually comprise less than about 70 carbon atoms per metal alkyl molecule and preferably less than about 20 carbon atoms per molecule. Preferred activating compounds which are both a metal alkyl and a Lewis acid include, but are not limited to, alkylaluminum compounds, alkylboron compounds, alkylmagnesium, alkylzinc, and/or alkyllithium compounds. Exemplary metal alkyls include, but are not limited to, n-butyllithium, s-butyllithium, t-butyllithium, diethylmagnesium, dibutylmagnesium, diethylzinc, triethylaluminum, trimethylaluminum, triisobutylaluminum, and mixtures thereof. Most preferably, activating compounds are selected from the group consisting of non-hydrolyzed, i.e., not pre-contacted with water, alkylaluminum compounds, derivatives of alkylaluminum compounds, halogenated alkylaluminum compounds, and mixtures thereof for improved product selectivity, as well as improved catalyst system reactivity, activity, and/or productivity. Exemplary compounds include, but are not limited to, triethylaluminum, tripropylaluminum, tributylaluminum, diethylaluminum chloride, diethylaluminum bromide, diethylaluminum ethoxide, ethylaluminum sesquichloride, and mixtures thereof for best catalyst system activity and product selectivity. The most preferred alkylaluminum compound is triethylaluminum, for best results in catalyst system activity and product selectivity.

When a trimerization catalyst system is the desired product, the activating compound must be a non-hydrolyzed alkylaluminum compound, expressed by the general formulae $AlR_3$, $AlR_2X$, $AlRX_2$, $AlR_2OR$, $AlRXOR$, and/or $Al_2R_3X_3$, wherein R is an alkyl group and X is a halogen atom. Exemplary compounds include, but are not limited to, triethylaluminum, tripropylaluminum, tributylaluminum, diethylaluminumchloride, diethylaluminumbromide, diethylaluminumethoxide, diethylaluminum phenoxide, ethylaluminumethoxychloride, and/or ethylaluminum sesquichloride. Preferably, the activating compound for a trimerization catalyst system is a trialkylaluminum compound, $AlR_3$, for reasons given above. The most preferred trialkylaluminum compound is triethylaluminum, for reasons given above.

Any amount of activating compound, such as a metal alkyl and/or a Lewis acid, is sufficient to activate and/or react with the chromium pyrrolide catalyst. Usually about 200 grams of activating compound, i.e., metal alkyl and/or a Lewis acid, per gram of chromium can be used. Preferably, about 1 to about 100 grams of activating compound, such as a metal alkyl and/or a Lewis acid, per gram of chromium pyrrolide, and most preferably about 5 to about 30 grams of activating compound, such as a metal alkyl and/or a Lewis acid, per gram of chromium pyrrolide are used, for best catalyst activity. However, the amount of activating compound, such as a metal alkyl and/or a Lewis acid employed can vary with the catalyst support used. For example, if the support is silica and/or alumina, too much activating compound, such as a metal alkyl and/or a Lewis acid can decrease catalyst activity. However, a similar amount of activating compound, such as a metal alkyl and/or a Lewis acid, used with an aluminophosphate support does not always significantly decrease catalyst activity.

The unsaturated hydrocarbon compound, also referred to in this application as a solvent compound, can be any combination of one or more aromatic or aliphatic unsaturated hydrocarbon compounds. While not wishing to be bound by theory, it is believed that an unsaturated hydrocarbon compound acts as more than a solvent, and can be a reactant and/or a stabilizing component during and/or subsequent to formation of an inventive catalyst system. Exemplary unsaturated hydrocarbon compounds, such as, for example, a solvent, can be any unsaturated hydrocarbon compound that can dissolve the activating compound, i.e., wherein the activating compound can be a Lewis acid and/or metal alkyl. Preferred unsaturated hydrocarbon compounds include, but are not limited to, unsaturated hydrocarbons comprising less than about 70 carbon atoms per molecule, aromatic compounds having from about 6 to about 50 carbon atoms per molecule and preferably unsaturated hydrocarbons comprising less than about 20 carbon atoms per molecule, due to commercial availability and ease of use. Specific exemplary unsaturated aliphatic compounds include, but are not limited to, ethylene, 1-hexene, 1,3-butadiene, and mixtures thereof. The most preferred unsaturated aliphatic hydrocarbon compound is ethylene because of elimination of catalyst system preparation steps and ethylene can be a trimerization and/or oligomerization reactant. Specific exemplary unsaturated aromatic hydrocarbon compounds include, but are not limited to, toluene, benzene, xylene, mesitylene, hexamethylbenzene, and mixtures thereof. Most preferably, the unsaturated aromatic hydrocarbon compound solvent is toluene, for ease of removal and minimal interference with the resultant catalyst system, as well as increased trimerization and/or oligomerization activity.

The unsaturated hydrocarbon compound can be present either during the initial contacting of a chromium pyrrolide and activating compound, i.e., prior to introduction into a trimerization, oligomerization and/or polymerization reactor, or the unsaturated hydrocarbon compound can be introduced directly into the reactor. Furthermore, one or more of the olefin reactants can be considered the unsaturated hydrocarbon. Preferably, the unsaturated hydrocarbon is present during the initial contacting of a chromium pyrrolide and activating compound in order to stabilize the resultant catalyst system. In the absence of an unsaturated hydrocarbon, the resultant catalyst system can deactivate and lose activity over a period of time.

While any amount of unsaturated hydrocarbon compound can be used, too much or too little can adversely affect catalyst system activity. Therefore, preferably, the resultant catalyst system is stripped of any excess unsaturated aromatic hydrocarbon. Stripping of excess unsaturated aromatic hydrocarbon can be accomplished by any method known in the art, such as, for example, solvent removal methods. Exemplary removal methods include, but are not limited to, filtration, vacuum drying, drying under an inert atmosphere, and combinations thereof. While not wishing to be bound by theory, it is believed that the remaining unsaturated hydrocarbon can stabilize the resultant catalyst system. If no unsaturated hydrocarbon is present, it is believed that the catalyst system can lose activity.

As disclosed earlier, the mixture of supported chromium pyrrolide, activating compound, such as a metal alkyl and/or a Lewis acid, and unsaturated hydrocarbon are mixed and/or contacted under a dry, inert atmosphere at all times. Any pressure can be used during the contacting; for ease of use, atmospheric pressure is preferred. Any temperature can be used during the contacting; for ease of use, room temperature, or ambient temperature, is preferred. Some care should be taken during the mixing, so as not to destroy the physical integrity of the chromium pyrrolide, catalyst support, and resultant supported catalyst. The four-component mixture can be contacted for any amount of time sufficient to prepare and activate a chromium catalyst system. Usually, times in the range of about one minute to about one week are sufficient. Preferably, times in the range of about 30 minutes to about 24 hours are used, and most preferably times in the range of about one hour to about 12 hours are used. Too short of mixing times can result in incomplete contacting and too long of mixing times will not provide any additional catalytic benefit. An active, supported catalyst system then can be collected by filtration.

An alternative, and presently preferred, method to produce a supported catalyst system is to combine one or more solid, inventive chromium pyrrolide compounds with an unsaturated hydrocarbon solvent, as disclosed earlier, such as, for example, toluene and/or ethylene, and an activating compound, as disclosed earlier, such as a metal alkyl and/or a Lewis acid, such as, for example, triethylaluminum. This mixture can be stirred for any time sufficient to dissolve the chromium pyrrolide compound, at any pressure or temperature. Usually, times of about one minute to about one week, preferably about one hour to about 24 hours, and most preferably within the range of about three hours to about 12 hours are used. For ease of operation, ambient temperatures and pressures are used. Usually, a brown solution will result.

After the solution is sufficiently mixed, a support is added to the solution and stirred to thoroughly contact the solution and support. The quantity of support added is any amount sufficient to support the chromium pyrrolide compound. Generally, the amount of support necessary is the same as that disclosed in the previous exemplary process. Any suitable pressure and temperature can be used, although ambient temperature and pressure are preferred for ease of use. Usually, the mixing and/or contacting time is within the range of about 30 minutes to about one week, preferably from about 3 hours to about 48 hours. Most preferably, the mixing and/or contacting time is within the range of about 5 hours to about 24 hours, to maximize efficiency and result in a thoroughly contacted support. Alternatively, the support can be added concurrently with an inventive chromium compound, an aluminum alkyl, and an unsaturated hydrocarbon.

The solution then can be filtered to recover a solid catalytic product. The catalytic product, as with the reactants and reactions, is preferably kept under a dry, inert atmosphere to maintain chemical stability.

If an inventive chromium compound, such as, for example, a chromium pyrrolide, is recovered, i.e., isolated, it can be used as an unsupported trimerization, oligomerization and/or polymerization catalyst. Olefins can be trimerized, oligomerized and/or polymerized in a presence of one or more of these inventive chromium compounds, an unsaturated hydrocarbon and an activating compound, such as, for example a Lewis acid and/or a metal alkyl.

In accordance with a second embodiment of the invention, a catalyst system can be prepared by forming a reaction mixture comprising a chromium source, a pyrrole-containing compound, a metal alkyl and an unsaturated hydrocarbon compound. These catalyst systems can further comprise a catalyst support. A chromium pyrrolide can be used as both a chromium source and a pyrrole-containing compound.

The chromium source, similar to the earlier discussed chromium salt, can be one or more organic or inorganic chromium compounds, wherein the chromium oxidation state is from 0 to 6. As used in this disclosure, chromium metal is included in this definition of a chromium salt. Generally, the chromium source will have a formula of $CrX_n$, wherein X can be the same or different and can be any organic or inorganic radical, and n is an integer from 1 to 6. Exemplary organic radicals can have from about 1 to about 20 carbon atoms per radical, and are selected from the group consisting of alkyl, alkoxy, ester, ketone, and/or amido radicals. The organic radicals can be straight-chained or branched, cyclic or acyclic, aromatic or aliphatic, can can be made of mixed aliphatic, aromatic, and/or cycloaliphatic groups. Exemplary inorganic radicals include, but are not limited to halides, sulfates, and/or oxides.

Preferably, the chromium source is a chromium(II)- and/or chromium(III)-containing compound which can yield a catalyst system with improved trimerization activity. Most preferably, the chromium source is a chromium(III) compound because of ease of use, availability, and enhanced catalyst system activity. Exemplary chromium(III) compounds include, but are not limited to, chromium carboxylates, chromium naphthenates, chromium halides, chromium pyrrolides, and/or chromium dionates. Specific exemplary chromium(III) compounds include, but are not limited to, chromium (III)2,2,6,6-tetramethylheptanedionate [Cr(TMHD)$_3$], chromium(III)2-ethylhexanoate [Cr(EH)$_3$], chromium(III)naphthenate [Cr(Np)$_3$], chromium(III) chloride, chromium (III) tris(2-ethylhexanoate), chromic bromide, chromic chloride, chromic fluoride, chromium (III) oxy-2-ethylhexanoate, chromium (III) dichloroethylhexanoate, chromium (III) acetylacetonate, chromium (III) acetate, chromium (III) butyrate, chromium (III) neopentanoate, chromium (III) laurate, chromium (III) stearate, chromium (III) pyrrolides, and/or chromium (III) oxalate.

Specific exemplary chromium (II) compounds include, but are not limited to, chromous fluoride, chromous chloride, chromous bromide, chromous iodide, chromium (II) bis(2-ethylhexanoate), chromium (II) acetate, chromium (II) butyrate, chromium (II) neopentanoate, chromium (II) laurate, chromium (II) stearate, chromium (II) pyrrolides, and/or chromium (II) oxalate.

The pyrrole-containing compound can be any pyrrole-containing compound that will react with a chromium salt to form a chromium pyrrolide complex. As used in this disclosure, the term "pyrrole-containing compound" refers to hydrogen pyrrolide, i.e., pyrrole, ($C_4H_5N$), derivatives of hydrogen pyrrolide, as well as metal pyrrolide complexes. A "pyrrolide", as discussed earlier is defined as a compound comprising a 5-membered, nitrogen-containing heterocycle, such as, for example, pyrrole, derivatives of pyrrole, and mixtures thereof. Broadly, the pyrrole-containing compound can be pyrrole and/or any heteroleptic or homoleptic metal complex or salt, containing a pyrrolide radical, or ligand. The pyrrole-containing compound can be either affirmatively added to the reaction, or generated in-situ. Generally, the pyrrole-containing compound will have from about 1 to about 20 carbon atoms per molecule. Exemplary pyrrolides are selected from the group consisting of hydrogen pyrrolide (pyrrole), derivatives of pyrrole, substituted pyrrolides, lithium pyrrolide, sodium pyrrolide, potassium pyrrolide, cesium pyrrolide, and/or the salts of substituted pyrrolides, because of high reactivity and activity with the other reactants. Examples of substituted pyrrolides include, but are not limited to pyrrole-2-carboxylic acid, 2-acetylpyrrole, pyrrole-2-carboxaldehyde, tetrahydroindole, 2,5-dimethyl- pyrrole, 2,4-dimethyl-3-ethylpyrrole, 3- acetyl-2,4-dimethylpyrrole, ethyl-2,4-dimethyl-5-(ethoxycarbonyl)-3-pyrrole-propionate, ethyl-3,5-dimethyl-2-pyrrole-carboxylate. When the pyrrole-containing compound contains chromium, the resultant chromium compound can be called a chromium pyrrolide.

The most preferred pyrrole-containing compounds used in a trimerization catalyst system are selected from the group consisting of hydrogen pyrrolide, i.e., pyrrole ($C_4H_5N$) and/or 2,5-dimethyl pyrrole. While all pyrrole-containing compounds can produce catalysts with high activity and productivity, use of pyrrole and/or 2,5-dimethylpyrrole can produce a catalyst system with enhanced activity and selectivity to a desired trimerized product, such as, for example, the trimerization of ethylene to 1-hexene, as well as decreased polymer production.

The metal alkyl, also referred to earlier as an activating compound, can be any heteroleptic or homoleptic metal alkyl compound. One or more metal alkyls can be used. The ligand(s) on the metal can be aliphatic and/or aromatic. Preferably, the ligand(s) are any saturated or unsaturated aliphatic radical. The metal alkyl can have any number of carbon atoms. However, due to commercial availability and ease of use, the metal alkyl will usually comprise less than about 70 carbon atoms per metal alkyl molecule and preferably less than about 20 carbon atoms per molecule. Preferred metal alkyls include, but are not limited to, alkylaluminum compounds, alkylboron compounds, alkylmagnesium compounds, alkylzinc compounds and/or alkyllithium compounds. Exemplary metal alkyls include, but are not limited to, n-butyllithium, s-butyllithium, t-butyllithium, diethylmagnesium, diethylzinc, triethylaluminum, trimethylaluminum, triisobutylaluminum, and mixtures thereof.

Most preferably, activating compounds are selected from the group consisting of non-hydrolyzed, i.e., not pre-contacted with water, alkylaluminum compounds, derivatives of alkylaluminum compounds, halogenated alkylaluminum compounds, and mixtures thereof for improved product selectivity, as well as improved catalyst system reactivity, activity, and/or productivity. Exemplary compounds include, but are not limited to, triethylaluminum, tripropylaluminum, tributylaluminum, diethylaluminum chloride, diethylaluminum bromide, diethylaluminum ethoxide, ethylaluminum sesquichloride, and mixtures thereof for best catalyst system activity and product selectivity. The most preferred alkylaluminum compound is triethylaluminum, for best results in catalyst system activity and product selectivity, as well as commercial availability.

When a trimerization catalyst system is the desired product, the activating compound must be at least one non-hydrolyzed alkylaluminum compound, expressed by the general formulae $AlR_3$, $AlR_2X$, $AlRX_2$, $AlR_2OR$, $AlRXOR$, and/or $Al_2R_3X_3$, wherein R is an alkyl group and X is a halogen atom. Exemplary compounds include, but are not limited to, triethylaluminum, tripropylaluminum, tributylaluminum, diethylaluminumchloride, diethylaluminumbromide, diethylaluminumethoxide, diethylaluminum phenoxide, ethylaluminumethoxy- chloride, and/or ethylaluminum sesquichloride, Preferably, the activating compound for a trimerization catalyst system is a trialkylaluminum compound, $AlR_3$, for reasons given above. The most preferred trialkylaluminum compound is triethylaluminum, for reasons given above.

Formation of stable and active catalyst systems can take place in the presence of a unsaturated hydrocarbon. As discussed in the previous embodiment, an unsaturated hydrocarbon can be present either during the initial contacting of a chromium source, a pyrrole-containing compound and a metal alkyl, or can be introduced directly into a trimerization, oligomerization and/or polymerization reactor. Furthermore, one or more of the olefin reactants can be considered the unsaturated hydrocarbon.

Any unsaturated aromatic or aliphatic hydrocarbon can be used. Preferably, an unsaturated hydrocarbon initially is present in the reaction mixture and most preferably, an aromatic hydrocarbon and/or ethylene initially is present to produce a highly active catalyst in terms of activity and selectivity, as well as a stable catalyst system. The unsaturated hydrocarbon can have any number of carbon atoms per molecule. Usually, the unsaturated hydrocarbon will comprise less than about 70 carbon atoms per molecule, preferably less than about 20 carbon atoms per molecule, due to commercial availability and ease of use.

The unsaturated hydrocarbon can be a gas, liquid, or solid. Preferably, to effect thorough contacting and mixing of the chromium salt, pyrrole-containing compound, and metal alkyl, the unsaturated hydrocarbon will be in a liquid and/or dissolved state. Exemplary unsaturated aliphatic hydrocarbons include, but are not limited to, ethylene, 1-hexene, 1,3-butadiene, and mixtures thereof. The most preferred unsaturated aliphatic hydrocarbon is ethylene, since ethylene can be a reactant during trimerization, oligomerization, and/or polymerization. Exemplary unsaturated aromatic hydrocarbons include, but are not limited to, toluene, benzene, xylene, mesitylene, hexamethylbenzene, and mixtures thereof. Unsaturated aromatic hydrocarbons are preferred in order to improve catalyst system stability, as well as improve catalyst system activity. The most preferred unsaturated aromatic hydrocarbon is toluene, for best resultant catalyst system stability and activity.

If an unsaturated aromatic hydrocarbon is added prior to introduction of the chromium compound(s) to a trimerization, oligomerization and/or polymerization reactor, removal of, or stripping, the unsaturated aromatic hydrocarbon prior to introduction of the chromium compound(s) into a reactor can improve catalyst system activity and/or product selectivity. Removal of the unsaturated aromatic hydrocarbon can be done in any manner known in the art, such as, for example, flashing or evaporation. The resultant product is a concentrated, or saturated, solution of an inventive catalyst system.

When the unsaturated aromatic hydrocarbon is removed prior to introduction to a reactor, the concentrated, or saturated, solution of an inventive catalyst system can be dissolved in a solvent compatible with the trimerization, oligomerization and/or polymerization process to improve ease of handling the inventive catalyst system. Generally, the solvent is the same as the reactor diluent. Preferred solvents include, but are not limited to cyclohexane, isobutane, hexane, pentane, and mixtures thereof.

The reaction, optionally, also can take place in the presence of a halide source. The presence of a halide source in the reaction mixture can increase catalyst system activity and productivity, as well as increase product selectivity. Exemplary halides include, but are not limited to fluoride, chloride, bromide, and/or iodide. Due to ease of use and availability, chloride is the preferred halide. Based on improved activity, productivity, and/or selectivity, bromide is the most preferred halide.

The halide source can be any compound containing a halogen. Exemplary compounds include, but are not limited to compounds with a general formula of $R_mX_n$, wherein R can be any organic and/or inorganic radical, X can be a halide, selected from the group consisting of fluoride, chloride, bromide, and/or iodide, and m+n can be any number greater than 0. If R is an organic radical, preferably R has from about 1 to about 70 carbon atoms per radical, most preferably from 1 to 20 carbon atoms per radical, for best compatibility and catalyst system activity. If R is an inorganic radical, preferably R is selected from the group consisting of aluminum, silicon, germanium, hydrogen, boron, lithium, tin, gallium, indium, lead, and mixtures thereof. Specific exemplary compounds include, but are not limited to, methylene chloride, chloroform, benzylchloride, silicon tetrachloride, tin (II) chloride, tin (IV) chloride, germanium tetrachloride, boron trichloride, aluminum tribromide, aluminum trichloride, 1,4-dibromobutane, and/or 1-bromobutane.

Furthermore, the chromium source, the metal alkyl and/or unsaturated hydrocarbon can contain and provide a halide to the reaction mixture. Preferably, the halide source is an alkylaluminum halide and is used in conjunction with alkylaluminum compounds due to ease of use and compatibility, as well as improved catalyst system activity and product selectivity. Exemplary alkylaluminum halides include, but are not limited to, diisobutylaluminum chloride, diethylaluminum chloride, ethylaluminum sesquichloride, ethylaluminum dichloride, diethylaluminum bromide, diethylaluminum iodide, and mixtures thereof.

When a trimerization catalyst system is the desired product, preferably, the reaction mixture comprises a halide source. Furthermore, most preferably, the halide source is selected from the group consisting of tin (IV) halides, germanium halides, and mixtures thereof. The halide source, most preferably, is combined with the chromium source and pyrrole-containing compound prior to addition of a metal alkyl, i.e., the chromium source and pyrrole-containing compound are pretreated with a halide source, to increase catalyst system productivity.

The amount of each reactant used to prepare a trimerization catalyst system can be any amount sufficient that, when combined with one or more olefins, trimerization, as defined in this disclosure, occurs. Usually, to prepare a trimerization catalyst system, about one mole of chromium, as the element chromium (Cr), can be combined with about 1 to about 50 moles of pyrrole-containing compound and about 1 to about 75 moles of aluminum, as the element, in an excess of unsaturated hydrocarbon. If an optional halide source is present, usually about 1 to about 75 moles of halide, as the element, are present. Preferably, about 1 mole of chromium, calculated as the element chromium (Cr), can be combined with about 1 to about 15 moles of pyrrole-containing compound and about 5 to about 40 moles of aluminum, calculated as the element aluminum (Al), in an excess of unsaturated hydrocarbon. If an optional halide source is present, preferably about 1 to about 30 moles of halide, calculated as elemental halide (X), are present. Most preferably, about one mole of chromium, as the element (Cr), is combined with two to four moles of pyrrole-containing compound and 10 to 20 moles of aluminum, as the element (Al), in an excess of unsaturated hydrocarbon. If an optional halide source is present, most preferably 2 to 15 moles of halide, as an element (X), are present.

An excess of pyrrole-containing compound does not appear to improve catalyst system activity, productivity, and/or selectivity. An unsaturated hydrocarbon can improve catalyst system stability, activity, and/or selectivity. An excess of the unsaturated hydrocarbon can harm catalyst system selectivity and/or activity. Too much alkylaluminum can decrease catalyst system activity and product selectivity. Too little alkylaluminum can result in incomplete formation of a catalyst system, which in turn, can result in low catalyst system activity and increase formation of undesired polymeric by-products. An excess of an optional halide source can deactivate a catalyst system, and therefore can result un decreased catalyst system activity. As stated earlier, presence of a halide source can increase catalyst system activity and product selectivity.

The reactants can be combined in any manner under conditions suitable to form an effective catalyst system. While the reactants can be combined in any manner, preferably the pyrrole-containing compound is present in the reaction mixture prior to the introduction of the metal alkyl. If this order of addition is followed, a better catalyst system, in terms of product selectivity and catalyst system activity and productivity, can be produced.

The reaction preferably occurs in the absence of oxygen, which can deactivate the catalyst, and under anhydrous conditions, i.e., in the initial absence of water. Therefore a dry, inert atmosphere, such as, for example, nitrogen and/or argon is most preferred. Additionally, the metal alkyl is a non-hydrolyzed metal alkyl.

The reaction pressure can be any pressure which does not adversely effect the reaction. Generally, pressures within the range of from about atmospheric pressure to about three atmospheres are acceptable. For ease of operation atmospheric pressure is generally employed.

The reaction temperature can be any temperature. In order to effectuate a more efficient reaction, temperatures which maintain the reaction mixture in a liquid state, for reasons given above, are preferred.

The reaction time can be any amount of time necessary for the reaction to occur. The reaction can be considered a dissolution process; any amount of time which can dissolve substantially all reactants is sufficient. Depending on the reactants, as well as the reaction temperature and pressure, reaction time can vary. Usually, times of less than about 1 day can be sufficient. Usually, reaction time is less than about 60 minutes. Under optimum conditions, the reaction time can be within the range of from about 1 second to about 15 minutes. Longer times usually provide no additional benefit and shorter times may not allow sufficient time for complete reaction.

In accordance with the second embodiment of preparation, a heterogenerous, i.e., supported, catalyst system can be prepared in-situ in the reactor by adding solid support directly to the reactor. As stated earlier, exemplary catalyst supports include, but are not limited to, zeolites, inorganic oxides, either alone or in combination, phosphated inorganic oxides, and mixtures thereof. Particularly preferred are supports selected from the group consisting of silica, silica-alumina, alumina, fluorided alumina, silated alumina, thoria, aluminophosphate, aluminum phosphate, phosphated silica, phosphated alumina, silica-titania, coprecipitated silica/titania, fluorided/silated alumina, and mixtures, thereof, being presently preferred, as well as any one or more of these supports which can contain chromium. The presently most preferred catalyst support, because of the greatest trimerization activity, is aluminophosphate, as disclosed in U.S. Pat. No. 4,364,855 (1982), herein incorporated by reference. In-situ preparation of a heterogeneous catalyst system, used in a trimerization or oligomerization process, can decrease undesirable formation of polymer.

Heterogeneous trimerization, oligomerization, and/or polymerization catalyst systems can also be prepared in accordance with the second embodiment of the invention by forming a reaction mixture comprising a chromium source, a pyrrole-containing compound, a metal alkyl, an unsaturated hydrocarbon, and an inorganic oxide, as disclosed earlier. Optionally, as disclosed earlier, a halide source an be added. Reaction stoichiometries and reaction conditions are the same as those disclosed for the second embodiment of the invention.

Any excess of chromium source, in relation to the inorganic oxide catalyst support, is sufficient. However, usually, less than about 5 grams of chromium pyrrolide compound per gram of catalyst support is sufficient. Preferably, about 0.001 to about 1 gram of chromium pyrrolide compound per gram of support, and most preferably, 0.01 to 0.5 gram of chromium pyrrolide compound, or chromium source, per gram of support is used for best support loading and most efficient use of the reagents. The amount of chromium pyrrolide, or chromium source, compound per gram of support can be expressed in different, yet equivalent terms, such as, for example, moles of chromium per gram of support. Usually, less than about $8.6 \times 10^{-3}$ moles of chromium per gram of support is sufficient. Preferably, about $1.7 \times 10^{-6}$ to about $1.7 \times 10^{-5}$ to $8.6 \times 10^{-4}$ moles of chromium per gram of support are used, for reasons given above.

The resultant heterogeneous catalyst system can be collected by filtration, to recover a solid catalyst system product. The solid catalyst system is preferably kept under a dry, inert atmosphere to maintain chemical stability and reactivity.

Reactants

Reactants applicable for use in polymerization with the catalyst systems and processes of this invention are olefinic compounds which can polymerize, i.e., react the same or with other olefinic compounds. Catalyst systems of the invention can be used to polymerize at least one linear or branched mono-1-olefin having about 2 to about 8 carbon atoms. Exemplary compounds include, but are not limited to, ethylene, propylene, 1-butene, 1-pentene, 1-hexene, 1-octene, and mixtures thereof.

Reactants applicable for use in oligomerization processes with catalyst systems and processes of this invention are olefin compounds having from about 2 to about 30 carbon atoms per molecule and having at least one olefinic double bond. Exemplary mono-olefin compounds include, but are not limited to acyclic and cyclic olefins such as, for example, ethylene, propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes, and mixtures of any two or more thereof.

Exemplary diolefin compounds include, but are not limited to, 1,3-butadiene, isoprene, 1,4-pentadiene, and 1,5-hexadiene. If branched and/or cyclic olefins are used as reactants, while not wishing to be bound by theory, it is believed that steric hindrance could hinder the trimerization process. Therefore, the branched and/or cyclic portion(s) of the olefin preferably should be distant from the carbon-carbon double bond.

Trimerization, as used in this disclosure, is defined as the combination of any two, three, or more olefins, wherein the number of olefin, i.e., double, bonds is reduced by two. Reactants applicable for use in the trimerization process of this invention are olefinic compounds which can a) self-react, i.e., trimerize, to give useful products such as, for example, the self reaction of ethylene can give one hexene and the self-reaction of 1,3-butadiene can give 1,5-cyclooctadiene; and/or b) olefinic compounds which can react with other olefinic compounds, i.e., co-trimerize, to give useful products such as, for example, co-trimerization of ethylene plus hexene can give one decene and/or 1-tetradecene, co-trimerization of ethylene and 1-butene gives one octene, co-trimerization of 1-decene and ethylene can give 1-tetradecene and/or 1-docosene, or co-trimerization of 1,3-butadiene and 1,5-hexadiene can give 1,5-cyclooctadecadiene. For example, the number of olefin bonds in the combination of three ethylene units is reduced by two, to one olefin bond, in 1-hexene. In another example, the number of olefin bonds in the combination of two 1,3-butadiene units, is reduced by two, to two olefin bonds in 1,5-cyclooctadiene. As used herein, the term "trimerization" is intended to include dimerization of diolefins, as well as "co-trimerization", both as defined above.

Suitable trimerizable olefin compounds are those compounds having from about 2 to about 30 carbon atoms per molecule and having at least one olefinic double bond. Exemplary mono-olefin compounds include, but are not limited to acyclic and cyclic olefins such as, for example, ethylene, propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes, and mixtures of any two or more thereof. Exemplary diolefin compounds include, but are not limited to, 1,3-butadiene, 1,4-pentadiene, and 1,5-hexadiene. If branched and/or cyclic olefins are used as reactants, while not wishing to be bound by theory, it is believed that steric hindrance could hinder the trimerization process. Therefore, the branched and/or cyclic portion(s) of the olefin preferably should be distant from the carbon-carbon double bond.

Catalyst systems produced from a chromium source, a pyrrole-containing compound, a metal alkyl and an unsaturated hydrocarbon preferably are employed as a trimerization catalyst system, which can be used as a cocatalyst system with any other polymerization catalyst system. Optionally, as stated earlier, trimerization catalyst systems can be produced from a chromium pyrrolide (instead of a chromium source and a pyrrole containing compound), a metal alkyl and an unsaturated hydrocarbon.

Reaction Conditions

The reaction products, i.e., polymers and/or copolymers, can be prepared from the catalyst systems of this invention by solution reactions, slurry reactions, and/or gas phase reaction techniques using conventional equipment and contacting processes. Contacting of the monomer or monomers with the two catalyst systems, i.e., polymerization catalyst system and trimerization/oligomerization cocatalyst system, can be effected by any manner known in the art of homogeneous (liquid) or heterogeneous (solid) catalyst systems. One convenient method is to suspend a polymerization catalyst system in an organic medium and to agitate the mixture to maintain the polymerization catalyst system in suspension throughout the trimerization and/or polymerization process. An inventive cocatalyst system can then be added. A polymerization catalyst system and inventive cocatalyst system, preferably, can also be fed simultaneously to a polymerization reactor, via one or more catalyst and/or cocatalyst system feed streams. Other known contacting methods such as fluidized bed, gravitating bed, and fixed bed can also be employed.

Optionally, hydrogen can be added to the reactor to accelerate the reaction and/or increase catalyst system activity.

The catalyst systems of this invention are particularly suitable for use in trimerization and/or polymerizations. The slurry process is generally carried out in an inert diluent (medium), such as a paraffin, cycloparaffin, or aromatic hydrocarbon. Exemplary reactor diluents include, but are not limited to isobutane and cyclohexane. Isobutane can decrease the swelling of the polymer product. However, a homogeneous trimerization/oligomerization cocatalyst system is more soluble in cyclohexane. Therefore, a preferred diluent for a homogeneous trimerization or oligomeriztion process is cyclohexane and a preferred diluent for a heterogeneous trimerization or oligomerization process is isobutane. When the reactant is predominately ethylene, a temperature in the range of about 0° to about 300° C. generally can be used. Preferably, when the reactant is predominately ethylene, a temperature in the range of about 60° to about 150° C. is employed.

Any amount of polymerization catalyst system and cocatalyst system can be present in a polymerization reactor, in order to produce a polymer with a desired set of optimal properties, such as, for example, density, melt index, high load melt index and molecular weight. Usually, up to about 40 parts by weight of a supported, i.e., heterogeneous, cocatalyst system can be present for each part by weight of polymerization catalyst system. Preferably, about 1 to about 25 parts cocatalyst system for each part polymerization catalyst system, and most preferably, 3 to 15 parts by weight cocatalyst system for each part polymerization catalyst system are present, to produce a polymer with desirable physical and processing characteristics.

Products

The olefinic and/or polymeric products of this invention have established utility in a wide variety of application such as, for example, as monomers for use in the preparation of homopolymers, copolymers, and/or terpolymers. The polymeric products of this invention have established utility in a wide variety of application such as for example, polyethylene.

The further understanding of the present invention and its advantages will be provided by reference to the following examples.

Examples

Various, equivalent abbreviations are used throughout the disclosure and examples. Some of these include triethylaluminum as TEA, $Al(C_2H_4)_2$; diethylaluminum chloride as DEAC, $Al(C_2H_5)$; chromium (III) 2-ethylhexanoate as $Cr(EH)_3$, CrEH, $CrEl_3$; hydrogen pyrrolide as pyrrole, Py, PyH, $(C_4H_5N)$; chromium (III) acetylacetonate as $Cracac_3$, $Cr(acac)_3$, Cr(acac), Cracac, $Cr(C_5H_7O_2)_3$; chromium (III) pyrrolide as $CrPy_3$, $Cr(Py)_3$, $[Na(C_4H_{10}O_2)_2]$ $[Cr(C_4H_4N)_3Cl(C_4H_{10}O_2)]$, $[Na(DME)_2]$ $[Cr(C_4H_4N)_3Cl(DME)]$, $[Na(DME)_2]$ $[Cr(Py)_3Cl(DME)]$, Product V, Compound V; chromium (III) chloride tris-tetrahydrofuran as $CrCl_3THF_3$, $CrCl_3(THF)_3$; 2,5-dimethylpyrrole as hydrogen 2,5-dimethylpyrrolide, $C_6H_8N$, 2,5-DMP; butene as $C_4=$; 1-hexene as $1-C_6=$; hexene as $C_6$; octene as $c_8=$; decene as $C_{10}=$; dodecene as $C_{12}=$; and tetradecene as $C_{14}=$.

Preparation of Chromium-Containing Compounds

Manipulations of all reactants were carried out either in a drybox employing nitrogen, or in airless glassware employing vacuum or nitrogen. Tetrahydrofuran (THF), toluene, benzene, diethylbenzene (Aldrich, 97% mixture of 1,2-, 1,3-, 1,4- isomers) and pentane were purified by distillation over sodium-benzophenone ketyl under nitrogen, then degassed via a nitrogen purge. Dimethoxyethane (DME) (Aldrich, anhydrous) was degassed via nitrogen purge and used without further purification. Pyrrole (Aldrich, 98%) was vacuum distilled over sodium, then degassed via nitrogen purge. 2,5-Dimethylpyrrole was dried with calcium sulfate and vacuum distilled. Sodium 2,5-dimethylpyrrolide ($NaC_6H_8N$) was prepared by reacting 2,5-dimethylpyrrole with an excess of sodium (40% by weight dispersion in mineral spirits) in refluxing tetrahydrofuran under nitrogen. Sodium pyrrolide was prepared by reacting pyrrole with an equivalent molar amount (1:1) of NaH (Aldrich, 60% by weight in mineral oil) or sodium (40% dispersion by weight in mineral spirits) in dimethoxyethane or tetrahydrofuran (THF) at ambient temperature under nitrogen. Triethylaluminum (TEA) (Aldrich 1.0M, hexanes and 1.9M toluene) was used as received. Ketjen Grade B alumina ($Al_2O_3$) and Davison 952 silica ($SiO_2$) were the commercial materials used as supports for catalyst preparations. Fluorided-alumina ($F/Al_2O_3$, 15 wt % F) was prepared by the addition of a solution of $NH_3HF_2$ in methanol to Ketjen Grade B alumina. Phosphated silica ($P/SiO_2$, P/Si molar ratio=0.1) was prepared by the addition of a 10% $H_3PO_4$/methanol solution to Davison 952 silica. The aluminophosphate ($AlPO_4$) used in the following experiments was made as described in McDaniel et al, U.S. Pat. No. 4,364,855 (1982). The supports were activated by placing up to 25 g into a fritted quartz tube, fluidizing with air and calcining at 700° C., except for $P/SiO_2$ at 350° C., for 3 hours. The air stream was switched to nitrogen until the support cooled to ambient temperature.

Chromium pyrrolide complexes were typically prepared from anhydrous chromium (II or III) chloride and sodium pyrrolide as follows:

A typical synthetic procedure useful to prepare chromium pyrrolide complexes was that of reacting the chromium chlorides with sodium pyrrolide ($NaC_4H_4N$, also referred to as NaPy) in refluxing tetrahydrofuran (THF). A molar reactant stoichiometry of $1CrCl_2$ and $2NaPy$ resulted in the isolation of a polymeric material, Product II, as the major product and a pentanuclear complex, Product I, $(Cr_5(NC_4H_4)_{10}(OC_4H_8)_4)$, as the minor product, see Equation 1. Using molar excess of NaPy resulted in the isolation of the dianionic square planar complex {Cr(NC$_4$H$_4$)}{Na}$_2$.2OC$_4$H., Product III, and the octahedral complex {Cr(C$_4$H$_4$N)$_5$(OC$_4$H.)}{Na}$_2$.4OC$_4$H$_8$, Product IV, see Equation 2. Each of the products was isolated through precipitation (Product II) or crystallization (Products I, III, IV) from THF solutions by the addition of pentane.

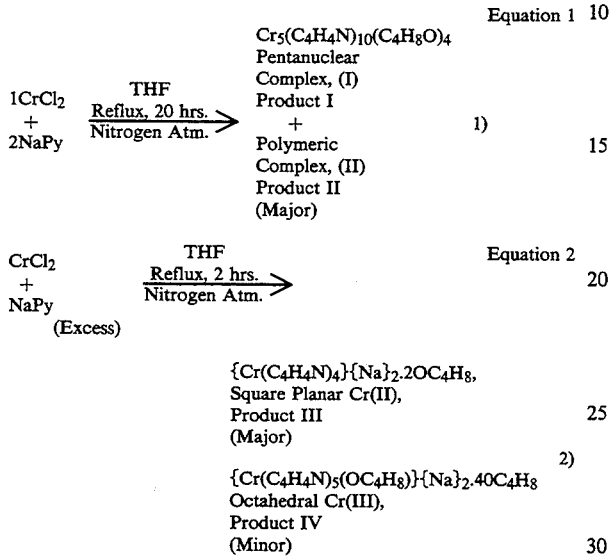

Equation 1

Equation 2

EXAMPLE I

To prepare the pentanuclear complex, Product I, (Cr$_5$(NC$_4$H$_4$)$_{10}$(OC$_4$H$_8$)$_4$), and the polymeric material, Product II, chromous chloride (2.0 g/16.27 mmole) was combined with sodium pyrrolide (33.68 mmole) in tetrahydrofuran and refluxed 20 hours. The reaction mixture was filtered (medium porosity frit) and the filtrate was used for fractional crystallization of both (Cr$_5$(NC$_4$H$_4$)$_{10}$(OC$_4$H$_8$)$_4$), Product I, and the polymeric material, Product II, through the addition of pentane. The polymeric material crystallized as a blue solid followed by (Cr$_5$(NC$_4$H$_4$)$_{10}$(OC$_4$H$_8$)$_4$) as opaque dark blue/purple crystals.

Figure 2:
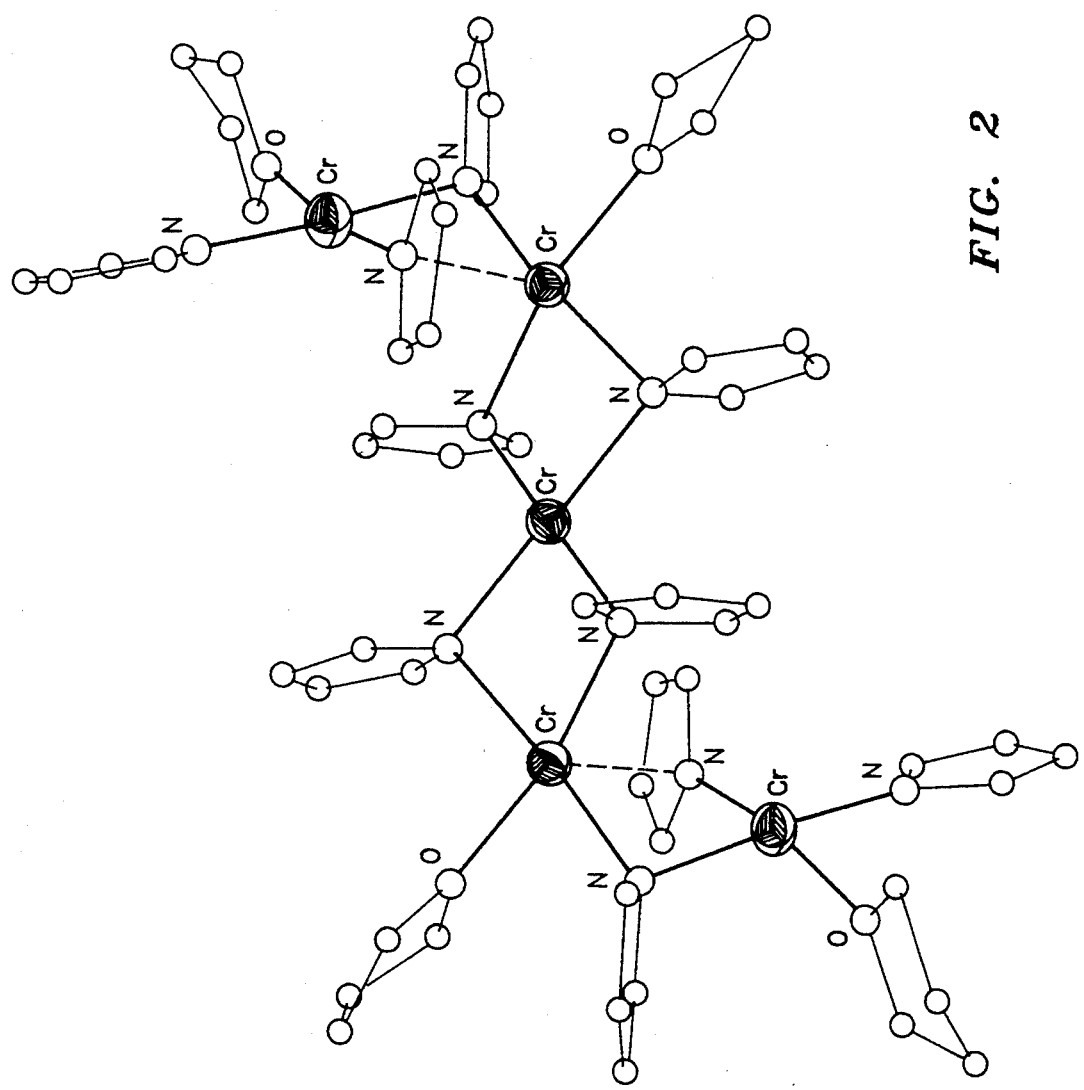
FIG. 2 is a further simplified ball and stick projection, with the exception of the chromium atoms which are represented as thermal ellipsoids, or a structural representation, of the same molecule shown in FIG. 1.

Analysis calculated for C$_{56}$H$_{72}$N$_{10}$O$_4$Cr$_5$, Product I: C, 55.62; H, 6.00; N, 11.58%, by weight. Found: C, 55.46; 1, 6.32; N, 11.15%, by weight. Analysis found for Product II: Cr, 11.5; C, 59.75; H, 7.61; N, 9.17%, by weight, but variable upon precipitation conditions. An x-ray crystal structure of Product I showed a pentanuclear complex incorporating bridging amido-pyrrolyl, terminal amido-pyrrolyl, and tetrahydrofuran ligands (FIGS. 1 and 2).

Example II

To prepare {Cr(NC$_4$H$_4$)}{Na}$_2$.20C$_4$H$_8$, Product III, and {Cr(C$_4$H$_4$N)$_5$(OC$_4$H$_4$)}{Na}$_2$.40C$_4$H$_8$, Product IV, chromous chloride (3.0 g/24.4 mmole) was combined with sodium pyrrolide (100.9 mmole) in tetrahydrofuran and refluxed 2 hours, see Equation 2. The reaction mixture was filtered (medium porosity frit) and the filtrate was used for fractional crystallization of both {Cr(NC$_4$H$_4$)$_4$}{Na}$_2$.20C$_4$H$_g$, Product Ill, and {Cr(C$_4$H$_4$N)$_5$(OC$_4$H$_8$)}{Na}$_2$.40C$_4$H$_8$, Product IV, through the addition of pentane. Product III crystallized as translucent orange/red crystals followed by Product IV as translucent purple crystals. While not wishing to be bound by theory, the formation of Product IV is believed to result from the presence of chromic chloride in the chromous chloride reagent (Alfa, chromium (II) chloride, anhydrous, contains 5-10% by weight CrCl$_3$) used in the preparation.

Figure 4:
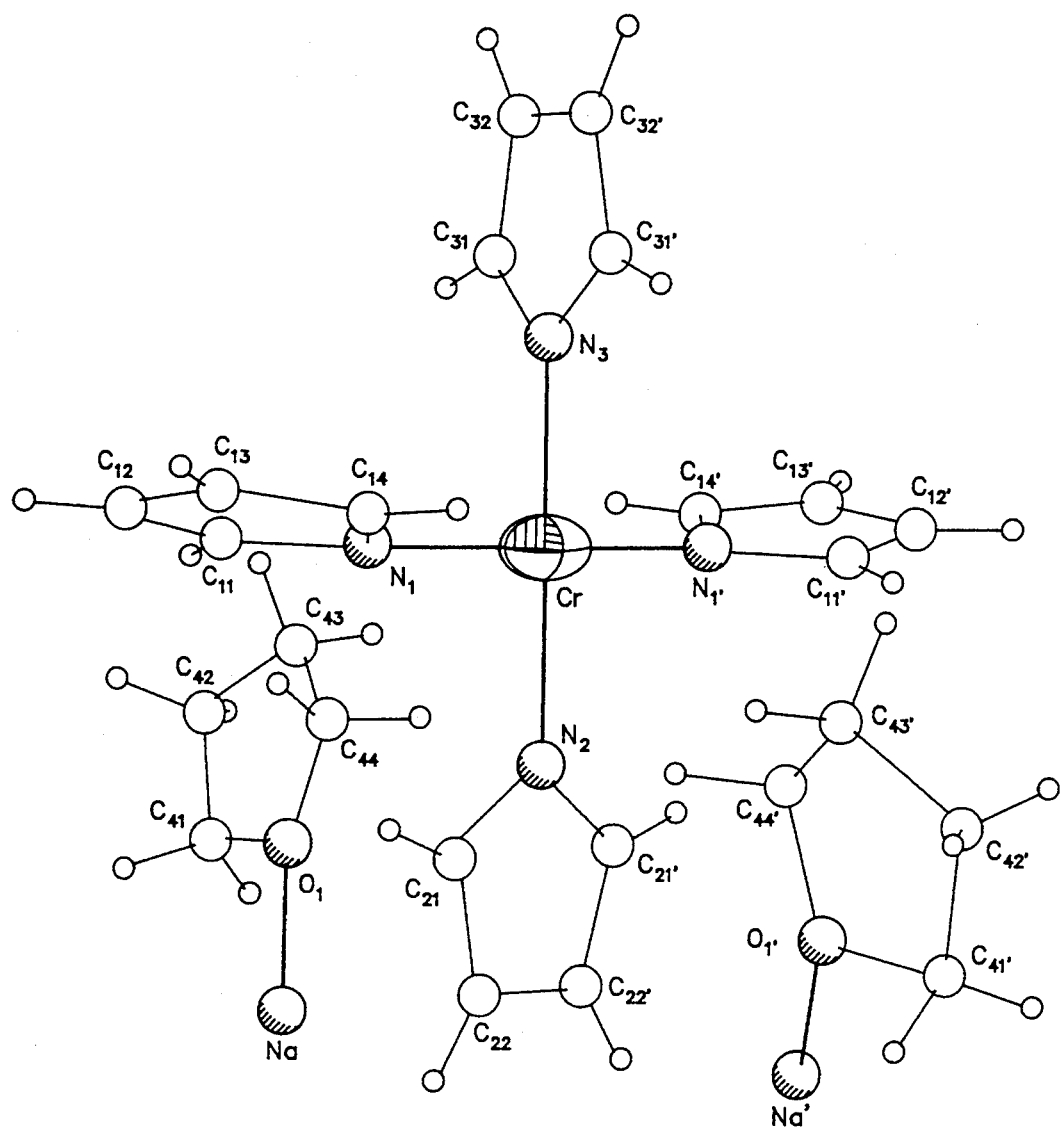
FIG. 4 is a further simplified ball and stick projection, with the exception of the chromium atoms which are represented as thermal ellipsoids, or a structural representation, of the same molecule shown in FIG. 3, however, the entire crystal structure or lattice, with the formula $Cr(NC_4H_4)_4Na_2.20C_4H_8$ is shown.
Figure 5:
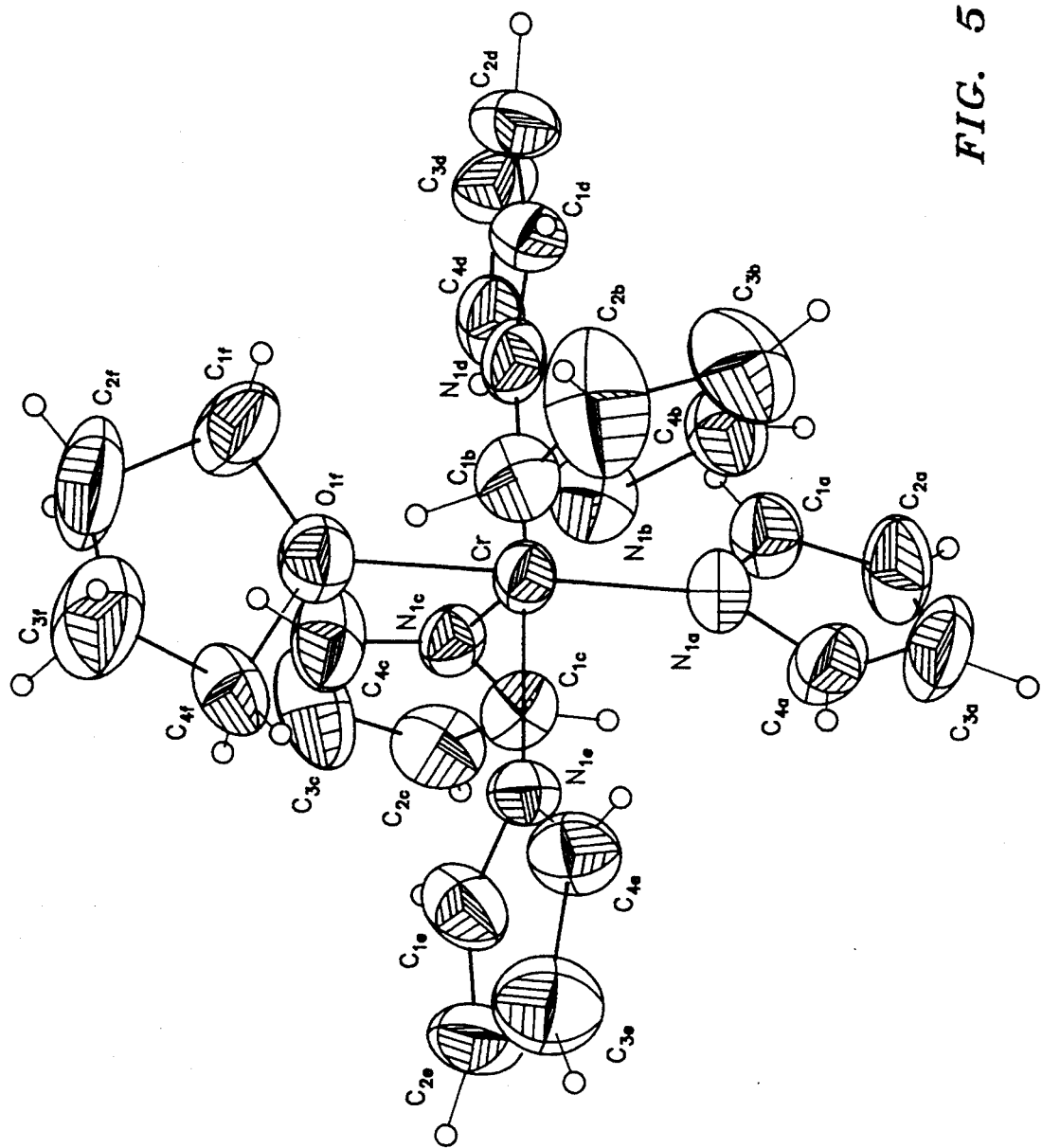
FIG. 5 is a computer generated ORTEP drawing of the structure, or a simplified structural representation or formula, of a molecule of Product IV, $[Cr(NC_4H_4)_5(OC_4H_8)]^{-2}$, as determined by single crystal x-ray crystallography.
Figure 6:
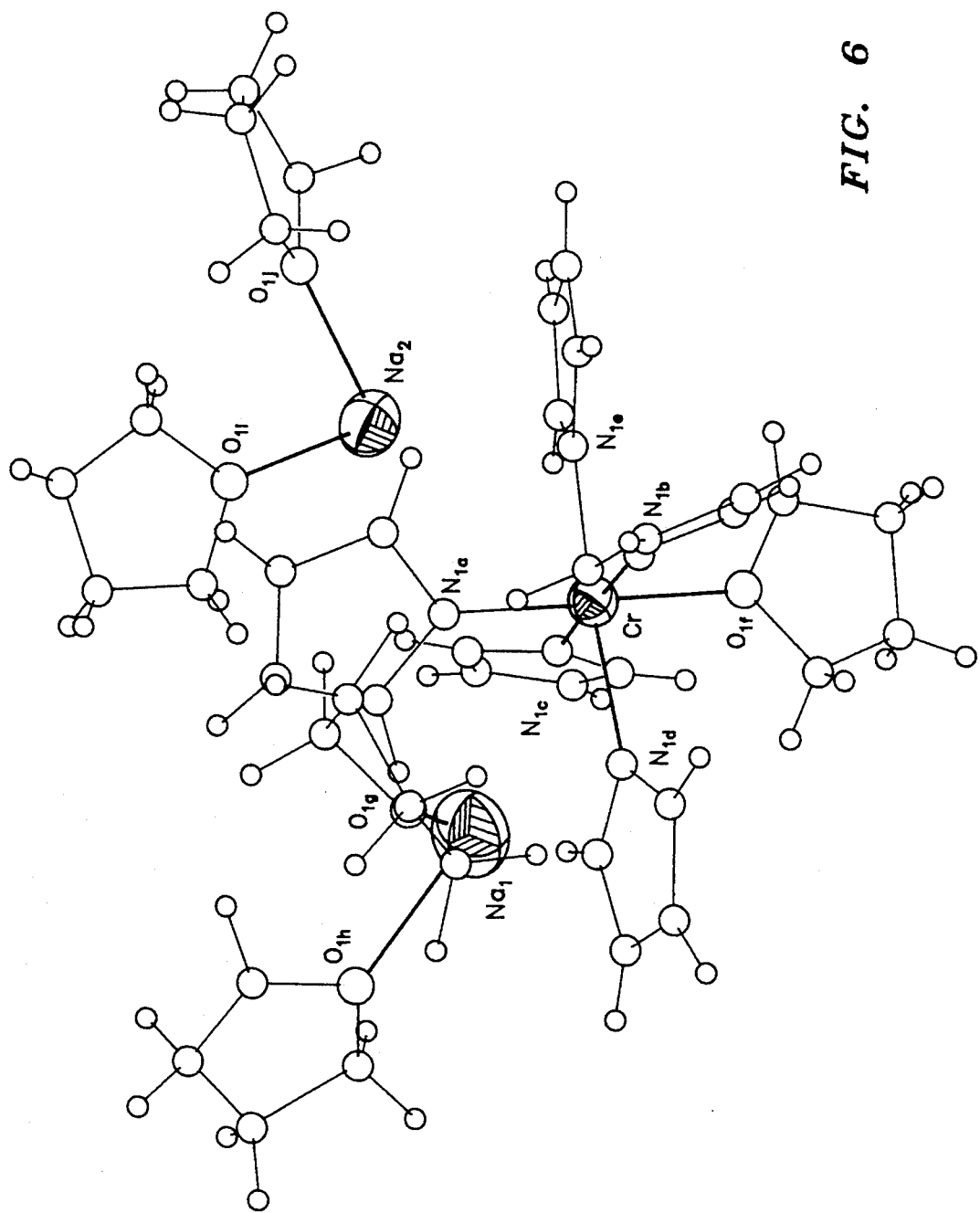
FIG. 6 is a further simplified ball and stick projection, with the exception of the chromium atoms which are represented as thermal ellipsoids, or a structural representation, of the same molecule shown in FIG. 5, however the entire crystal structure or lattice, with the formula $[Cr(NC_4H_4)_5(OC_4H_4)][Na]_2.4(OC_4H_4)$, is shown.

Analysis calculated for C$_{24}$H$_{32}$N$_4$O$_2$CrNa$_2$, Product III: C, 56.94; H, 6.32; N, 11.07% by weight. Found: C, 57.04; H, 6.30; N, 10.92%, by weight. Analysis calculated for C$_{40}$H$_{60}$N$_5$O$_5$CrNa$_2$, Product IV: C, 60.90; H, 7.67; N, 8.88% by weight. Found: C, 60.81; H, 7.74; N, 9.44%, by weight. An x-ray crystal structure of Product III showed a square planar complex incorporating terminal amido-pyrrolyl ligands (FIG. 4). An x-ray crystal structure of Product IV showed an octahedral complex incorporating terminal amido-pyrrolyl and a tetrahydrofuran ligand (FIGS. 5 and 6).

EXAMPLE III

The reaction product obtained from sodium pyrrolide and CrCl$_3$ was the most preferred in the preparation of an active catalyst. Pyrrole (7.0 ml/100.9 mmole) was mixed with Natt (4.2 g of 60%, about 105 mmole) in dimethoxyethane at ambient temperature until bubbling ceased. Chromic chloride (5.33 g/33.7 mmole) was added to the solution at ambient temperature. The reaction mixture was refluxed under nitrogen for five hours, see Equation 3. This resulted in a dark green solution. The solution was filtered (medium porosity frit) and stripped of solvent under vacuum and pumped dry under vacuum for 12 hours. The resultant chromium pyrrolide complex was a green solid, Product V. It was used in the preparation of an active catalyst without further purification.

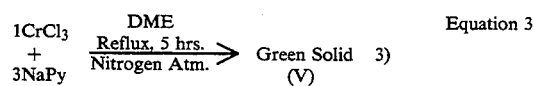

Equation 3

EXAMPLE IV

All single crystal x-ray structure analyses were performed by Crystalytics Company, Lincoln, Nebraska. Examples IV, V, VI, and IX contain the resultant analytical and subsequently computer-generated data.

A single crystal x-ray structure was obtained for [Cr$_5$(NC$_4$H$_4$)$_{10}$(OC$_4$H$_8$)$_4$], Product I, and shown in FIGS. 1 and 2. The description of the single-crystal sample and mounting used for data collection are as follows:

Color: Dark blue
Shape: Rectangular parallelepiped
Dimensions: 0.20×0.48×0.80 mm
Crystal Mount: Crystal was sealed inside a thin-walled glass capillary with epoxy under N$_2$.
Crystal Orientation: Crystal was oriented with its longest edge nearly parallel to the phi axis of the diffractometer.
Width at half-height from Ω Scans: 0.38°
The space group and cell data are as follows:
Crystal System: Triclinic
Space Group and Number: P1-C$_i$ (No. 2)
Number of Computer-Centered Reflections Used in the Least-Squares Refinement of the Cell Dimensions: 15 20>25° °C.=20±1°
Lattice Constants with esd's:
a=10.803(2)Å
b=9.825(2)Å c = 14.212(4)Å
$\alpha$ = 85.59(2)°
$\beta$ = 96.23(2)°
$\partial$ = 109.99(2)°
V = 1407.9(6)Å$^3$
Z = 1
$\lambda$ = 0.71073Å
Molecular Weight: 1209.24 amu
Calculated Density: 1.427 g/cm$^{-1}$
Linear Absorption Coefficient: 0.96 mm$^{-1}$ Tables I–V list the resultant parameters used to generate the molecular structures shown in FIGS. 1 and 2.

TABLE I

Atomic Coordinates for Nonhydrogen Atoms in Crystalline $[Cr_5(NC_4H_4)_{10}(OC_4H_8)_4]$[a]

| Atom Type[b] | Fractional Coordinates | | | Equivalent Isotropic Thermal Parameter, B, Å$^2$ × 10[c] |
|---|---|---|---|---|
| | 10$^4$x | 10$^4$y | 10$^4$z | |
| Cr$_1$ | 0[d] | 0[d] | 0[d] | 25(1) |
| Cr$_2$ | 636(1) | 2281(1) | 1500(i) | 24(1) |
| Cr$_3$ | −1179(1) | 841(1) | 3122(1) | 28(1) |
| N$_{1a}$ | −1155(3) | 935(3) | 715(2) | 25(1) |
| C$_{1a}$ | −2195(4) | 64(4) | 1231(3) | 31(1) |
| C$_{2a}$ | −3313(4) | 390(5) | 965(3) | 41(1) |
| C$_{3a}$ | −3014(4) | 1486(5) | 257(3) | 43(1) |
| C$_{4a}$ | −1728(4) | 1791(4) | 116(3) | 34(1) |
| N$_{1b}$ | 1566(3) | 1902(3) | 331(2) | 29(1) |
| C$_{1b}$ | 1753(4) | 3095(4) | −308(3) | 36(1) |
| C$_{2b}$ | 3035(5) | 3751(5) | −432(3) | 51(2) |
| C$_{3b}$ | 3736(4) | 2986(5) | 131(3) | 51(2) |
| C$_{4b}$ | 2823(4) | 1865(4) | 587(3) | 38(1) |
| N$_{1c}$ | −320(3) | 2997(3) | 2480(2) | 27(1) |
| C$_{1c}$ | 375(4) | 3732(4) | 3273(3) | 34(1) |
| C$_{2c}$ | 29(5) | 4919(4) | 3383(3) | 43(1) |
| C$_{3c}$ | −909(5) | 4967(4) | 2631(3) | 42(1) |
| C$_{4c}$ | −1105(4) | 3809(4) | 2101(3) | 32(1) |
| N$_{1d}$ | 443(3−) | 350(3) | 2743(2) | 28(1) |
| C$_{1d}$ | 1600(4) | 715(4) | 3289(3) | 36(1) |
| C$_{2d}$ | 2321(4) | −133(5) | 3102(3) | 46(2) |
| C$_{3d}$ | 1567(5) | −1070(5) | 2403(3) | 46(2) |
| C$_{4d}$ | 422(4) | −763(4) | 2203(3) | 36(1) |
| N$_{1e}$ | −1972(3) | −1122(3) | 3801(2) | 35(1) |
| C$_{1e}$ | −1344(5) | −2107(4) | 4069(3) | 41(1) |
| C$_{2e}$ | −2189(5) | −3307(4) | 4503(3) | 44(1) |
| C$_{3e}$ | −3361(5) | −3061(4) | 4531(3) | 47(1) |
| C$_{4e}$ | −3206(5) | −1731(4) | 4097(3) | 47(1) |
| O$_{1f}$ | 2351(3) | 3985(3) | 1883(2) | 32(1) |
| C$_{1f}$ | 3536(4) | 4018(4) | 2483(3) | 43(1) |
| C$_{2f}$ | 4470(6) | 5479(6) | 2336(5) | 76(2) |
| C$_{3f}$ | 3642(5) | 6408(5) | 2147(4) | 62(2) |
| C$_{4f}$ | 2396(4) | 5463(4) | 1635(3) | 40(1) |
| O$_{1g}$ | −2551(3) | 1543(3) | 3659(2) | 35(1) |
| C$_{1g}$ | −3763(4) | 1733(5) | 3232(3) | 44(1) |
| C$_{2g}$ | −4097(5) | 2625(6) | 3907(4) | 57(2) |
| C$_{3g}$ | −3524(5) | 2241(6) | 4845(3) | 57(2) |
| C$_{4g}$ | −2319(5) | 1977(6) | 4633(3) | 50(2) |

[a]The numbers in parentheses are the estimated standard deviations in the last significant digit.
[b]Atoms are labeled in agreement with FIG. 1.
[c]This is one-third of the trace of the orthogonalized B$_{ij}$ tensor.
[d]This is a symmetry-required value and is therefore listed without an estimated standard deviation.

TABLE II

Anisotropic Thermal Parameters for Nonhydrogen Atoms in Crystalline $[Cr_5(NC_4H_4)_{10}(OC_4H_8)_4]$[a,b]

| Atom Type[c] | Anisotropic Thermal Parameter (Å$^2$ × 10) | | | | | |
|---|---|---|---|---|---|---|
| | B$_{11}$ | B$_{22}$ | B$_{33}$ | B$_{12}$ | B$_{13}$ | B$_{23}$ |
| Cr$_1$ | 20(1) | 23(1) | 32(1) | 5(1) | 5(1) | −4(1) |
| Cr$_2$ | 23(1) | 22(1) | 27(1) | 7(1) | 3(1) | −2(1) |
| Cr$_3$ | 27(1) | 26(1) | 34(1) | 11(1) | 8(1) | 1(1) |
| N$_{1a}$ | 21(1) | 27(1) | 29(1) | 8(1) | 1(1) | −2(1) |
| C$_{1a}$ | 28(2) | 31(2) | 30(2) | 4(2) | 8(1) | −4(1) |
| C$_{2a}$ | 23(2) | 49(2) | 49(2) | 8(2) | 5(2) | −16(2) |
| C$_{3a}$ | 31(2) | 51(2) | 52(2) | 22(2) | −7(2) | −11(2) |
| C$_{4a}$ | 36(2) | 32(2) | 34(2) | 15(2) | −2(2) | −3(2) |
| N$_{1b}$ | 24(1) | 25(1) | 35(1) | 3(1) | 5(1) | −4(1) |
| C$_{1b}$ | 40(2) | 31(2) | 33(2) | 2(1) | 11(1) | −1(1) |
| C$_{2b}$ | 46(2) | 42(2) | 54(2) | −7(2) | 24(2) | −5(2) |
| C$_{3b}$ | 25(2) | 50(2) | 71(3) | −3(2) | 15(2) | −27(2) |
| C$_{4b}$ | 29(2) | 38(2) | 48(2) | 10(1) | 0(2) | −15(2) |
| N$_{1c}$ | 28(1) | 25(1) | 30(1) | 11(1) | 3(1) | −2(1) |
| C$_{1c}$ | 36(2) | 35(2) | 31(2) | 10(1) | 4(1) | −3(1) |
| C$_{2c}$ | 52(2) | 34(2) | 43(2) | 13(2) | 6(2) | −13(1) |
| C$_{3c}$ | 51(2) | 31(2) | 50(2) | 22(2) | 5(2) | −5(2) |
| C$_{4c}$ | 35(2) | 34(2) | 31(2) | 16(1) | 4(1) | 1(1) |
| N$_{1d}$ | 32(1) | 23(1) | 31(1) | 12(1) | 6(1) | 3(1) |
| C$_{1d}$ | 33(2) | 32(2) | 42(2) | 9(2) | 6(2) | −0(1) |
| C$_{2d}$ | 36(2) | 50(2) | 59(2) | 24(2) | 6(2) | 11(2) |
| C$_{3d}$ | 61(3) | 44(2) | 47(2) | 36(2) | 11(2) | 3(2) |
| C$_{4d}$ | 49(2) | 35(2) | 31(2) | 23(2) | 4(2) | 1(2) |
| N$_{1e}$ | 36(2) | 30(1) | 42(2) | 13(1) | 14(1) | 4(1) |
| C$_{1e}$ | 46(2) | 36(2) | 46(2) | 20(2) | 10(2) | 6(2) |
| C$_{2e}$ | 64(3) | 30(2) | 37(2) | 15(2) | 7(2) | 4(1) |
| C$_{3e}$ | 55(3) | 31(2) | 46(2) | −1(2) | 18(2) | −0(2) |
| C$_{4e}$ | 39(2) | 38(2) | 62(2) | 9(2) | 17(2) | 4(2) |
| O$_{1f}$ | 29(1) | 25(1) | 40(1) | 6(1) | −1(1) | −2(1) |
| C$_{1f}$ | 34(2) | 44(2) | 45(2) | 9(2) | −8(2) | −6(2) |
| C$_{2f}$ | 45(3) | 67(3) | 95(4) | −3(2) | −15(3) | −6(3) |
| C$_{3f}$ | 59(3) | 34(2) | 78(3) | −2(2) | −6(3) | −9(2) |
| C$_{4f}$ | 45(2) | 23(2) | 48(2) | 7(1) | 6(2) | −1(1) |
| O$_{1g}$ | 34(1) | 41(1) | 37(1) | 19(1) | 7(1) | −1(1) |
| C$_{1g}$ | 31(2) | 56(2) | 50(2) | 20(2) | 4(2) | −5(2) |
| C$_{2g}$ | 47(3) | 65(3) | 72(3) | 35(2) | 2(2) | −12(2) |
| C$_{3g}$ | 60(3) | 75(3) | 50(2) | 36(2) | 16(2) | −8(2) |
| C$_{4g}$ | 45(2) | 77(3) | 35(2) | 27(2) | 8(2) | −5(2) |

[a]The numbers in parentheses are the estimated standard deviations in the last significant digit.
[b]The form of the anisotropic thermal parameter is given in reference 8 on page 6 of the structure report.
[c]Atoms are labeled in agreement with FIG. 1.

TABLE III

Atomic Coordinates for Hydrogen Atoms in Crystalline $[Cr_5(NC_4H_4)_{10}(OC_4H_8)_4]$[a]

| Atom Type[b] | Fractional Coordinates | | |
|---|---|---|---|
| | 10$^4$x | 10$^4$y | 10$^4$z |
| H$_{1a}$ | −2129 | −661 | 1707 |
| H$_{2a}$ | −4154 | −55 | 1219 |
| H$_{3a}$ | −3608 | 1937 | −69 |
| H$_{4a}$ | −1267 | 2508 | −339 |
| H$_{1b}$ | 1053 | 3405 | −617 |
| H$_{2b}$ | 3405 | 4593 | −834 |
| H$_{3b}$ | 4676 | 3202 | 189 |
| H$_{4b}$ | 3031 | 1158 | 1020 |
| H$_{1c}$ | 1013 | 3445 | 3687 |
| H$_{2c}$ | 364 | 5592 | 3881 |
| H$_{3c}$ | −1331 | 5685 | 2512 |
| H$_{4c}$ | −1704 | 3580 | 1540 |
| H$_{1d}$ | 1881 | 1460 | 3743 |
| H$_{2d}$ | 3177 | −88 | 3396 |
| H$_{3d}$ | 1807 | −1790 | 2120 |
| H$_{4d}$ | −291 | −1252 | 1752 |
| H$_{1e}$ | −446 | −1976 | 3968 |
| H$_{2e}$ | −1997 | −4161 | 4742 |
| H$_{3e}$ | −4139 | −3699 | 4803 |
| H$_{4e}$ | −3878 | −1286 | 4012 |
| H$_{1fa}$ | 3351 | 3836 | 3136 |
| H$_{1fb}$ | 3882 | 3308 | 2299 |
| H$_{2fa}$ | 5068 | 5771 | 2893 |
| H$_{2fb}$ | 4965 | 5524 | 1806 |
| H$_{3fa}$ | 3462 | 6711 | 2728 |
| H$_{3fb}$ | 4068 | 7245 | 1757 |
| H$_{4fa}$ | 2417 | 5653 | 964 |
| H$_{4fb}$ | 1641 | 5625 | 1839 |
| H$_{1ga}$ | −3631 | 2231 | 2623 |
| H$_{1gb}$ | −4455 | 813 | 3162 |
| H$_{2ga}$ | −5037 | 2381 | 3901 |
| H$_{2gb}$ | −3704 | 3640 | 3750 |
| H$_{3ga}$ | −4129 | 1385 | 5124 |
| H$_{3gb}$ | −3307 | 3025 | 5266 |
| H$_{4ga}$ | −2173 | 1220 | 5050 |

TABLE III-continued

Atomic Coordinates for Hydrogen Atoms in Crystalline $[Cr_5(NC_4H_4)_{10}(OC_4H_8)_4]$[a]

| Atom Type[b] | Fractional Coordinates | | |
|---|---|---|---|
| | $10^4 x$ | $10^4 y$ | $10^4 z$ |
| $H_{4gb}$ | −1565 | 2846 | 4703 |

[a]Hydrogen atoms were included in the structure factor calculations as idealized atoms (assuming sp$^2$- or sp$^3$-hybridization of the carbon atoms and a C—N bond length of 0.96Å) "riding" on their respective carbon atoms. The isotropic thermal parameter of each hydrogen atom was fixed at 1.2 times the equivalent isotropic thermal parameter of the carbon atoms to which it is covalently bonded
[b]Hydrogen atoms are labeled with the same numerical and literal subscripts as their carbon atoms with an additional literal subscript (a or b) where necessary to distinguish between hydrogen atoms bonded to the same carbon.

TABLE IV

Bond Lengths Involving Nonhydrogen Atoms in Crystalline $[Cr_5(NC_4H_4)_{10}(OC_4H_8)_4]$[a]

| Type[b] | Length, Å | Type[b] | Length, Å |
|---|---|---|---|
| $Cr_1 \cdots Cr_2$ | 3.066(1) | $O_{1f}-C_{1f}$ | 1.451(5) |
| $Cr_2 \cdots Cr_3$ | 3.121(1) | $O_{1f}-C_{4f}$ | 1.453(5) |
| | | $O_{1g}-C_{1g}$ | 1.448(6) |
| $Cr_1-N_{1a}$ | 2.153(3) | $O_{1g}-C_{4g}$ | 1.451(5) |
| $Cr_1-N_{1b}$ | 2.092(3) | | |
| $Cr_2-N_{1a}$ | 2.178(3) | $C_{1a}-C_{2a}$ | 1.360(6) |
| $Cr_2-N_{1b}$ | 2.149(3) | $C_{2a}-C_{3a}$ | 1.395(6) |
| $Cr_2-N_{1c}$ | 2.112(4) | $C_{3a}-C_{4a}$ | 1.351(6) |
| $Cr_3-N_{1c}$ | 2.172(3) | $C_{1b}-C_{2b}$ | 1.338(6) |
| $Cr_3-N_{1d}$ | 2.101(4) | $C_{2b}-C_{3b}$ | 1.393(7) |
| $Cr_3-N_{1e}$ | 2.037(3) | $C_{3b}-C_{4b}$ | 1.376(6) |
| | | $C_{1c}-C_{2c}$ | 1.365(7) |
| $Cr_2-O_{1f}$ | 2.082(2) | $C_{2c}-C_{3c}$ | 1.400(6) |
| $Cr_3-O_{1g}$ | 2.068(3) | $C_{3c}-C_{4c}$ | 1.356(6) |
| | | $C_{1d}-C_{2d}$ | 1.376(7) |
| $N_{1a}-C_{1a}$ | 1.399(4) | $C_{2d}-C_{3d}$ | 1.396(6) |
| $N_{1a}-C_{4a}$ | 1.397(5) | $C_{3d}-C_{4d}$ | 1.367(8) |
| $N_{1b}-C_{1b}$ | 1.398(5) | $C_{1e}-C_{2e}$ | 1.370(5) |
| $N_{1b}-C_{4b}$ | 1.379(6) | $C_{2e}-C_{3e}$ | 1.374(8) |
| $N_{1c}-C_{1c}$ | 1.368(4) | $C_{3e}-C_{4e}$ | 1.366(6) |
| $N_{1c}-C_{4c}$ | 1.394(6) | | |
| $N_{1d}-C_{1d}$ | 1.349(5) | $C_{1f}-C_{2f}$ | 1.460(6) |
| $N_{1d}-C_{4d}$ | 1.377(5) | $C_{2f}-C_{3f}$ | 1.474(9) |
| $N_{1e}-C_{1e}$ | 1.370(6) | $C_{3f}-C_{4f}$ | 1.496(6) |
| $N_{1e}-C_{4e}$ | 1.361(6) | $C_{1g}-C_{2g}$ | 1.496(8) |
| | | $C_{2g}-C_{3g}$ | 1.485(7) |
| | | $C_{3g}-C_{4g}$ | 1.476(9) |

[a]The numbers in parentheses are the estimated standard deviations in the last significant digit.
[b]Atoms are labeled in agreement with FIG. 1.

TABLE V

Bond Angles Involving Nonhydrogen Atoms in Crystalline $[Cr_5(NC_4H_4)_{10}(OC_4H_8)_4]$[a]

| Type[b] | Angle, deg | Type[b] | Angle, deg |
|---|---|---|---|
| $N_{1a}Cr_1N_{1b}$ | 84.8(1) | $Cr_1N_{1a}Cr_2$ | 90.2(1) |
| $N_{1a}Cr_1N_{1a}$,[c] | 180.0(—)[d] | $Cr_1N_{1a}C_{1a}$ | 121.2(2) |
| $N_{1b}Cr_1N_{1a}$,[c] | 95.2(1) | $Cr_2N_{1a}C_{1a}$ | 118.0(2) |
| $N_{1b}Cr_1N_{1b}$,[c] | 180.0(—)[d] | $Cr_1N_{1a}C_{4a}$ | 113.4(2) |
| | | $Cr_2N_{1a}C_{4a}$ | 110.6(2) |
| $N_{1a}Cr_2N_{1b}$ | 82.9(1) | $C_{1a}N_{1a}C_{4a}$ | 103.5(3) |
| $N_{1a}Cr_2N_{1c}$ | 96.5(1) | $Cr_1N_{1b}Cr_2$ | 92.6(1) |
| $N_{1b}Cr_2N_{1c}$ | 168.9(1) | $Cr_1N_{1b}C_{1b}$ | 117.9(2) |
| $N_{1a}Cr_2O_{1f}$ | 162.4(1) | $Cr_2N_{1b}C_{1b}$ | 107.6(3) |
| $N_{1b}Cr_2O_{1f}$ | 89.5(1) | $Cr_1N_{1b}C_{4b}$ | 120.6(3) |
| $N_{1c}Cr_2O_{1f}$ | 87.9(1) | $Cr_2N_{1b}C_{4b}$ | 113.0(3) |
| | | $C_{1b}N_{1b}C_{4b}$ | 104.4(3) |
| $N_{1c}Cr_3N_{1d}$ | 88.1(1) | $Cr_2N_{1c}Cr_3$ | 93.5(1) |
| $N_{1c}Cr_3N_{1e}$ | 176.5(1) | $Cr_2N_{1c}C_{1c}$ | 121.4(3) |
| $N_{1d}Cr_3N_{1e}$ | 93.5(1) | $Cr_3N_{1c}C_{1c}$ | 100.0(2) |
| $N_{1c}Cr_3O_{1f}$ | 88.8(1) | $Cr_2N_{1c}C_{4c}$ | 116.1(2) |
| $N_{1d}Cr_3O_{1g}$ | 170.4(1) | $Cr_3N_{1c}C_{4c}$ | 121.5(2) |
| $N_{1e}Cr_3O_{1g}$ | 89.1(1) | $C_{1c}N_{1c}C_{4c}$ | 104.2(3) |
| | | $Cr_3N_{1d}C_{1d}$ | 121.3(3) |
| $N_{1a}C_{1a}C_{2a}$ | 110.6(3) | $Cr_3N_{1d}C_{4d}$ | 127.8(3) |
| $C_{1a}C_{2a}C_{3a}$ | 107.5(4) | $C_{1d}N_{1d}C_{4d}$ | 106.4(4) |
| $C_{2a}C_{3a}C_{4a}$ | 106.9(4) | $Cr_3N_{1e}C_{1e}$ | 126.3(3) |
| $C_{3a}C_{4a}N_{1a}$ | 111.5(3) | $Cr_3N_{1e}C_{4e}$ | 128.3(3) |
| $N_{1b}C_{1b}C_{2b}$ | 111.2(4) | $C_{1e}N_{1e}C_{4e}$ | 105.3(3) |

TABLE V-continued

Bond Angles Involving Nonhydrogen Atoms in Crystalline $[Cr_5(NC_4H_4)_{10}(OC_4H_8)_4]$[a]

| Type[b] | Angle, deg | Type[b] | Angle, deg |
|---|---|---|---|
| $C_{1b}C_{2b}C_{3b}$ | 107.4(4) | | |
| $C_{2b}C_{3b}C_{4b}$ | 107.0(4) | $Cr_2O_{1f}C_{1f}$ | 131.5(2) |
| $C_{3b}C_{4b}N_{1b}$ | 110.1(4) | $Cr_2O_{1f}C_{4f}$ | 118.9(2) |
| $N_{1c}C_{1c}C_{2c}$ | 110.9(4) | $C_{1f}O_{1f}C_{4f}$ | 109.1(3) |
| $C_{1c}C_{2c}C_{3c}$ | 106.8(4) | $Cr_3O_{1g}C_{1g}$ | 131.9(3) |
| $C_{2c}C_{3c}C_{4c}$ | 107.2(4) | $Cr_3O_{1g}C_{4g}$ | 118.6(3) |
| $C_{3c}C_{4c}N_{1c}$ | 110.9(3) | $C_{1g}O_{1g}C_{4g}$ | 109.5(4) |
| $N_{1d}C_{1d}C_{2d}$ | 110.3(4) | | |
| $C_{1d}C_{2d}C_{3d}$ | 106.7(4) | $O_{1f}C_{1f}C_{2f}$ | 105.0(4) |
| $C_{2d}C_{3d}C_{4d}$ | 106.6(5) | $C_{1f}C_{2f}C_{3f}$ | 104.9(4) |
| $C_{3d}C_{4d}N_{1d}$ | 109.9(3) | $C_{2f}C_{3f}C_{4f}$ | 104.4(4) |
| $N_{1e}C_{1e}C_{2e}$ | 110.0(4) | $C_{3f}C_{4f}O_{1f}$ | 105.4(4) |
| $C_{1e}C_{2e}C_{3e}$ | 107.2(4) | $O_{1g}C_{1g}C_{2g}$ | 104.8(4) |
| $C_{2e}C_{3e}C_{4e}$ | 106.7(4) | $C_{1g}C_{2g}C_{3g}$ | 104.2(5) |
| $C_{3e}C_{4e}N_{1e}$ | 110.8(5) | $C_{2g}C_{3g}C_{4g}$ | 104.2(4) |
| | | $C_{3g}C_{4g}O_{1g}$ | 106.1(4) |

[a]The numbers in parentheses are the estimated standard deviations in the last significant digit.
[b]Atoms are labeled in agreement with FIG. 1
[c]Atoms labeled with a prime( ) are related to nonprimed atoms by the symmetry operation -x, -y, -z where the fractional coordinates (x, y, z) are given in Table I.
[d]This is a symmetry-required value and is therefore listed without an estimated standard deviation.

EXAMPLE V

Figure 3:
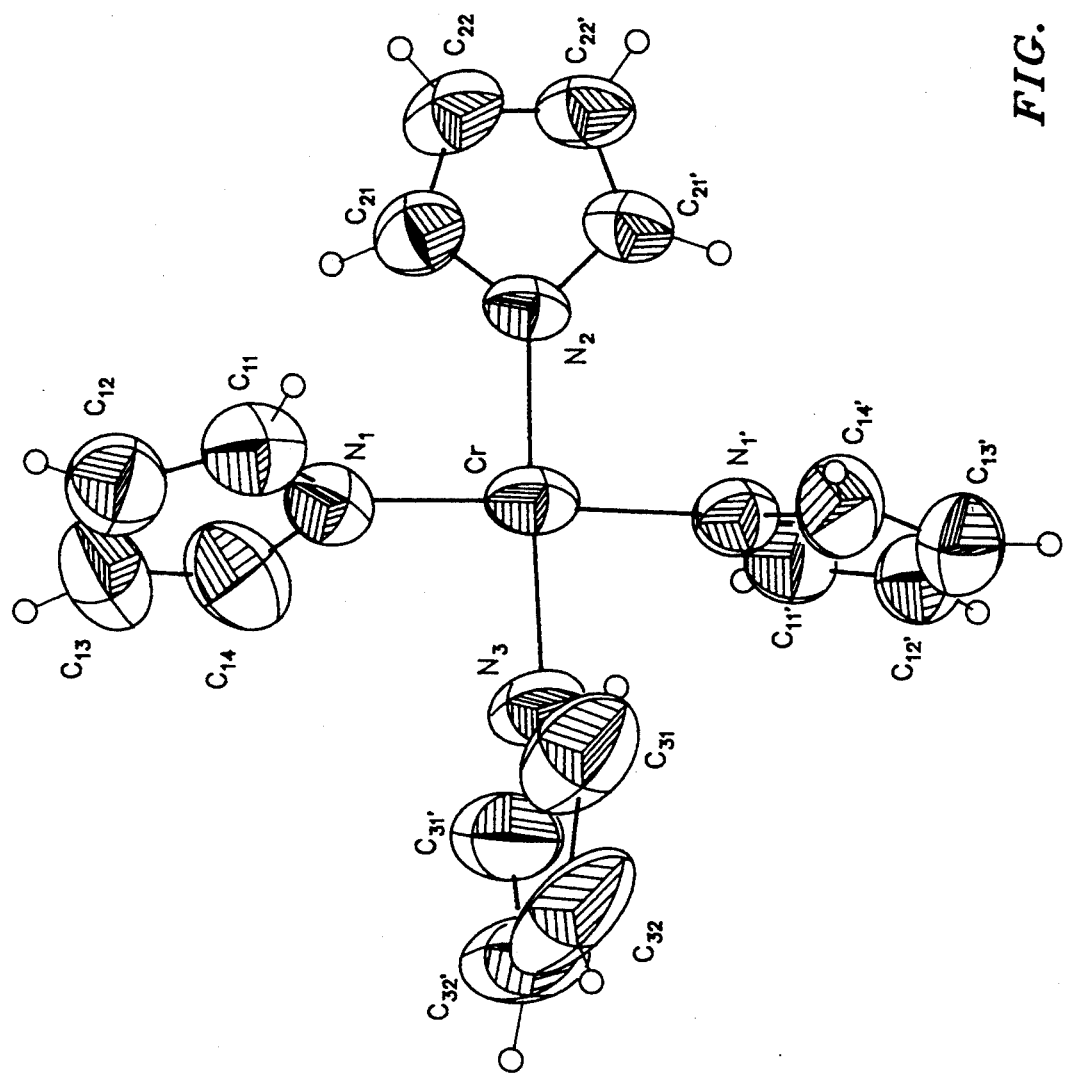
FIG. 3 is a computer generated ORTEP drawing of the structure, or a simplifid structural representation or formula, of a molecule of Product III, $[Cr(NC_4H_4)_4]^{-2}$, as determined by single crystal x-ray crystallography.

A single crystal x-ray structure was obtained for $Cr(NC_4H_4)_4$, a portion of Product III and shown in FIG. 3. A single crystal x-ray structure was obtained for $[Na]_2[Cr(NC_4H_4)_4] \cdot 2(OC_4H_8)$, Product III and shown in FIG. 4. The description of the single-crystal sample and mounting used for the data collection are as follows:

Color: Red-Orange
Shape: Rectangular parallelepiped
Dimensions: 0.50×0.55×0.65 mm
Crystal Mount: Crystal was glued to the inside of a thin-walled glass capillary and sealed under $N_2$.
Crystal Orientation: Crystal was oriented with its longest edge nearly parallel to the phi axis of the diffractometer.
Width at Half-height from w Scans: 0.86°
The space group and cell data are as follows:
Crystal System: Monoclinic
Space Group and Number: $C2/c - C_{2h}$ (no. 15)
Number of Computer-Centered Reflections Used in the Least-Squares Refinement of the Cell Dimensions:
Dimensions: 15 20>25° °C.=20+1°
Lattice Constants with esd's:
a=9.522(2)Å
b=15.118(2)Å
c=18.967(3)Å
$\alpha$=90.00°
$\beta$=98.99(1)°
$\partial \leq$90.00°
V=2697(1)Å$^3$
Z=4
$\lambda$=0.71073Å
Molecular Weight: 506.52 amu
Calculated Density: 1.248 g/cm$^{-3}$
Linear Absorption Coefficient: 0.47 mm$^{-1}$ Tables VI-X list the resultant parameters used to generate the molecular structures shown in FIGS. 3 and 4.

TABLE VI

Atomic Coordinates for Nonhydrogen Atoms in Crystalline $(Na)_2\{Cr(NC_4H_4)_4\} \cdot 2(OC_4H_8)$ [a]

| Atom Type [b] | Fractional Coordinates | | | Equivalent Isotropic Thermal Parameter. $B$, Å$^2 \times 10$ [c] |
|---|---|---|---|---|
| | $10^4x$ | $10^4y$ | $10^4z$ | |
| Anion | | | | |
| Cr | 0 [d] | 2982(1) | 2500 [d] | 58(1) |
| $N_1$ | 1901(4) | 2924(2) | 3183(2) | 56(1) |
| $N_2$ | 8 [d] | 4343(3) | 2500 [d] | 52(1) |
| $N_3$ | 8 [d] | 1612(3) | 2500 [d] | 70(2) |
| $C_{11}$ | 3241(5) | 2958(3) | 3008(3) | 65(2) |
| $C_{12}$ | 4224(6) | 2768(3) | 3587(3) | 73(2) |
| $C_{13}$ | 3513(7) | 2638(4) | 4146(3) | 82(2) |
| $C_{14}$ | 2094(7) | 2734(4) | 3884(3) | 76(2) |
| $C_{21}$ | 907(5) | 4884(3) | 2926(3) | 68(1) |
| $C_{22}$ | 582(4) | 5753(3) | 2766(3) | 69(2) |
| $C_{31}$ | 390(5) | 1081(3) | 1996(4) | 94(2) |
| $C_{32}$ | 326(7) | 213(3) | 2189(5) | 133(6) |
| Cation | | | | |
| Na | 2301(2) | 6879(1) | 1783(1) | 69(1) |
| Solvent of Crystallization | | | | |
| $O_1$ | 2065(4) | 5108(2) | 838(2) | 83(1) |
| $C_{41}$ | 2759(11) | 5174(5) | 239(4) | 143(4) |
| $C_{42}$ | 2884(11) | 4319(5) | −79(4) | 148(4) |
| $C_{43}$ | 1893(10) | 3786(5) | 264(5) | 142(4) |
| $C_{44}$ | 1699(9) | 4231(4) | 902(4) | 120(3) |

[a] The numbers in parentheses are the estimated standard deviations in the last significant digit.
[b] Atoms are labeled in agreement with FIGS. 3 and 4.
[c] This is one-third of the trace of the orthogonalized $B_{ij}$ tensor.
[d] This is a symmetry-required value and is therefore listed without an estimated standard deviation.

TABLE VII

Anisotropic Thermal Parameters for Nonhydrogen atoms in Crystalline $\{Na\}_2\{Cr(NC_4H_4)_4\} \cdot 2(OC_4H_8)$ [a,b]

| Atom Type [c] | Anisotropic Thermal Parameter (Å$^2 \times 10$) | | | | | |
|---|---|---|---|---|---|---|
| | $B_{11}$ | $B_{22}$ | $B_{33}$ | $B_{12}$ | $B_{13}$ | $B_{23}$ |
| Anion | | | | | | |
| Cr | 64(1) | 34(1) | 55(1) | 0 [d] | 15(1) | 0 [d] |
| $N_1$ | 69(2) | 44(2) | 56(2) | 6(1) | 12(1) | 6(1) |
| $N_2$ | 64(3) | 39(2) | 56(3) | 0 [d] | 16(2) | 0 [d] |
| $N_3$ | 65(3) | 38(2) | 107(4) | 0 [d] | 14(3) | 0 [d] |
| $C_{11}$ | 78(3) | 50(2) | 70(3) | −6(2) | 18(2) | 2(2) |
| $C_{12}$ | 70(3) | 62(3) | 84(3) | 4(2) | 7(2) | −8(2) |
| $C_{13}$ | 103(4) | 79(3) | 58(3) | 22(3) | −8(3) | 0(2) |
| $C_{14}$ | 86(3) | 86(3) | 58(3) | 16(3) | 16(2) | 5(2) |
| $C_{21}$ | 66(2) | 45(2) | 70(3) | −2(2) | 15(2) | −6(2) |
| $C_{22}$ | 68(3) | 38(2) | 105(4) | −7(2) | 27(2) | −9(2) |
| $C_{31}$ | 65(3) | 61(3) | 152(5) | 6(2) | 9(3) | −36(3) |
| $C_{32}$ | 71(5) | 46(2) | 266(15) | 6(3) | −20(6) | −44(4) |
| Cation | | | | | | |
| Na | 70(1) | 57(1) | 81(1) | −2(1) | 15(1) | −15(1) |
| Solvent of Crystallization | | | | | | |
| $O_1$ | 108(2) | 65(2) | 82(2) | −10(2) | 38(2) | −16(2) |
| $C_{41}$ | 222(8) | 112(5) | 116(5) | −46(5) | 92(6) | −22(4) |
| $C_{42}$ | 192(8) | 168(8) | 107(5) | 12(6) | 70(5) | −32(5) |
| $C_{43}$ | 147(6) | 109(6) | 177(8) | −27(6) | 48(6) | −69(6) |
| $C_{44}$ | 177(6) | 77(4) | 124(5) | −21(4) | 76(5) | −14(3) |

[a] The numbers in parentheses are the estimated standard deviations in the last significant digit.
[b] The form of the anisotropic thermal parameter is given in reference 8 on page 6 of the structure report.
[c] Atoms are labeled in agreement with FIGS. 1 and 2.
[d] This is a symmetry-required value and is therefore listed without an estimated standard deviation.

TABLE VIII

Atomic Coordinates for Hydrogen Atoms in Crystalline $\{Na\}_2\{Cr(NC_4H_4)_4\} \cdot (2(OC_4H_8)$ [a]

| Atom Type [b] | Fractional Coordinates | | |
|---|---|---|---|
| | $10^4x$ | $10^4y$ | $10^4z$ |
| Anion | | | |
| $H_{11}$ | 3456 | 3881 | 2541 |
| $H_{12}$ | 5235 | 2748 | 3680 |
| $H_{13}$ | 3922 | 2488 | 4628 |
| $H_{14}$ | 1341 | 2679 | 4164 |
| $H_{21}$ | 1665 | 4687 | 3285 |
| $H_{22}$ | 1071 | 6262 | 2985 |
| $H_{31}$ | 706 | 1274 | 1565 |
| $H_{32}$ | 483 | −301 | 1937 |
| Solvent of Crystallization | | | |
| $H_{41a}$ | 2250 | 5576 | −100 |
| $H_{41b}$ | 3710 | 5388 | 385 |
| $H_{42a}$ | 3756 | 4891 | −1 |
| $H_{42b}$ | 2464 | 4348 | −583 |
| $H_{43a}$ | 995 | 3707 | −39 |
| $H_{43b}$ | 2326 | 3220 | 377 |
| $H_{44a}$ | 2295 | 3973 | 1304 |
| $H_{44b}$ | 723 | 4191 | 969 |

[a] Hydrogen atoms were included in the structure factor calculations as idealized atoms (assuming sp$^2$- or sp$^3$-hybridization of the carbon atoms and a C—H bond length of 0.96 Å) "riding" on their respective carbon atoms. The isotropic thermal parameter of each hydrogen atom was fixed at 1.2 times the equivalent isotropic thermal parameter of the carbon atom to which it is covalently bonded.
[b] Hydrogen atoms are labeled with the same numerical subscripts as the carbon atoms to which they are covalently bonded with an additional literal subscript (a or b) where necessary to distinguish between hydrogens bonded to the same carbon.

TABLE IX

Anion Bond lengths and Bond Angles Involving Nonhydrogen atoms in Crystalline $\{Na\}_2\{Cr(NC_4H_4)_4\} \cdot (2(OC_4H_8)$ [a]

| Type b | Length, Å | Type b | Length, Å |
|---|---|---|---|
| Cr-$N_1$ | 2.057(3) | $C_{11}$-$C_{12}$ | 1.355(7) |
| Cr-$N_2$ | 2.056(4) | $C_{12}$-$C_{13}$ | 1.361(9) |
| Cr-$N_3$ | 2.072 (5) | $C_{13}$-$C_{14}$ | 1.374(9) |
| | | $C_{21}$-$C_{22}$ | 1.372(6) |
| $N_1$-$C_{11}$ | 1.369(7) | $C_{22}$-$C_{22'}$ [c] | 1.379(9) |
| $N_1$-$C_{14}$ | 1.344(6) | $C_{31}$-$C_{32}$ | 1.376(7) |
| $N_2$-$C_{21}$ | 1.360(5) | $C_{32}$-$C_{32'}$ [c] | 1.327(18) |
| $N_3$-$C_{31}$ | 1.344(7) | | |
| Type [b] | Angle, deg. | Type [b] | Angle, deg. |
| $N_1CrN_2$ | 92.5(1) | $N_1C_{11}C_{12}$ | 110.5(5) |
| $N_1CrN_3$ | 87.5(1) | $C_{11}C_{12}C_{13}$ [c] | 107.3(5) |
| $N_1CrN_{1'}$ [c] | 175.1(2) | $C_{12}C_{13}C_{14}$ | 106.4(5) |
| $N_2CrN_3$ | 180.0(−) [d] | $N_1C_{14}C_{13}$ | 110.9(5) |
| | | $N_2C_{21}C_{22}$ | 110.2(4) |
| $CrN_1C_{11}$ | 127.5(5) | $C_{21}C_{22}C_{22'}$ [c] | 106.8(3) |
| $CrN_1C_{14}$ | 127.1(4) | $N_3C_{31}C_{32}$ | 109.1(6) |
| $C_{11}N_1C_{14}$ | 104.9(4) | $C_{31}C_{32}C_{32'}$ [c] | 107.5(5) |
| $CrN_2C_{21}$ | 127.0(2) | | |
| $C_{21}N_2C_{21'}$ [c] | 106.0(5) | | |
| $CrN_3C_{31}$ | 126.7(3) | | |
| $C_{31}N_3C_{31'}$ [c] | 106.7(6) | | |

[a] The numbers in parentheses are the estimated standard deviations in the last significant digit.
[b] Atoms are labeled in agreement with FIG. 4.
[c] Atoms labeled with a prime(′) are related to nonprimed atoms by the symmetry operation −x, y, ½-z.

TABLE X

Bond Lengths and Angles Involving the Nonhydrogen Atoms of the Cation and Solvent of Crystallization in $\{Na\}_2\{Cr(NC_4H_4)_4\} \cdot 2(OC_4H_8)$ [a]

| Type [b] | Length, Å | Type [b] | Length, Å |
|---|---|---|---|
| Na-$O_1$ | 2.313(4) | $O_1$-$C_{41}$ | 1.390(10) |
| | | $O_1$-$C_{44}$ | 1.382(7) |
| Na...$N_{1''}$ [c] | 2.888(4) | | |
| Na...$N_{3''}$ [c] | 2.830(4) | $C_{41}$-$C_{42}$ | 1.43(1) |
| | | $C_{42}$-$C_{43}$ | 1.42(1) |
| | | $C_{43}$-$C_{44}$ | 1.42(1) |
| Type [b] | Angle, deg. | Type [b] | Angle, deg. |
| $O_1NaN_{1''}$ [c] | 128.6(3) | $C_{41}O_1C_{44}$ | 107.9(5) |
| $O_1NaN_{3''}$ [c] | 121.8(3) | | |
| $N_{1''}NaN_{3''}$ [c] | 59.9(3) | $O_1C_{41}C_{42}$ | 109.0(7) |

TABLE X-continued

Bond Lengths and Angles Involving the
Nonhydrogen Atoms of the Cation and
Solvent of Crystallization in
${Na}_2\{Cr(NC_4H_4)_4\}\cdot 2(OC_4H_8)$[a]

| | | $C_{41}C_{42}C_{43}$ | 105.0(8) |
|---|---|---|---|
| $NaO_1C_{41}$ | 125.7(4) | $C_{42}C_{43}C_{44}$ | 107.0(7) |
| $NaO_1C_{44}$ | 121.8(4) | $O_1C_{44}C_{43}$ | 107.6(7) |

[a]The numbers in parentheses are the estimated standard deviations in the last significant digit.
[b]Atoms are labeled in agreement with FIG. 4.
[c]Atoms labeled with a prime(') are related to nonprimed atoms by the symmetry operation ½-x, ½-y, ½-z.

EXAMPLE VI

Single crystal x-ray structures were obtained for $Cr(NC_4H_4)_5(OC_4H_8)]$, shown in FIG. 5, and $[Cr(NC_4H_4)_5(OC_4H_4)][Na]_2\cdot 4(OC_4H_8)$, Product IV, and shown in FIG. 6. The description of the single-crystal sample and mounting used for data collection are as follows:

Color: Purple
Shape: Rectangular parallelepiped
Dimensions: 0.50×0.55×0.63 mm
Crystal Mount: Crystal was glued to the inside of a thin-walled glass capillary and sealed under $N_2$.
Crystal Orientation: Crystal was oriented with its longest edge nearly parallel to the phi axis of the diffractometer.
Width at Half-height from Ω Scans: 0.42°
The space group and cell data are as follows:
Crystal System: Monoclinic
Space Group and Number: $P2_1$-$C_2$(No. 4)
Number of Computer-Centered Reflections Used in the Least-Squares Refinement of the Cell Dimensions: 15  20>20° °C.=20±1°
Lattice Constants with esd's:
a=10.042(2)Å
b=17.242(4)Å
c=13.025(3)Å
α=90.00°
β=106.54(2)°
∂=90.00°
V=2162(1)Å³
Z=2
λ=0.71073Å
Molecular Weight=788.93 amu
Calculated Density: 1.212 g/cm⁻³
Linear Absorption Coefficient: 0.32 mm⁻¹

Tables XI-XV list the resultant parameters used to generate the molecular structures shown in FIGS. 5 and 6.

TABLE XI

Atomic Coordinates for Nonhydrogen Atoms in Crystalline $[Cr(NC_4H_4)_5(OC_4H_8)][Na]_2\cdot 4(OC_4H_8)$

| Atom Type[b] | Fractional Coordinates | | | Equivalent Isotropic Thermal Parameter. B, Å² × 10[c] |
|---|---|---|---|---|
| | $10^4x$ | $10^4y$ | $10^4z$ | |
| Anion | | | | |
| Cr | 198(1) | 1477 | 2531(1) | 32(1) |
| $N_{1a}$ | 1694(5) | 2026(3) | 2028(4) | 40(2) |
| $C_{1a}$ | 1749(7) | 2782(4) | 1742(6) | 48(2) |
| $C_{2a}$ | 2929(8) | 2926(5) | 1420(7) | 66(2) |
| $C_{3a}$ | 3661(7) | 2236(5) | 1554(6) | 62(3) |
| $C_{4a}$ | 2899(6) | 1695(5) | 1913(5) | 52(2) |
| $N_{1b}$ | 1651(5) | 1087(3) | 3885(4) | 40(2) |
| $C_{1b}$ | 1463(8) | 560(4) | 4575(5) | 48(2) |
| $C_{2b}$ | 2572(9) | 518(6) | 5423(8) | 82(4) |
| $C_{3b}$ | 3554(8) | 1064(6) | 5275(6) | 70(3) |
| $C_{4b}$ | 2952(6) | 1382(5) | 4340(5) | 48(2) |

TABLE XI-continued

Atomic Coordinates for Nonhydrogen Atoms in Crystalline $[Cr(NC_4H_4)_5(OC_4H_8)][Na]_2\cdot 4(OC_4H_8)$

| Atom Type[b] | Fractional Coordinates | | | Equivalent Isotropic Thermal Parameter. B, Å² × 10[c] |
|---|---|---|---|---|
| | $10^4x$ | $10^4y$ | $10^4z$ | |
| $N_{1c}$ | −1326(5) | 1888(3) | 1250(4) | 38(2) |
| $C_{1c}$ | −1200(8) | 2172(4) | 266(6) | 51(2) |
| $C_{2c}$ | −2458(8) | 2270(5) | −476(6) | 58(3) |
| $C_{3c}$ | −3435(8) | 2038(6) | 56(7) | 75(3) |
| $C_{4c}$ | −2710(7) | 1826(5) | 1091(6) | 56(3) |
| $N_{1d}$ | −32(5) | 2455(4) | 3445(5) | 43(2) |
| $C_{1d}$ | 504(7) | 2562(5) | 4505(6) | 49(2) |
| $C_{2d}$ | 107(9) | 3278(5) | 4774(8) | 72(3) |
| $C_{3d}$ | −698(8) | 3629(5) | 3832(6) | 59(3) |
| $C_{4d}$ | −769(7) | 3108(4) | 3055(6) | 52(2) |
| $N_{1e}$ | 315(5) | 505(4) | 1690(4) | 40(2) |
| $C_{1e}$ | −574(8) | 277(5) | 704(6) | 55(3) |
| $C_{2e}$ | −197(10) | −432(5) | 403(7) | 67(3) |
| $C_{3e}$ | 990(10) | −662(6) | 1256(8) | 79(4) |
| $C_{4e}$ | 1265(8) | −92(4) | 2016(7) | 51(3) |
| $O_{1f}$ | −1356(4) | 926(3) | 3083(4) | 43(1) |
| $C_{1f}$ | −2047(7) | 1244(5) | 3800(6) | 57(3) |
| $C_{2f}$ | −3263(10) | 713(6) | 3706(9) | 98(5) |
| $C_{3f}$ | −2833(11) | −21(6) | 3402(8) | 93(4) |
| $C_{4f}$ | −1903(8) | 171(5) | 2724(7) | 64(3) |
| Cation 1 | | | | |
| $Na_1$ | 2254(3) | 3336(2) | 3737(3) | 75(1) |
| Cation 2 | | | | |
| $Na_2$ | 1430(3) | 974(2) | 126(2) | 62(1) |
| Solvent Molecules of Crystallization | | | | |
| $O_{1g}$ | 4576(6) | 3329(4) | 4706(5) | 83(2) |
| $C_{1g}$ | 5748(9) | 3100(10) | 4433(9) | 125(6) |
| $C_{2g}$ | 6723(12) | 2831(11) | 5281(9) | 145(7) |
| $C_{3g}$ | 6503(15) | 3272(11) | 6146(11) | 204(8) |
| $C_{4g}$ | 5037(14) | 3498(11) | 5737(10) | 170(8) |
| $O_{1h}$ | 2342(7) | 4602(4) | 3279(6) | 97(3) |
| $C_{1h}$ | 1316(11) | 5151(7) | 2894(10) | 112(5) |
| $C_{2h}$ | 2017(16) | 5830(9) | 2541(11) | 153(7) |
| $C_{3h}$ | 3180(12) | 5561(10) | 2425(10) | 131(6) |
| $C_{4h}$ | 3551(13) | 4848(7) | 3070(11) | 115(6) |
| $O_{1i}$ | 1391(7) | 1752(4) | −1377(4) | 80(2) |
| $C_{1i}$ | 2235(19) | 1594(11) | −1998(13) | 160(8) |
| $C_{2i}$ | 2716(17) | 2287(14) | −2337(15) | 165(10) |
| $C_{3i}$ | 1991(28) | 2906(11) | −1934(14) | 204(12) |
| $C_{4i}$ | 1010(16) | 2533(7) | −1523(9) | 128(6) |
| $O_{1j}$ | 3037(5) | 155(4) | −264(5) | 72(2) |
| $C_{1j}$ | 4389(10) | 48(7) | 427(9) | 113(5) |
| $C_{2j}$ | 4998(16) | −571(10) | −23(16) | 174(8) |
| $C_{3j}$ | 4001(11) | −840(8) | −1006(10) | 127(6) |
| $C_{4j}$ | 2728(11) | −493(7) | −974(8) | 92(4) |

[a]The numbers in parentheses are the estimated standard deviations in the last significant digit.
[b]Atoms are labeled in agreement with FIGS. 5 and 6.
[c]This is one-third of the trace of the orthogonalized $B_{ij}$ tensor.

TABLE XII

Anisotropic Thermal Parameters for Nonhydrogen Atoms in Crystalline $[Cr(NC_4H_4)_5(OC_4H_8)][Na]_2\cdot 4(OC_4H_8)$[a]

| Atom Type[c] | Anisotropic Thermal Parameter (Å² × 10) | | | | | |
|---|---|---|---|---|---|---|
| | $B_{11}$ | $B_{22}$ | $B_{33}$ | $B_{12}$ | $B_{13}$ | $B_{23}$ |
| Anion | | | | | | |
| Cr | 29(1) | 31(1) | 38(1) | 1(1) | 12(1) | 1(1) |
| $N_{1a}$ | 33(2) | 44(3) | 44(3) | −1(2) | 11(2) | 5(2) |
| $C_{1a}$ | 48(4) | 37(3) | 59(4) | −0(3) | 15(3) | 3(3) |
| $C_{2a}$ | 55(4) | 61(5) | 90(5) | −19(4) | 34(4) | 13(4) |
| $C_{3a}$ | 37(3) | 82(6) | 76(5) | −9(3) | 33(3) | 2(4) |
| $C_{4a}$ | 40(3) | 64(5) | 52(4) | 4(3) | 16(3) | −5(3) |
| $N_{1b}$ | 36(2) | 44(3) | 36(3) | 7(2) | 5(2) | 12(2) |
| $C_{1b}$ | 52(4) | 51(4) | 40(3) | −1(3) | 9(3) | 10(3) |
| $C_{2b}$ | 73(5) | 85(6) | 83(6) | 2(5) | 13(4) | 44(5) |
| $C_{3b}$ | 51(4) | 88(6) | 54(4) | 0(4) | −13(3) | 12(4) |
| $c_{4b}$ | 41(3) | 55(4) | 45(3) | 0(3) | 5(2) | 4(4) |
| $N_{1c}$ | 33(2) | 41(3) | 39(3) | 4(2) | 9(2) | 1(2) |
| $C_{1c}$ | 52(4) | 51(4) | 51(4) | 6(3) | 16(3) | 5(3) |
| $C_{2c}$ | 64(5) | 62(5) | 37(3) | −1(4) | −4(3) | 4(4) |
| $C_{3c}$ | 32(3) | 92(6) | 89(6) | 4(4) | −3(4) | 29(5) |
| $C_{4c}$ | 42(3) | 78(5) | 48(3) | −1(3) | 9(3) | 14(4) |
| $N_{1d}$ | 31(2) | 44(3) | 56(3) | 4(2) | 13(2) | −1(3) |

TABLE XII-continued

Anisotropic Thermal Parameters for Nonhydrogen Atoms in Crystalline $[Cr(NC_4H_4)_5(OC_4H_8)][Na]_2\cdot 4(OC_4H_8)$[a]

| Atom Type[c] | Anisotropic Thermal Parameter ($Å^2 \times 10$) | | | | | |
|---|---|---|---|---|---|---|
| | $B_{11}$ | $B_{22}$ | $B_{33}$ | $B_{12}$ | $B_{13}$ | $B_{23}$ |
| $C_{1d}$ | 44(3) | 60(5) | 39(4) | −5(3) | 8(3) | −11(3) |
| $C_{2d}$ | 63(4) | 70(6) | 84(6) | −11(4) | 20(4) | −47(5) |
| $C_{3d}$ | 69(4) | 43(4) | 73(5) | 9(3) | 32(4) | −14(4) |
| $C_{4d}$ | 42(3) | 53(4) | 63(4) | 8(3) | 17(3) | 3(4) |
| $N_{1e}$ | 47(3) | 36(3) | 39(3) | −3(2) | 17(2) | −7(2) |
| $C_{1e}$ | 59(4) | 49(4) | 53(4) | −15(3) | 11(3) | −1(4) |
| $C_{2e}$ | 92(5) | 48(4) | 69(5) | −20(4) | 36(4) | −26(4) |
| $C_{3e}$ | 91(6) | 45(5) | 106(7) | 4(4) | 37(5) | −13(5) |
| $C_{4e}$ | 62(4) | 23(5) | 69(5) | 7(3) | 20(4) | −7(3) |
| $O_{1f}$ | 40(2) | 42(2) | 51(2) | −4(2) | 20(2) | 2(2) |
| $C_{1f}$ | 61(4) | 64(5) | 60(4) | −2(3) | 39(3) | 4(4) |
| $C_{2f}$ | 81(6) | 95(7) | 144(8) | −24(5) | 74(6) | 1(6) |
| $C_{3f}$ | 109(7) | 80(6) | 177(7) | −26(5) | 75(6) | −3(6) |
| $C_{4f}$ | 61(4) | 53(4) | 85(5) | −27(4) | 30(4) | −16(4) |
| Cation 1 | | | | | | |
| $Na_1$ | 57(2) | 71(2) | 95(2) | −13(1) | 21(2) | −2(2) |
| Cation 2 | | | | | | |
| $Na_2$ | 68(2) | 69(2) | 56(2) | −2(1) | 30(1) | −3(2) |
| Solvent Molecules of Crystallization | | | | | | |
| $O_{1g}$ | 58(3) | 95(4) | 92(4) | −8(3) | 15(3) | −2(4) |
| $C_{1g}$ | 54(5) | 215(14) | 108(8) | 0(7) | 29(5) | −7(9) |
| $C_{2g}$ | 96(7) | 226(15) | 121(9) | 52(9) | 43(7) | 51(10) |
| $C_{3g}$ | 129(10) | 277(19) | 148(11) | 52(12) | −56(9) | −134(13) |
| $C_{4g}$ | 134(10) | 250(18) | 128(10) | 44(11) | 39(9) | −89(11) |
| $O_{1h}$ | 71(4) | 68(4) | 152(6) | −8(3) | 32(4) | −3(4) |
| $C_{1h}$ | 92(7) | 95(8) | 144(9) | −2(6) | 28(7) | −3(7) |
| $C_{2h}$ | 212(14) | 108(9) | 140(10) | 36(10) | 50(10) | 66(9) |
| $C_{3h}$ | 99(8) | 175(14) | 101(8) | −6(9) | −2(6) | 32(9) |
| $C_{4h}$ | 99(8) | 79(7) | 168(10) | −13(6) | 38(8) | 29(8) |
| $O_{1i}$ | 98(4) | 82(4) | 73(3) | 8(3) | 47(3) | 13(3) |
| $C_{1i}$ | 230(15) | 128(11) | 168(12) | 8(11) | 131(12) | 74(10) |
| $C_{2i}$ | 112(10) | 222(21) | 156(15) | 1(12) | 28(10) | 23(16) |
| $C_{3i}$ | 370(26) | 124(12) | 135(12) | −93(15) | 99(15) | 34(10) |
| $C_{4i}$ | 223(13) | 81(7) | 106(8) | 32(8) | 91(9) | 31(6) |
| $O_{1j}$ | 59(3) | 64(3) | 94(4) | 5(3) | 22(3) | −21(3) |
| $C_{1j}$ | 88(7) | 101(8) | 133(9) | 19(6) | 2(6) | −58(7) |
| $C_{2j}$ | 94(8) | 190(14) | 205(13) | 73(10) | −11(9) | −90(13) |
| $C_{3j}$ | 83(7) | 130(10) | 160(10) | 16(7) | 20(7) | −86(9) |
| $C_{4j}$ | 82(6) | 104(8) | 92(7) | −7(6) | 29(5) | −41(6) |

[a]The numbers in parentheses are the estimated standard deviations in the last significant digit.
[b]The form of the anisotropic thermal parameter is given in reference 8 on page 6 of the structure report.
[c]Atoms are labeled in agreement with FIGS. 5 and 6.

TABLE XIII

Atomic Coordinates for Hydrogen Atoms in Crystalline $[Cr(NC_4H_4)_5(OC_4H_8)][Na]_2\cdot 4(OC_4H_8)$[a]

| Atom Type[b] | Fractional Coordinates | | |
|---|---|---|---|
| | $10^4 x$ | $10^4 y$ | $10^4 z$ |
| Anion | | | |
| $H_{1a}$ | 1061 | 3165 | 1756 |
| $H_{2a}$ | 3182 | 3406 | 1151 |
| $H_{3a}$ | 4547 | 2153 | 1428 |
| $H_{4a}$ | 3162 | 1162 | 2059 |
| $H_{1b}$ | 637 | 254 | 4479 |
| $H_{2b}$ | 2692 | 174 | 6022 |
| $H_{3b}$ | 4453 | 1179 | 5753 |
| $H_{4b}$ | 3373 | 1775 | 4016 |
| $H_{1c}$ | −326 | 2281 | 132 |
| $H_{2c}$ | −2637 | 2453 | −1199 |
| $H_{3c}$ | −4426 | 2031 | −243 |
| $H_{4c}$ | −3137 | 1655 | 1623 |
| $H_{1d}$ | 1070 | 2197 | 4997 |
| $H_{2d}$ | 349 | 3499 | 5480 |
| $H_{3d}$ | −1115 | 4135 | 3762 |
| $H_{4d}$ | −1278 | 3184 | 2317 |
| $H_{1e}$ | −1346 | 578 | 293 |
| $H_{2e}$ | −630 | −712 | −243 |
| $H_{3e}$ | 1503 | −1135 | 1285 |
| $H_{4e}$ | 1999 | −107 | 2676 |
| $H_{1fa}$ | −1447 | 1250 | 4520 |
| $H_{1fb}$ | −2359 | 1762 | 3588 |

TABLE XIII-continued

Atomic Coordinates for Hydrogen Atoms in Crystalline $[Cr(NC_4H_4)_5(OC_4H_8)][Na]_2\cdot 4(OC_4H_8)$[a]

| Atom Type[b] | Fractional Coordinates | | |
|---|---|---|---|
| | $10^4 x$ | $10^4 y$ | $10^4 z$ |
| $H_{2fa}$ | −4069 | 899 | 3170 |
| $H_{2fb}$ | −3468 | 674 | 4380 |
| $H_{3fa}$ | −2341 | −312 | 4022 |
| $H_{3fb}$ | −3620 | −314 | 2996 |
| $H_{4fa}$ | −2417 | 184 | 1980 |
| $H_{4fb}$ | −1165 | −201 | 2831 |
| Solvent of Crystallization | | | |
| $H_{1ga}$ | 6103 | 3536 | 4135 |
| $H_{1gb}$ | 5503 | 2694 | 3909 |
| $H_{2ga}$ | 6629 | 2283 | 5371 |
| $H_{2gb}$ | 7629 | 2940 | 5209 |
| $H_{3ga}$ | 6644 | 2947 | 6766 |
| $H_{3gb}$ | 7102 | 3717 | 6322 |
| $H_{4ga}$ | 4960 | 4045 | 5839 |
| $H_{4gb}$ | 4493 | 3223 | 6118 |
| $H_{1ha}$ | 596 | 4950 | 2301 |
| $H_{1hb}$ | 921 | 5310 | 3451 |
| $H_{2ha}$ | 2205 | 6231 | 3073 |
| $H_{2hb}$ | 1449 | 6034 | 1874 |
| $H_{3ha}$ | 3066 | 5447 | 1684 |
| $H_{3hb}$ | 3908 | 5936 | 2669 |
| $H_{4ha}$ | 4260 | 4953 | 3725 |
| $H_{4hb}$ | 3874 | 4459 | 2671 |
| $H_{1ia}$ | 3007 | 1289 | −1594 |
| $H_{1ib}$ | 1721 | 1306 | −2615 |
| $H_{2ia}$ | 3703 | 2328 | −2031 |
| $H_{2ib}$ | 2496 | 2303 | −3103 |
| $H_{3ia}$ | 1541 | 3249 | −2509 |
| $H_{3ib}$ | 2638 | 3195 | −1381 |
| $H_{4ia}$ | 101 | 2580 | −2020 |
| $H_{4ib}$ | 1010 | 2761 | −851 |
| $H_{1ja}$ | 4929 | 513 | 470 |
| $H_{1jb}$ | 4341 | −91 | 1129 |
| $H_{2ja}$ | 5823 | −388 | −178 |
| $H_{2jb}$ | 5232 | −992 | 479 |
| $H_{3ja}$ | 3930 | −1396 | −1018 |
| $H_{3jb}$ | 4261 | −668 | −1623 |
| $H_{4ja}$ | 2185 | −862 | −715 |
| $H_{4jb}$ | 2215 | −324 | −1678 |

[a]Hydrogen atoms were included in the structure factor calculations as idealized atoms (assuming $sp^2$- or $sp^3$-hybridization of the carbon atoms and a C—H bond length of 0.96Å) "riding" on their respective carbon atoms. The isotropic thermal parameter of each hydroigen atom was fixed at 1.2 times the equivalent isotropic thermal parameter of the carbon atom to which it is covalently bonded.
[b]Hydrogen atoms are labeled with the same numerical and literal subscripts as their carbon atoms with an additional literal subscript (a, or b) where necessary to distinguish between hydrogen atoms bonded to the same carbon.

TABLE XIV

Bond Lengths Involving Nonhydrogen Atoms in Crystalline $[Cr(NC_4H_4)_5(OC_4H_8)][Na]_2\cdot 4(OC_4H_8)$[a]

| Type[b] | Length, Å | Type[b] | Length, Å |
|---|---|---|---|
| $Cr—N_{1a}$ | 2.035(6) | $Na_1—O_{1g}$ | 2.314(6) |
| $Cr—N_{1b}$ | 2.056(5) | $Na_1—O_{1h}$ | 2.271(8) |
| $Cr—N_{1c}$ | 2.044(5) | | |
| $Cr—N_{1d}$ | 2.114(6) | $Na_2—O_{1i}$ | 2.365(7) |
| $Cr—N_{1e}$ | 2.024(6) | $Na_2—O_{1j}$ | 2.365(7) |
| $Cr—O_{1f}$ | 2.120(5) | $C_{1g}—C_{2g}$ | 1.33(2) |
| | | $C_{2g}—C_{3g}$ | 1.43(2) |
| $N_{1a}—C_{1a}$ | 1.36(1) | $C_{3g}—C_{4g}$ | 1.47(2) |
| $N_{1a}—C_{4a}$ | 1.38(1) | $C_{1h}—C_{2h}$ | 1.51(2) |
| $N_{1b}—C_{1b}$ | 1.33(1) | $C_{2h}—C_{3h}$ | 1.30(2) |
| $N_{1b}—C_{4b}$ | 1.37(1) | $C_{3h}—C_{4h}$ | 1.48(2) |
| $N_{1c}—C_{1c}$ | 1.41(1) | $C_{1i}—C_{2i}$ | 1.41(3) |
| $N_{1c}—C_{4c}$ | 1.35(1) | $C_{2i}—C_{3i}$ | 1.47(3) |
| $N_{1d}—C_{1d}$ | 1.34(1) | $C_{3i}—C_{4i}$ | 1.40(3) |
| $N_{1d}—C_{4d}$ | 1.36(1) | $C_{1j}—C_{2j}$ | 1.44(2) |
| $N_{1e}—C_{1e}$ | 1.40(1) | $C_{2j}—C_{3j}$ | 1.46(2) |
| $N_{1e}—C_{4e}$ | 1.39(1) | $C_{3j}—C_{4j}$ | 1.42(2) |
| $O_{1f}—C_{1f}$ | 1.42(1) | $C_{1g}—C_{1g}$ | 1.38(1) |
| $O_{1f}—C_{4f}$ | 1.44(1) | $O_{1g}—C_{4g}$ | 1.32(2) |
| | | $O_{1h}—C_{1h}$ | 1.38(1) |
| $C_{1a}—C_{2a}$ | 1.39(1) | $O_{1h}—C_{4h}$ | 1.39(2) |
| $C_{2a}—C_{3a}$ | 1.38(1) | $O_{1i}—C_{1i}$ | 1.36(2) |

TABLE XIV-continued

Bond Lengths Involving Nonhydrogen Atoms in Crystalline $[Cr(NC_4H_4)_5(OC_4H_8)][Na]_2\cdot 4(OC_4H_8)^a$

| Type[b] | Length, Å | Type[b] | Length, Å |
|---|---|---|---|
| $C_{3a}$—$C_{4a}$ | 1.37(1) | $O_{1i}$—$C_{4i}$ | 1.40(1) |
| $C_{1b}$—$C_{2b}$ | 1.33(1) | $O_{1j}$—$C_{1j}$ | 1.41(1) |
| $C_{2b}$—$C_{3b}$ | 1.42(1) | $O_{1j}$—$C_{4j}$ | 1.43(1) |
| $C_{3b}$—$C_{4b}$ | 1.31(1) | | |
| $C_{1c}$—$C_{2c}$ | 1.37(1) | $Na_1$—$C_{1a}$ | 2.678(8) |
| $C_{2c}$—$C_{3c}$ | 1.41(1) | $Na_1$—$N_{1d}$ | 2.688(7) |
| $C_{3c}$—$C_{4c}$ | 1.39(1) | $Na_1$—$C_{1d}$ | 2.621(9) |
| $C_{1d}$—$C_{2d}$ | 1.37(1) | | |
| $C_{2d}$—$C_{3d}$ | 1.40(1) | | |
| $C_{3d}$—$C_{4d}$ | 1.34(1) | $Na_2$—$C_{4a}$ | 2.681(7) |
| $C_{1e}$—$C_{2e}$ | 1.37(1) | $Na_2$—$C_{1e}$ | 2.630(9) |
| $C_{2e}$—$C_{3e}$ | 1.43(1) | | |
| $C_{3e}$—$C_{4e}$ | 1.37(1) | | |
| $C_{1f}$—$C_{2f}$ | 1.50(1) | | |
| $C_{2f}$—$C_{3f}$ | 1.43(2) | | |
| $C_{3f}$—$C_{4f}$ | 1.49(2) | | |

[a] The numbers in parentheses are the estimated standard deviations in the last significant digit.
[b] Atoms are labeled in agreement with FIG. 6.

TABLE XV

Bond Angles Involving Nonhydrogen Atoms in Crystalline $[Cr(NC_4H_4)_5(OC_4H_8)][Na]_2\cdot 4(OC_4H_8)^a$

| Type[b] | Angle, deg | Type[b] | Angle, deg |
|---|---|---|---|
| $N_{1a}CrN_{1b}$ | 91.2(2) | $O_{1g}Na_1O_{1h}$ | 92.3(3) |
| $N_{1a}CrN_{1c}$ | 91.4(2) | $O_{1g}Na_1C_{1a}$ | 114.3(3) |
| $N_{1a}CrN_{1d}$ | 91.1(2) | $O_{1g}Na_1N_{1d}$ | 139.6(3) |
| $N_{1a}CrN_{1e}$ | 92.8(2) | $O_{1g}Na_1C_{1d}$ | 118.0(3) |
| $N_{1a}CrO_{1f}$ | 178.7(2) | $O_{1h}Na_1C_{1a}$ | 95.6(3) |
| $N_{1b}CrN_{1c}$ | 176.2(2) | $O_{1h}Na_1N_{1d}$ | 127.0(2) |
| $N_{1b}CrN_{1d}$ | 86.7(2) | $O_{1h}Na_1C_{1d}$ | 132.1(3) |
| $N_{1b}CrN_{1e}$ | 93.3(2) | $C_{1a}Na_1N_{1d}$ | 75.1(2) |
| $N_{1b}CrO_{1f}$ | 88.5(2) | $C_{1a}Na_1C_{1d}$ | 103.1(3) |
| $N_{1c}CrN_{1d}$ | 90.4(2) | $N_{1d}Na_1C_{1d}$ | 29.3(2) |
| $N_{1c}CrN_{1e}$ | 89.4(2) | | |
| $N_{1c}CrO_{1f}$ | 88.8(2) | $O_{1i}Na_2O_{1j}$ | 90.7(3) |
| $N_{1d}CrN_{1e}$ | 176.1(2) | $O_{1i}Na_2C_{4a}$ | 109.3(3) |
| $N_{2d}CrO_{1f}$ | 87.6(2) | $O_{1i}Na_2C_{1e}$ | 131.5(2) |
| $N_{1e}CrO_{1f}$ | 88.5(2) | $O_{1j}Na_2C_{4a}$ | 103.2(2) |
| | | $O_{1j}Na_2C_{1e}$ | 115.1(3) |
| $CrN_{1a}C_{1a}$ | 128.7(5) | $C_{4a}Na_2C_{1e}$ | 103.9(3) |
| $CrN_{1a}C_{4a}$ | 126.3(5) | | |
| $CrN_{1b}C_{1b}$ | 127.0(4) | $Na_1O_{1g}C_{1g}$ | 131.4(6) |
| $CrN_{1b}C_{4b}$ | 127.3(5) | $Na_1O_{1g}C_{4g}$ | 124.0(8) |
| $CrN_{1c}C_{1c}$ | 128.5(5) | $Na_1O_{1h}C_{1h}$ | 132.2(7) |
| $CrN_{1c}C_{4c}$ | 126.7(5) | $Na_1O_{1h}C_{4h}$ | 116.6(6) |
| $CrN_{1d}C_{1d}$ | 127.7(5) | $Na_2O_{1i}C_{1i}$ | 120.9(8) |
| $CrN_{1d}C_{4d}$ | 125.7(5) | $Na_2O_{1i}C_{4i}$ | 126.8(7) |
| $CrN_{1e}C_{1e}$ | 127.7(5) | $Na_2O_{1j}C_{1j}$ | 123.1(6) |
| $CrN_{1e}C_{4e}$ | 126.2(4) | $Na_2O_{1j}C_{4j}$ | 125.8(5) |
| $CrO_{1f}C_{1f}$ | 126.4(4) | $C_{1g}O_{1g}C_{4g}$ | 104.3(8) |
| $CrO_{1f}C_{4f}$ | 123.1(5) | $C_{1h}O_{1h}C_{4h}$ | 108.9(9) |
| | | $C_{1i}O_{1i}C_{4i}$ | 107.8(11) |
| $C_{1a}N_{1a}C_{4a}$ | 105.0(6) | $C_{1j}O_{1j}C_{4j}$ | 107.7(7) |
| $C_{1b}N_{1b}C_{4b}$ | 105.2(5) | | |
| $C_{1c}N_{1c}C_{4c}$ | 104.0(5) | $O_{1g}C_{1g}C_{2g}$ | 111(1) |
| $C_{1d}N_{1d}C_{4d}$ | 106.6(6) | $C_{1g}C_{2g}C_{3g}$ | 103(1) |
| $C_{1e}N_{1e}C_{4e}$ | 106.0(6) | $C_{2g}C_{3g}C_{4g}$ | 103(1) |
| | | $C_{3g}C_{4g}O_{1g}$ | 110(1) |
| $C_{1f}O_{1f}C_{4f}$ | 110.5(6) | $O_{1h}C_{1h}C_{2h}$ | 106(1) |
| | | $C_{1h}C_{2h}C_{3h}$ | 106(1) |
| $N_{1a}C_{1a}C_{2a}$ | 111.1(7) | $C_{2h}C_{3h}C_{4h}$ | 109(1) |
| $C_{1a}C_{2a}C_{3a}$ | 106.1(8) | $C_{3h}C_{4h}O_{1h}$ | 106(1) |
| $C_{2a}C_{3a}C_{4a}$ | 107.5(7) | $O_{1i}C_{1i}C_{2i}$ | 110(2) |
| $C_{3a}C_{4a}N_{1a}$ | 110.3(7) | $C_{1i}C_{2i}C_{3i}$ | 105(2) |
| $N_{1b}C_{1b}C_{2b}$ | 110.6(7) | $C_{2i}C_{3i}C_{4i}$ | 106(2) |
| $C_{1b}C_{2b}C_{3b}$ | 107.6(8) | $C_{3i}C_{4i}O_{1i}$ | 107(1) |
| $C_{2b}C_{3b}C_{4b}$ | 104.4(7) | $C_{1j}C_{1j}C_{2j}$ | 106(1) |
| $C_{3b}C_{4b}N_{1b}$ | 112.2(7) | $C_{1j}C_{2j}C_{3j}$ | 109(1) |
| $N_{1c}C_{1c}C_{2c}$ | 112.4(7) | $C_{2j}C_{3j}C_{4j}$ | 104(1) |
| $C_{1c}C_{2c}C_{3c}$ | 104.5(7) | $C_{3j}C_{4j}O_{1j}$ | 108(1) |
| $C_{2c}C_{3c}C_{4c}$ | 107.8(7) | | |
| $C_{3c}C_{4c}N_{1c}$ | 111.2(7) | $Na_1C_{1a}N_{1a}$ | 95.0(4) |
| $N_{1d}C_{1d}C_{2d}$ | 109.0(7) | $Na_1C_{1a}N_{1a}$ | 106.7(5) |
| $C_{1d}C_{2d}C_{3d}$ | 107.6(8) | $Na_1N_{1d}Cr$ | 107.7(3) |
| $C_{2d}C_{3d}C_{4d}$ | 105.4(8) | $Na_1N_{1d}C_{1d}$ | 72.6(4) |
| $C_{3d}C_{4d}N_{1d}$ | 111.5(7) | $Na_1N_{1d}C_{4d}$ | 86.4(4) |
| $N_{1e}C_{1e}C_{2e}$ | 111.0(7) | $Na_1C_{1d}N_{1d}$ | 78.1(4) |
| $C_{1e}C_{3e}C_{4e}$ | 105.2(7) | $Na_1C_{1d}C_{2d}$ | 85.1(6) |
| $C_{2e}C_{3e}C_{4e}$ | 108.4(8) | | |
| $C_{3e}C_{4e}N_{1e}$ | 109.5(7) | $Na_2C_{4a}N_{1a}$ | 90.2(3) |
| | | $Na_2C_{4a}C_{3a}$ | 104.0(5) |
| $O_{1j}C_{1j}C_{2f}$ | 104.4(7) | $Na_2C_{1e}N_{1e}$ | 78.1(4) |
| $C_{1j}C_{2j}C_{3f}$ | 105.0(9) | $Na_2C_{1e}N_{1e}$ | 78.1(4) |
| $C_{2j}C_{3j}C_{4f}$ | 104.9(9) | | |
| $C_{3j}C_{4j}O_{1f}$ | 104.7(7) | | |

[a] The numbers in parentheses are the estimated standard deviations in the last significant digit.
[b] Atoms are labeled in agreement with FIG. 6.

EXAMPLE VII

The product obtained from the reaction of sodium 2,5-dimethylpyrrolide and CrCl$_2$ used in the preparation of an active catalyst was a light blue solid, Product VI. 2,5-Dimethylpyrrole (5.0 ml/49.1 mmole) was mixed with excess sodium (40% dispersion in mineral spirits) in tetrahydrofuran (125 ml) at ambient temperature. The mixture was refluxed 12 hours under nitrogen then filtered to remove excess sodium. The sodium 2,5-dimethylpyrrolide was used in-situ and combined with chromous chloride (3.03 g/24.7 mmole) at ambient temperature. The reaction mixture was refluxed under nitrogen for 48 hours. The gray-green solution was filtered (medium porosity frit) at ambient temperature and stripped of solvent under vacuum, then pumped dry under vacuum for 12 hours resulting in a gray/green solid. This gray/green solid was then washed with pentane resulting in a light blue solid, Product VI, which was collected by filtration. Product VI was used in the preparation of an active catalyst without further purification.

EXAMPLE VIII

Preparation of Catalysts

All polymerization runs were carried out in a two liter reactor under slurry (particle form) conditions. The diluent was isobutane and the reactor temperature was 90° C. Reactor pressure held at 550 psig during the polymerization, with ethylene being fed on demand.

The actual charging of the reactor was accomplished by the following method. After purging the reactor at 100° C. with a stream of nitrogen for at least 15 minutes, the reactor temperature was lowered to 90° C. and a preweighed amount of supported chromium pyrrolide catalyst was charged against a slight countercurrent of nitrogen. One liter of isobutane was then charged to the reactor and finally the reactor pressurized with ethylene.

The ethylene consumed was determined using a pre-calibrated ethylene flow meter. Samples of the liquid product mixture were taken after 30 minute run time without depressurizing the reactor. This was done by filling to 200–300 psig a steel sampling cylinder adapted to the reactor with a dip tube fitted with a fritted tip extending into the bottom of the reactor vessel. Samples taken this way were analyzed by gas chromatography and gas chromatography-mass spectrometry. Selectivities were normalized to 100%. Solid products were obtained by venting the reactor to atmosphere, separating by decantation of the liquids from the solid material. The solids were then dried at 100° C. in a vacuum oven and weighed. The yield of solid product was obtained by weighing the combined solid and catalyst residues and subtracting from this the preweighed catalyst charge. The yield of volatile products was obtained by subtracting the yield of solid products from the grams of ethylene consumed as recorded by the flow meter.

Activity typically ranged from 300-1500 g product/g catalyst/hour calculated for 30 minute run time, as shown in Table XVI. The product obtained typically was represented by 97-99.5% by weight liquids and 0.5-3% by weight polymer (wax). The liquid fraction was typically 85% hexenes, 11% decenes, 2% tetradecences, based on the total weight of the liquid fraction. The balance of the liquid product mixture was a trace level distribution of olefins typically totaling about 1-2% by weight of the product mixture, see Table XVII.

Active catalysts were prepared from the chromium pyrrolide complexes as follows. All toluene and/or pentane rinses used about 15 to about 30 mls of liquid.

Run 1: 0.158 g of Product V (prepared in THF solvent), which was heated to 80° C. for 4 hours under nitrogen flush to remove residual THF, was slurried with 15 ml toluene at ambient temperature. 9.0 ml of a 1M TEA in hexanes solution was added to the solution and stirred for 24 hours. The formation of a brown solution and the complete dissolution of Product V resulted immediately upon TEA addition. $AlPO_4$(P/Al mole ratio=0.4) (2.00 g) was added to the solution and stirred for an additional 24 hours. The supported catalyst was filtered from the solution as a brown solid, rinsed twice with toluene, and then twice with pentane. 0.3143 g of the catalyst was charged directly to the reactor for polymerization. 1.0 ml of a 0.5% TEA in heptanes solution was charged to the reactor after the catalyst charge but before the isobutane (reactor solvent) charge to purge feedstock poisons.

Run 2: 0.081 g of Product V (prepared in THF solvent), which was heated to 80° C. for 4 hours under nitrogen flush to remove residual THF, was slurtied with 15 ml diethylbenzene at ambient temperature. 2.0 ml of a 1M TEA in hexanes solution was added to the solution and stirred for 24 hours. The formation of a brown solution and the complete dissolution of Product V resulted immediately upon TEA addition. $AlPO_4$(P/Al mole ratio=0.4) (1.50 g) was added to the solution and stirred for an additional 1 hour. The supported catalyst was filtered from the solution as a brown solid, rinsed twice with dimethylbenzene, and then twice with pentane. 0.4333 g of the catalyst was charged directly to the reactor for polymerization. 3.0 ml of a 0.5% TEA in heptanes solution was charged to the reactor after the catalyst charge but before the isobutane (reactor solvent) charge to purge feedstock poisons.

Run 3: 0.093 g of Product V (prepared in DME solvent) was slurried with 15 ml toluene at ambient temperature. 5.0 ml of a 1M TEA in hexanes solution was added to the solution and stirred for 24 hours. The formation of a brown solution and the complete dissolution of Product V resulted immediately upon TEA addition. $AlPO_4$(P/Al mole ratio=0.4) (1.0 g) was added to the solution and stirred for an additional 24 hours. The supported catalyst was filtered from the solution as a brown solid, rinsed twice with toluene, and then twice with pentane. 0.1564 g of the catalyst was charged directly to the reactor for polymerization. 3.0 ml of a 0.5% TEA in heptanes solution was charged to the reactor after the catalyst charge but before the isobutane (reactor solvent) charge to purge feedstock poisons.

Run 4: 0.080 g of Product I (prepared in THF solvent) was slurried with 15 ml toluene at ambient temperature. 6.0 ml of a 1M TEA in hexanes solution was added and the solution stirred for 16 hours. The formation of a brown solution and the complete dissolution of Product I resulted immediately upon TEA addition. $AlPO_4$(P/Al mole ratio=0.4) (1.50 g) was added to the solution and stirred for an additional 16 hours. The supported catalyst was filtered from the solution as a brown solid, rinsed twice with toluene, and then rinsed twice pentane. 1.1988 g of the catalyst was charged directly to the reactor for polymerization.

Run 5: 0.079 g of Product II (prepared in THF solvent) was slurried with 15 ml toluene at ambient temperature. 2.0 ml of a 1.9M TEA in toluene solution was added to the solution and stirred for 8 hours. The formation of a brown solution and the complete dissolution of Product II resulted immediately upon TEA addition. $AlPO_4$(P/Al mole ratio=0.4) (0.50 g) was added to the solution and stirred for an additional 16 hours. The supported catalyst was filtered from the solution as a brown solid, rinsed twice with toluene, and then twice with pentane. 0.4829 g of the catalyst was charged directly to the reactor for polymerization.

Run 6: 0.071 g of Product V (prepared in THF solvent), which was heated to 80° C. for 4 hours under nitrogen flush to remove residual THF, was slurried with 15 ml toluene at ambient temperature. 2.0 ml of a 1M TEA in hexanes solution was added to the solution and stirred for 1 hour. The formation of a brown solution and the complete dissolution of Product V resulted immediately upon TEA addition. $SiO_2$(2.52 g) was added to the solution and stirred for an additional 2 minutes. The supported catalyst was filtered from the solution as a brown solid, rinsed twice with toluene, and then twice with pentane. All of the catalyst was charged directly to the reactor for polymerization.

Run 7: 0.103 g of Product II (prepared in THF solvent) was slurried with 15 ml toluene at ambient temperature. 1.0 ml of a 1.9M TEA in toluene solution was added to the solution and stirred for 10 minutes. The formation of a brown solution and the complete dissolution of Product II resulted immediately upon TEA addition. $Al_2O_3$ (2.27 g) was added to the solution and stirred for an additional 2 minutes. The supported catalyst was filtered from the solution as a brown solid, rinsed twice with toluene, and then twice with pentane. 1.2926 g of the catalyst was charged directly to the reactor for polymerization.

Run 8: 0.120 g of Product I (prepared in THF solvent) was slurtied with 15 ml toluene at ambient temperature. 2.0 ml of a 1M TEA in hexanes solution was added to the solution and stirred for 2 days. The formation of a brown solution and the complete dissolution of Product I resulted immediately upon TEA addition. $SiO_2$(1.0 g) was added to the solution and stirred for an additional 3 weeks. The supported catalyst was filtered from the solution as a brown solid, rinsed twice with toluene, and then twice with pentane. All of the catalyst was charged directly to the reactor for polymerization.

Run 9: 0.106 g of Product III (prepared in THF solvent) was slurried with 15 ml toluene at ambient temperature. 2.5 ml of a 1.9M TEA in toluene solution was added to the solution and stirred for 2 hours. The formation of a brown solution and the complete dissolution of Product III resulted immediately upon TEA addition.

AlPO$_4$(P/Al mole ratio=0.4) (0.65 g) was added to the solution and stirred for an additional 2 hours. The supported catalyst was filtered from the solution as a brown solid, rinsed twice with toluene, and then twice with pentane. All of the catalyst was charged directly to the reactor for polymerization. 1.5 ml of a 1.0% TEA in pentane solution was charged to the reactor after the catalyst charge but before the isobutane (reactor solvent) charge to purge feedstock poisons.

Run 10: 0.030 g of Product V (prepared in THF solvent) which was heated to 80° C. for 4 hours under nitrogen flush to remove residual THF was slurried with 15 ml toluene at ambient temperature. 3.0 ml of a 1M TEA in hexanes solution was added to the solution and stirred for 16 hours. The formation of a brown solution and the complete dissolution of Product V resulted immediately upon TEA addition. AlPO$_4$(P/Al=0.9) (2.0 g) was added to the solution and stirred for an additional 16 hours. The supported catalyst was filtered from the solution as a brown solid, rinsed twice with toluene, and then twice with pentane. 0.322/g of catalyst was charged directly to the reactor for polymerization.

Run 11: 0.067 g of Product V (prepared in THF solvent) was slurried with 15 ml pentane at ambient temperature. 4.0 ml of a 1M TEA in hexanes solution was added to the solution and stirred for 24 hours. The formation of a brown solution and the complete dissolution of Product V resulted immediately upon TEA addition. AlPO$_4$(P/Al mole ratio=0.4) (1.0 g) was added to the solution and stirred for an additional 24 hours. The supported catalyst was filtered from the solution as a brown solid, rinsed twice with pentane. All of the catalyst was charged directly to the reactor for polymerization. 3.0 ml of a 0.5% TEA in heptanes solution was charged to the reactor after the catalyst charge but before the isobutane (reactor solvent) charge to purge feedstock poisons.

Run 12: 0.073 g of Product V (prepared in THF solvent), which was heated to 80° C. for 4 hours under nitrogen flush to remove residual THF, was slurried with 15 ml toluene at ambient temperature. 6.0 ml of a 1M TEA in hexanes solution was added and the solution stirred for 24 hours. The formation of a brown solution and the complete dissolution of Product V resulted immediately upon TEA addition. P/SiO$_2$ (7.0 g) was added to the solution and stirred for an additional 24 hours which nearly decolorized it. The supported catalyst was filtered from the solution as a brown solid, rinsed twice with toluene, and then twice with pentane. 2.85 g of catalyst was charged directly to the reactor for polymerization.

Run 13: 0.125 g or Product II was slurried with 15 ml diethylbenzene at ambient temperature. 9.0 ml of a 1M TEA in hexanes solution was added to the solution and stirred for 8 hours. The formation of a brown solution and the complete dissolution of Product II resulted immediately upon TEA addition. F/Al$_2$O$_3$ (2.0 g) was added to-the solution and stirred for an additional 12 hours. The supported catalyst was filtered from the solution as a brown solid, rinsed twice with toluene, and then twice with pentane. 0.5477 g of catalyst was charged directly to the reactor for polymerization.

Run 14: 0.125 g of Product VI was slurried with 15 ml toluene at ambient temperature. 1.5 ml of a 1M TEA in hexanes solution was added and the solution stirred for 10 minutes. The formation of a red/brown solution and the complete dissolution of Product VI resulted immediately upon TEA addition. SiO$_2$ (2.0 g) was added to the solution and stirred for an additional 1 minute which nearly decolorized it. The supported silica catalyst was filtered from the solution as a red/brown solid, rinsed twice with toluene, and then twice with pentane. All of the catalyst was charged directly to the reactor for polymerization.

Run 15: 0.30 g of Product V (prepared in DME solvent) was dissolved with 15 ml of dimethoxyethane forming a green solution. This solution was then mixed with 0.6 g of AlPO$_4$(P/Al$_4$ mole ratio=0.4) (2.00 g) and the mixture was stirred 1 hour. The green supported material was filtered from the solution, rinsed with dimethoxyethane and dried with a nitrogen purge at 90° C. This material was then stirred with 15 ml of toluene and 3 ml of triethylaluminum (Aldrich 1.0M, hexanes) for an additional 3 hours. The brown supported catalyst was collected by filtration, rinsed with pentane, and dried under vacuum. 0.4609 g of the catalyst was charged directly to the reactor for polymerization. 3.0 ml of a 0.5% TEA in heptanes solution was charged to the reactor after the catalyst charge but before the isobutane (reactor solvent) charge to purge feedstock poisons.

Run 16: 0.058 g of Product V (prepared in THF solvent) which was heated to 80° C. for 4 hours under nitrogen flush to remove residual THF was slurried with 15 ml benzene at ambient temperature. 4.0 ml of a 1M TEA in hexanes solution was added and the solution stirred for 2 hours. The formation of a brown solution and the complete dissolution of Product V resulted immediately upon TEA addition. AlPO$_4$(P/Al mole ratio=0.4) (1.0 g) was added to the solution and stirred for 1 hour. The supported catalyst was filtered from the solution as a brown solid, rinsed twice with benzene, and then twice with pentane. All of the catalyst was charged directly to the reactor for polymerization. 3.0 ml of a 0.5% TEA in heptanes solution was charged to the reactor after the catalyst charge but before the isobutane (reactor solvent) charge to purge feedstock poisons.

Run 17: 0.1610 g of Product I was charged directly to the reactor at 90° C. The reactor was charged with 1 liter isobutane and pressurized to 550 psig with ethylene. No ethylene consumption was detected, therefore 50 psig of dihydrogen (H$_2$) was charged to the reactor which did not initiate ethylene consumption. Ethylene consumption was initiated after 2.0 ml of 1M TEA in hexanes solution was charged.

Run 18: 0.3528 g of Product VI was charged directly to the reactor at 90° C. The reactor was charged with 1 liter isobutane and pressurized to 550 psig with ethylene. No ethylene consumption was detected, therefore 2.0 ml of a 1M TEA in hexanes solution was charged which did initiate ethylene consumption.

Run 19: 0.3482 g of Product VI was charged directly to the reactor at 90° C. The reactor was also charged with 2.0 ml of a 1M TEA in hexanes solution prior to a 1 liter isobutane charge. The reactor was then pressurized to 550 psig with ethylene. No ethylene consumption was detected, therefore 30 psi of dihydrogen was charged to the reactor which initiated ethylene consumption.

Run 20: 0.202 g of Product V (prepared in dimethoxyethane (DME) solvent), 6.0 ml of a 1.9M TEA in toluene solution, and 2.0 g of AlPO$_4$(P/Al mole ratio=0.4) were mixed with 15 ml toluene at ambient temperature. The formation of a brown solution and the complete dissolution of Product V resulted immediately upon mixing. The brown solution was stirred for 48 hours. The supported catalyst was filtered from the solution as a brown solid, rinsed twice with toluene, and then twice with pentane. 0.0671 g of the catalyst was charged directly to the reactor for polymerization. 1.0 ml of a 0.5% TEA in heptanes solution was charged to the reactor after the catalyst charge but before the isobutane (reactor solvent) charge to purge feedstock poisons.

The data in Table XVI show that the inventive chromium compounds can be used either supported (Runs 1–16, 20) or unsupported (Runs 17–19) to polymerize and/or trimerize olefins. Furthermore, conditions can be varied to increase the amount of trimer product (Runs 1–5 and 9) or to have a higher yield of solid, or polymer, product (Runs 6, 7, and 13). Runs 1, 3, and 20 demonstrate that high activities are attainable.

Shape: Rectangular parallelepiped
Dimensions: $0.44 \times 0.62 \times 0.62$ mm
Crystal Mount: Crystal was glued to the inside of a thin-walled glass capillary and sealed under $N_2$.
Crystal Orientation: Crystal was oriented with its longer edges nearly parallel to the phi axis of the diffractometer.
Width at Half-height from w Scans: $0.38°$
The space group and cell data are as follows:
Crystal System: Monoclinic
Space Group and Number: $P2_1/c$—$C_{2h}$ (No. 14)
Number of Computer-Centered Reflections Used in the Least-Squares Refinement of the Cell Dimensions: 15 20>25° °C.=20±1
Lattice Constants with esd's:
a=8.135(2)Å
b=22.337(5)Å
c=16.667(4)Å

TABLE XVI

| Run[a] | Catalyst | Support[b] | Products | Activity[c] |
|---|---|---|---|---|
| 1 | (V)/TEA/Toluene | AlPO$_4$ | 98.4% liquids, 1.6% solids | 1030 |
| 2 | (V)/TEA/Diethylbenzene | AlPO$_4$ | 99.4% liquids, 0.6% solids | 730 |
| 3 | (V)/TEA/Toluene | AlPO$_4$ | 99.4% liquids, 0.6% solids | 1450[d] |
| 4 | (I)/TEA/Toluene | AlPO$_4$ | 98.6% liquids, 1.4% solids | 360 |
| 5 | (II)/TEA/Toluene | AlPO$_4$ | 98.2% liquids, 1.8% solids | 580 |
| 6 | (V)/TEA/Toluene | SiO$_2$ | 89.0% liquids, 11.0% solids | 80 |
| 7 | (II)/TEA/Toluene | Al$_2$O$_3$ | 55.8% liquids, 44.2% solids | 50 |
| 8 | (I)/TEA/Toluene | SiO$_2$ | 93.3% liquids, 6.7% solids | 400 |
| 9 | (III)/TEA/Toluene | AlPO$_4$ | 99.8% liquids, 0.2% solids | 100 |
| 10 | (V)/TEA/Toluene | AlPO$_4$(.9) | 96.8% liquids, 3.2% solids | 930 |
| 11 | (V)/TEA/Pentane | AlPO$_4$ | (trace) liquids, (trace) solids | unreactive |
| 12 | (V)/TEA/Toluene | P/SiO$_2$ | 98.1% liquids, 1.9% solids | 90 |
| 13 | (II)/TEA/Diethylbenzene | F/Al$_2$O$_3$ | 88.0% liquids, 12.0% solids | 300 |
| 14 | (VI)/TEA/Toluene | SiO$_2$ | 94.3% liquids, 5.7% solids | 40 |
| 15 | (V)/DME | AlPO$_4$ | 98.0% liquids, 2.0% solids | 550 |
| 16 | (V)/TEA/Benzene | AlPO$_4$ | 99.1% liquids, 0.9% solids | 500 |
| 17 | (I)/TEA | unsupported | 98.3% liquids, 1.7% solids | 340 |
| 18 | (VI)/TEA | unsupported | 99.4% liquids, 0.6% solids | 180 |
| 19 | (VI)/TEA | unsupported | 98.1% liquids, 1.9% solids | 230 |
| 20 | (V)/TEA/Toluene | AlPO$_4$ | 99.5% liquids, 0.5% solids | 2760 |

[a]All runs were made at 90° C., isobutane solvent, 550 psi total pressure.
[b]P/Al mole ratio = 0.4; except Run 10 whereby P/Al mole ratio = 0.9.
[c]Grams product/grams catalyst/hour based on 30 min. run times.
[d]Believed to be lower than actual due to experimental error; actual value believe to be near 2000.

TABLE XVII

| Run | C4 | 1-hexene | C6 | C8 | C10 | C12 | C14 | C16–C28 |
|---|---|---|---|---|---|---|---|---|
| 1 | 0.05 | 81.92 | 7.76 | 0.49 | 9.12 | 0.09 | 0.52 | .05 |
| 2 | 0.10 | 78.80 | 7.49 | 0.58 | 11.36 | 0.10 | 1.01 | .56 |
| 3 | 0.06 | 82.19 | 7.68 | 0.45 | 8.85 | 0.08 | 0.58 | .11 |
| 5 | 0.10 | 83.40 | 7.08 | 0.62 | 8.08 | 0.05 | 0.42 | .25 |
| 6 | 0.55 | 78.70 | 5.52 | 1.84 | 11.24 | 0.42 | 1.26 | .47 |
| 16 | 0.06 | 72.85 | 13.61 | 0.31 | 12.06 | 0.09 | 0.93 | .09 |
| 19 | 6.03 | 71.66 | 6.09 | 3.61 | 9.42 | 1.17 | 1.41 | .61 |

EXAMPLE IX

Figure 7:
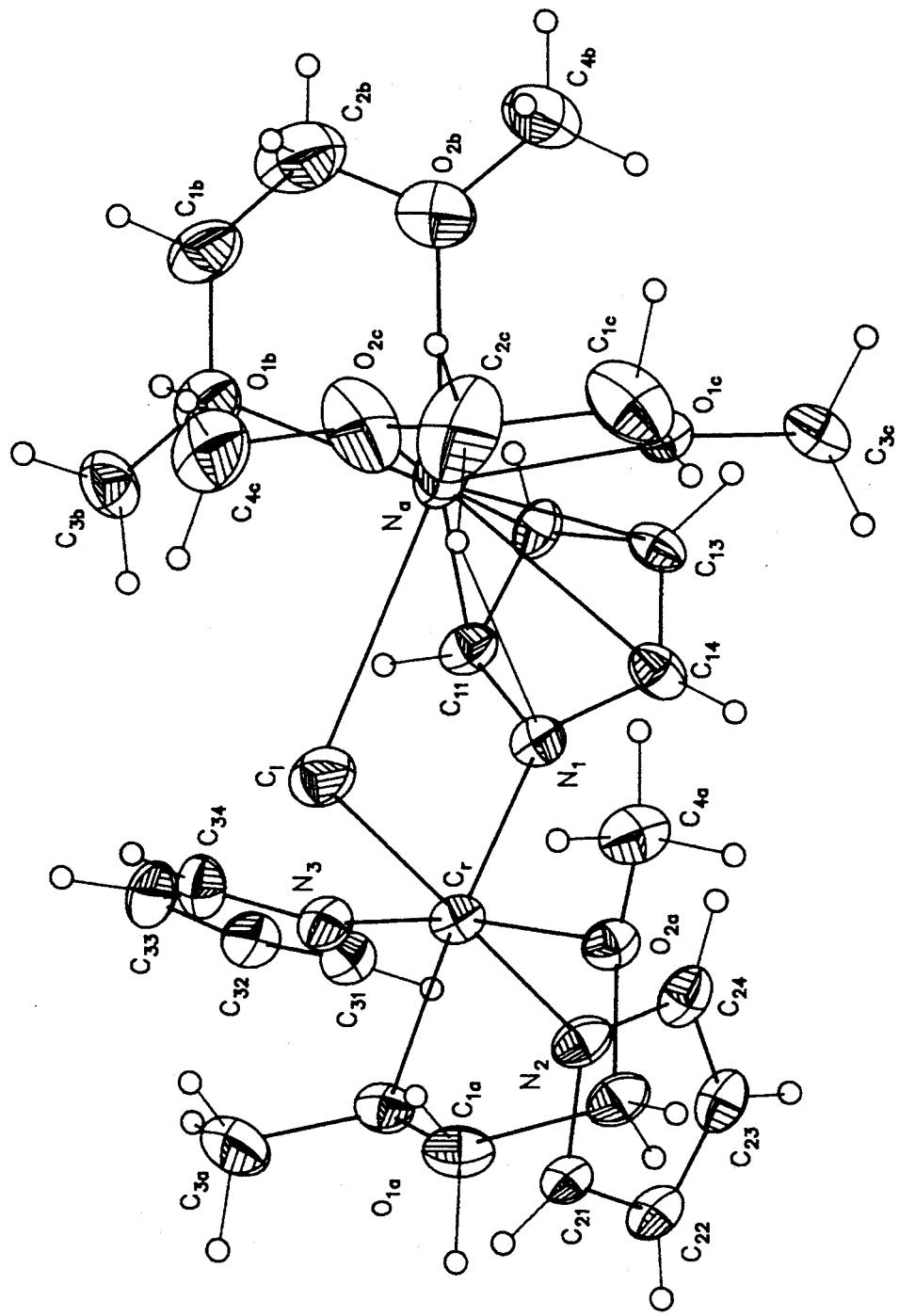
FIG. 7 is a computer generated ORTEP drawing of a molecule of Product V, $Cr(NC_4H_4)_3Cl(O_2C_2H_4(CH_4)_2)_4Na$, which includes the entire crystal structure or lattice, as determined by single crystal x-ray crystallography.
Figure 8:
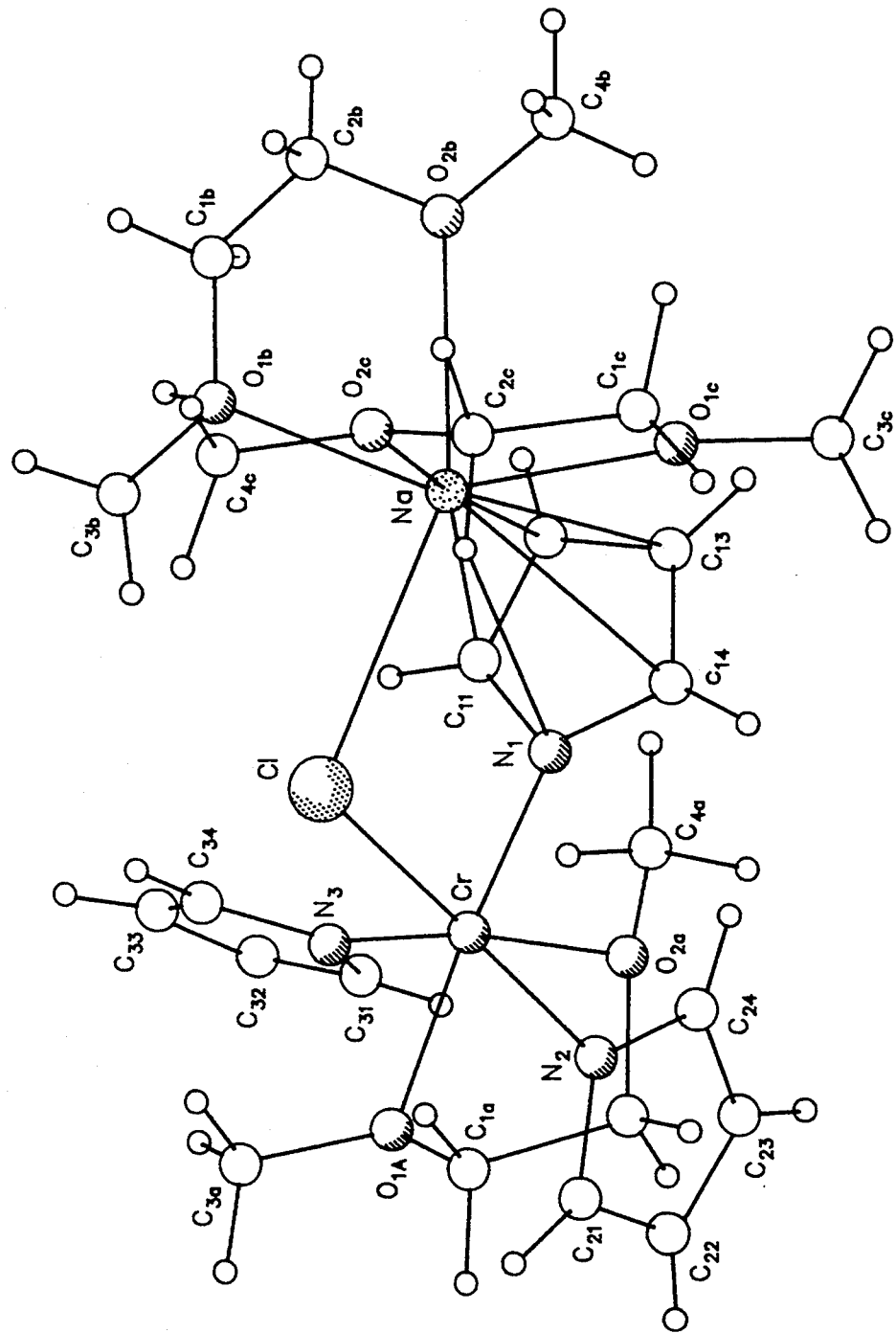
FIG. 8 is a further simplified ball and stick projection of the same molecule shown in FIG. 7.
Figure 9:
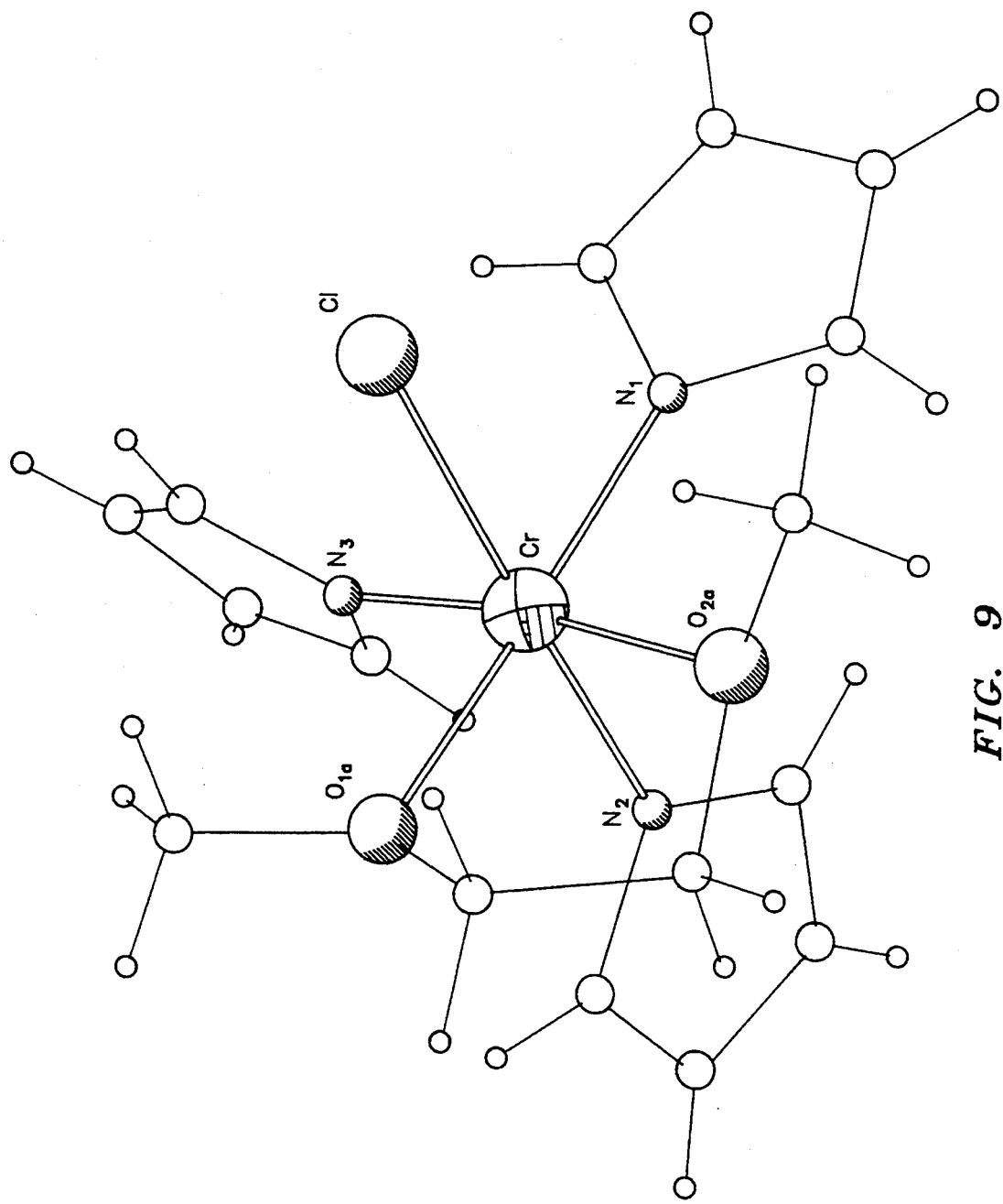
FIG. 9 is a further simplified ball and stick projection of $[Cr(NC_4H_4)_3Cl(O_2C_2H_4(CH_3)_2)]^{-1}$, with the exception of the chromium atom which is represented as a thermal ellipsoid. This is the same molecule as that shown in FIGS. 7 and 8, however, the entire crystal structure, or lattice, is not shown in FIG. 9.

Single crystal x-ray structures were obtained for Cr(NC$_4$H$_4$)$_3$Cl(O$_2$C$_2$H$_4$(CH$_3$)$_2$)$_3$Na, shown in FIGS. 7 and 8, and Cr(NC$_4$H$_4$)$_3$Cl(O$_2$C$_2$H$_4$(CH$_3$)$_2$), and shown in FIG. 9. These crystals were obtained in accordance with the procedure given in Example III. However, x-ray quality crystals were obtained after the dark green, filtered solution was maintained at ambient temperature and pressure under an inert atmosphere, nitrogen, for a time of about 2 days. Analysis calculated for C$_{24}$H$_{42}$N$_3$O$_6$CrNaCl: C, 49.78; H, 7.31; N, 7.26% by weight. Found: C, 49.80; I 7.39; N, 7.18% by weight. The description of tile single-crystal sample and mounting used for data collection are as follows:
Color: Green/black $\alpha = 90.00°$
$\beta = 91.67(2)°$
$\partial = 90.00°$
$V = 3027(1)Å^3$
$Z = 4$
$\lambda = 0.71073Å$
Molecular Weight: 579.05 amu
Calculated Density: 1.271 g/cm$^{-3}$
Linear Absorption Coefficient: 0.51mm$^{-1}$ Tables XVIII–XXII list the resultant parameters used to generate the molecular structures shown in FIGS. 7 and 8.

TABLE XVIII

Atomic Coordinates for Nonhydrogen Atoms in Crystalline [Cr(NC$_4$H$_4$)$_3$(Cl)(O$_2$C$_2$H$_4$(CH$_3$)$_2$)$_3$Na][a]

| Atom Type[b] | Fractional Coordinates | | | Equivalent Isotropic Thermal Parameter, B, Å$^2$ × 10[c] |
|---|---|---|---|---|
| | 10$^4$x | 10$^4$y | 10$^4$z | |
| Cr | −1030(1) | 559(1) | 3005(1) | 30(1) |
| Cl | 135(1) | −26(1) | 1981(1) | 41(1) |
| Na | −2167(2) | −1011(1) | 1832(1) | 46(1) |
| N$_1$ | −3062(4) | 65(2) | 2907(2) | 35(1) |
| C$_{11}$ | −4107(5) | 63(2) | 2251(3) | 40(1) |
| C$_{12}$ | −5189(5) | −409(2) | 2291(3) | 51(1) |
| C$_{13}$ | −4810(5) | −713(2) | 2998(3) | 51(1) |
| C$_{14}$ | −3512(5) | −414(2) | 3361(3) | 46(1) |
| N$_2$ | −1817(4) | 1027(2) | 3950(2) | 37(1) |
| C$_{21}$ | −1188(6) | 1558(2) | 4234(3) | 47(1) |
| C$_{22}$ | −2205(7) | 1790(2) | 4799(3) | 60(2) |

TABLE XVIII-continued

Atomic Coordinates for Nonhydrogen Atoms in Crystalline $[Cr(NC_4H_4)_3(Cl)(O_2C_2H_4(CH_3)_2)_3Na]^a$

| Atom Type[b] | Fractional Coordinates | | | Equivalent Isotropic Thermal Parameter, B, $Å^2 \times 10^c$ |
|---|---|---|---|---|
| | $10^4x$ | $10^4y$ | $10^4z$ | |
| $C_{23}$ | −3499(7) | 1398(2) | 4874(3) | 60(2) |
| $C_{24}$ | −3248(5) | 934(2) | 4349(2) | 43(1) |
| $N_3$ | −1892(4) | 1185(2) | 2260(2) | 35(1) |
| $C_{31}$ | −3100(5) | 1588(2) | 2434(3) | 41(1) |
| $C_{32}$ | −3573(6) | 1901(2) | 1757(3) | 53(1) |
| $C_{33}$ | −2631(6) | 1686(2) | 1130(3) | 51(1) |
| $C_{34}$ | −1620(6) | 1249(2) | 1453(3) | 46(1) |
| $O_{1a}$ | 1317(3) | 971(1) | 3154(2) | 40(1) |
| $O_{2a}$ | 153(3) | −12(1) | 3878(2) | 40(1) |
| $C_{1a}$ | 2459(5) | 631(2) | 3651(3) | 53(1) |
| $C_{2a}$ | 1443(6) | 329(2) | 4268(3) | 53(1) |
| $C_{3a}$ | 2156(6) | 1247(2) | 2495(3) | 58(2) |
| $C_{4a}$ | 653(6) | −625(2) | 3733(3) | 49(1) |
| $O_{1b}$ | −2558(4) | −783(2) | 398(2) | 62(1) |
| $O_{2b}$ | −3977(5) | −1772(2) | 1111(2) | 76(1) |
| $C_{1b}$ | −3618(9) | −1166(3) | −25(4) | 89(2) |
| $C_{2b}$ | −3627(9) | −1765(3) | 302(4) | 83(2) |
| $C_{3b}$ | −2410(8) | −207(3) | 61(4) | 79(2) |
| $C_{4b}$ | −4149(9) | −2328(3) | 1440(5) | 106(3) |
| $O_{1c}$ | −1334(4) | −1823(2) | 2911(2) | 65(1) |
| $O_{2c}$ | 235(5) | −1589(2) | 1529(3) | 87(2) |
| $C_{1c}$ | 71(7) | −2144(3) | 2724(4) | 83(2) |
| $C_{2c}$ | 951(8) | −1913(4) | 2067(4) | 107(3) |
| $C_{3c}$ | −2090(8) | −2017(3) | 3614(4) | 83(2) |
| $C_{4c}$ | 1224(8) | −1393(3) | 900(4) | 88(2) |

[a] The numbers in parentheses are the estimated standard deviations in the last significant digit.
[b] Atoms are labeled in agreement with FIG. 7.
[c] This is one-third of the trace of the orthogonalized $B_{ij}$ tensor.

TABLE XIX

Anisotropic Thermal Parameters for Nonhydrogen Atoms in Crystalline $[Cr(NC_4H_4)_3(Cl)(O_2C_2H_4(CH_3)_2)_3Na]^{a,b}$

| Atom Type[c] | Anisotropic Thermal Parameter ($Å^2 \times 10$) | | | | | |
|---|---|---|---|---|---|---|
| | $B_{11}$ | $B_{22}$ | $B_{33}$ | $B_{12}$ | $B_{13}$ | $B_{23}$ |
| Cr | −28(1) | 31(1) | 30(1) | 2(1) | −0(1) | −2(1) |
| Cl | 39(1) | 43(1) | 41(1) | 2(1) | 5(1) | −9(1) |
| Na | 47(1) | 48(1) | 44(1) | 0(1) | 3(1) | −4(1) |
| $N_1$ | 31(1) | 39(2) | 35(2) | 0(1) | 2(1) | −3(1) |
| $C_{11}$ | 31(2) | 47(2) | 41(2) | 0(2) | −1(2) | −7(2) |
| $C_{12}$ | 33(2) | 59(3) | 61(3) | −3(2) | −4(2) | −16(2) |
| $C_{13}$ | 35(2) | 39(2) | 79(3) | −6(2) | 8(2) | 3(2) |
| $C_{14}$ | 39(2) | 45(2) | 54(2) | 1(2) | 2(2) | 10(2) |
| $N_2$ | 36(2) | 38(2) | 36(2) | 7(1) | −3(1) | −8(1) |
| $C_{21}$ | 55(2) | 38(2) | 47(2) | 9(2) | −6(2) | −5(2) |
| $C_{22}$ | 88(3) | 46(3) | 44(2) | 32(2) | −9(2) | −12(2) |
| $C_{23}$ | 65(3) | 74(3) | 42(2) | 32(2) | 7(2) | 0(2) |
| $C_{24}$ | 37(2) | 55(2) | 37(2) | 14(2) | −0(2) | 1(2) |
| $N_3$ | 39(2) | 35(2) | 32(2) | 3(1) | 0(1) | −0(1) |
| $C_{31}$ | 35(2) | 43(2) | 43(2) | 6(2) | −3(2) | 1(2) |
| $C_{32}$ | 52(2) | 47(2) | 58(3) | 8(2) | −11(2) | 6(2) |
| $C_{33}$ | 62(3) | 51(3) | 39(2) | −2(2) | −8(2) | 12(2) |
| $C_{34}$ | 52(2) | 45(2) | 40(2) | −1(2) | 2(2) | 2(2) |
| $O_{1a}$ | 32(1) | 40(1) | 50(2) | −1(1) | −3(1) | −5(1) |
| $O_{2a}$ | 40(1) | 38(1) | 41(1) | 6(1) | −7(1) | −1(1) |
| $C_{1a}$ | 33(2) | 50(3) | 73(3) | 4(2) | −13(2) | −10(2) |
| $C_{2a}$ | 53(2) | 55(3) | 51(2) | 10(2) | −24(2) | −10(2) |
| $C_{3a}$ | 45(2) | 53(3) | 76(3) | −15(2) | 8(2) | −5(3) |
| $C_{4a}$ | 50(2) | 40(2) | 58(3) | 12(2) | −8(2) | −1(2) |
| $O_{1b}$ | 76(2) | 63(2) | 47(2) | −14(2) | −5(2) | 1(2) |
| $O_{2b}$ | 101(3) | 62(2) | 63(2) | −28(2) | −5(2) | −2(2) |
| $C_{1b}$ | 120(5) | 91(4) | 56(2) | −29(4) | −25(3) | −3(3) |
| $C_{2b}$ | 116(5) | 64(3) | 69(4) | −15(3) | −2.4(3) | −12(3) |
| $C_{3b}$ | 81(4) | 64(4) | 72(4) | −9(3) | −1(3) | 19(3) |
| $C_{4b}$ | 118(5) | 94(4) | 113(5) | −51(4) | −38(4) | 29(4) |
| $O_{1c}$ | 61(2) | 64(2) | 70(2) | 8(2) | 0(2) | 4(2) |
| $O_{2c}$ | 74(2) | 76(3) | 112(3) | 29(2) | 31(2) | 30(2) |
| $C_{1c}$ | 73(3) | 65(3) | 113(5) | 23(3) | 9(3) | 25(3) |
| $C_{2c}$ | 63(4) | 143(6) | 96(5) | 61(4) | 24(3) | 14(5) |
| $C_{3c}$ | 84(4) | 64(3) | 101(5) | −8(3) | 3(4) | 16(3) |
| $C_{4c}$ | 77(4) | 98(5) | −90(5) | 13(3) | 29(3) | −5(4) |

[a] The numbers in parentheses are the estimated standard deviations in the last significant digit.
[b] The form of the anisotropic thermal parameter is given in reference 8 on page 6 of the crystal structure analysis report.
[c] Atoms are labeled in agreement with FIG. 7.

TABLE XX

Atomic Coordinates for Hydrogen Atoms in Crystalline $[Cr(NC_4H_4)_3(Cl)(O_2C_2H_4(CH_3)_2)_3Na]^a$

| Atom Type[b] | Fractional Coordinates | | |
|---|---|---|---|
| | $10^4x$ | $10^4y$ | $10^4z$ |
| $H_{11}$ | −4089 | 350 | 1823 |
| $H_{12}$ | −6043 | −509 | 1905 |
| $H_{13}$ | −5349 | −1064 | 3195 |
| $H_{14}$ | −2993 | −526 | 3863 |
| $H_{21}$ | −188 | 1740 | 4663 |
| $H_{22}$ | −2044 | 2158 | 5089 |
| $H_{23}$ | −4404 | 1441 | 5226 |
| $H_{24}$ | −3967 | 597 | 4273 |
| $H_{31}$ | −3554 | 1644 | 2954 |
| $H_{32}$ | −4392 | 2210 | 1720 |
| $H_{33}$ | −2680 | 1817 | 581 |
| $H_{34}$ | −840 | 1021 | 1159 |
| $H_{1aa}$ | 3014 | 339 | 3336 |
| $H_{1ab}$ | 3254 | 892 | 3906 |
| $H_{2aa}$ | 967 | 626 | 4606 |
| $H_{2ab}$ | 2127 | 67 | 4588 |
| $H_{3aa}$ | 1391 | 1487 | 2185 |
| $H_{3ab}$ | 2589 | 938 | 2162 |
| $H_{3ac}$ | 3040 | 1495 | 2696 |
| $H_{4aa}$ | −256 | −834 | 3484 |
| $H_{4ab}$ | 926 | −806 | 4242 |
| $H_{4ac}$ | 1586 | −646 | 3395 |
| $H_{1ba}$ | −4712 | −1006 | −11 |
| $H_{1bb}$ | −3277 | −1186 | −570 |
| $H_{2ba}$ | −2588 | −1951 | 204 |
| $H_{2bb}$ | −4492 | −1988 | 37 |
| $H_{3ba}$ | −1696 | 26 | 407 |
| $H_{3bb}$ | −3461 | −14 | 7 |
| $H_{3bc}$ | −1935 | −243 | −458 |
| $H_{4ba}$ | −4380 | −2289 | 2000 |
| $H_{4bb}$ | −3106 | −2524 | 1385 |
| $H_{4bc}$ | −4998 | −2561 | 1178 |
| $H_{1ca}$ | 795 | −2146 | 3189 |
| $H_{1cb}$ | −255 | −2547 | 2596 |
| $H_{2cb}$ | 1398 | −2252 | 1795 |
| $H_{2cb}$ | 1831 | −1676 | 2294 |
| $H_{3ca}$ | −3168 | −1848 | 3661 |
| $H_{3cb}$ | −1397 | −1884 | 4055 |
| $H_{3cc}$ | −2164 | −2446 | 3624 |
| $H_{4ca}$ | 456 | −1357 | 454 |
| $H_{4cb}$ | 2033 | −1690 | 780 |
| $H_{4cc}$ | 1756 | −1015 | 996 |

[a] The 6 methyl groups were refined as rigid rotors with sp³-hybridized geometry and C—H bond lengths of 0.96Å. The initial orientation of each methyl group was determined from difference Fourier positions for the hydrogen atoms. The final orientation of each methyl group was determined by three rotational parameters. The refined positions for the rigid rotor methyl groups gave O—C—H angles which ranged from 103° to 115°. The remaining hydrogen atoms were included in the structure factor calculations as idealized atoms (assuming sp²- or sp³-hybridization of the carbon atoms and a C—H bond length of 0.96Å) "riding" on their respective carbon atoms. The isotropic thermal parameter of each hydrogen was fixed at 1.2 times the equivalent isotropic thermal parameter of the carbon atom to which it is covalently bonded.
[b] Hydrogens are labeled with the same subscripts as their carbon atoms with an additional literal subscript (a, b or c) where necessary to distinguish between hydrogen atoms bonded to the same carbon.

TABLE XXI

Bond lengths Involving Nonhydrogen Atoms in Crystalline $[Cr(NC_4H_4)_3(Cl)(O_2C_2H_4(CH_3)_2)_3Na]^a$

| Type[b] | Length, Å | Type[b] | Length, Å |
|---|---|---|---|
| Cr—Cl | 2.369(1) | Cr—$N_1$ | 1.990(3) |

TABLE XXI-continued

Bond lengths Involving Nonhydrogen Atoms in Crystalline
$[Cr(NC_4H_4)_3(Cl)(O_2C_2H_4(CH_3)_2)_3Na]^a$

| Type[b] | Length, Å | Type[b] | Length, Å |
|---|---|---|---|
| | | $Cr-N_2$ | 2.010(3) |
| $Cr-O_{1a}$ | 2.128(3) | $Cr-N_3$ | 1.986(3) |
| $Cr-O_{2a}$ | 2.142(3) | | |
| $N_1-C_{11}$ | 1.365(5) | $C_{11}-C_{12}$ | 1.376(6) |
| $N_1-C_{14}$ | 1.366(6) | $C_{12}-C_{13}$ | 1.386(7) |
| $N_2-C_{21}$ | 1.370(6) | $C_{13}-C_{14}$ | 1.376(6) |
| $N_2-C_{24}$ | 1.374(5) | $C_{21}-C_{22}$ | 1.373(7) |
| $N_3-C_{31}$ | 1.370(5) | $C_{22}-C_{23}$ | 1.377(8) |
| $N_3-C_{34}$ | 1.376(6) | $C_{23}-C_{24}$ | 1.375(7) |
| | | $C_{31}-C_{32}$ | 1.373(7) |
| $O_{1a}-C_{1a}$ | 1.443(5) | $C_{32}-C_{33}$ | 1.399(7) |
| $O_{1a}-C_{3a}$ | 1.448(6) | $C_{33}-C_{34}$ | 1.375(7) |
| $O_{2a}-C_{2a}$ | 1.437(5) | | |
| $O_{2a}-C_{4a}$ | 1.450(5) | $C_{1a}-C_{2a}$ | 1.498(7) |
| $O_{1b}-C_{1b}$ | 1.391(8) | $C_{1b}-C_{2b}$ | 1.445(9) |
| $O_{1b}-C_{3b}$ | 1.410(7) | $C_{1c}-C_{2c}$ | 1.422(10) |
| $O_{2b}-C_{2b}$ | 1.370(7) | | |
| $O_{2b}-C_{4b}$ | 1.379(8) | $Na \cdots Cr$ | 4.108(2) |
| $O_{1c}-C_{1c}$ | 1.392(7) | | |
| $O_{1c}-C_{3c}$ | 1.408(8) | $Na-Cl$ | 2.996(2) |
| $O_{2c}-C_{2c}$ | 1.278(9) | | |
| $O_{2c}-C_{4c}$ | 1.409(8) | $Na-N_1$ | 3.098(4) |
| $Na-C_{11}$ | 2.967(5) | $Na-O_{1b}$ | 2.454(4) |
| $Na-C_{12}$ | 2.924(5) | $Na-O_{2b}$ | 2.483(4) |
| $Na-C_{13}$ | 3.015(5) | $Na-O_{1c}$ | 2.629(5) |
| $Na-C_{14}$ | 3.104(5) | $Na-O_{2c}$ | 2.408(5) |
| $Na-C_{g1}$[c] | 2.788(—) | | |

[1]The numbers in parentheses are the estimated standard deviations in the last significant digit.
[b]Atoms are labeled in agreement with FIG. 7.
[c]The symbol $C_{g1}$ is used to designate the center of gravity for the five-membered ring containing $N_1$, $C_{11}$, $C_{12}$, $C_{13}$, and $C_{14}$; this value is therefore listed without an estimated standard deviation.

TABLE XXII

Bond Angles Involving Nonhydrogen Atoms in Crystalline
$[Cr(NC_4H_4)_3(Cl)(O_2C_2H_4(CH_3)_2)_3Na]^a$

| Type[b] | Angle, deg. | Type[b] | Angle, deg. |
|---|---|---|---|
| $ClCrN_1$ | 89.1(1) | $ClCrN_2$ | 173.9(1) |
| $N_1CrN_2$ | 94.0(1) | $ClCrN_3$ | 94.5(1) |
| $N_1CrN_3$ | 93.5(1) | $N_2CrN_3$ | 90.5(1) |
| $ClCrO_{1a}$ | 86.9(1) | $N_1CrO_{1a}$ | 171.9(1) |
| $N_2CrO_{1a}$ | 89.4(1) | $N_3CrO_{1a}$ | 93.8(1) |
| $ClCrO_{2a}$ | 88.9(1) | $N_1CrO_{2a}$ | 94.7(1) |
| $N_2CrO_{2a}$ | 85.7(1) | $N_3CrO_{2a}$ | 171.2(1) |
| $O_{1a}CrO_{2a}$ | 78.2(1) | | |
| $CrN_1C_{11}$ | 124.4(3) | $C_{11}N_1C_{14}$ | 105.7(3) |
| $CrN_1C_{14}$ | 128.6(3) | $C_{21}N_2C_{24}$ | 106.1(4) |
| $CrN_2C_{21}$ | 126.6(3) | $C_{31}N_3C_{34}$ | 106.0(3) |
| $CrN_2C_{24}$ | 126.5(3) | | |
| $CrN_3C_{31}$ | 125.0(3) | $CrO_{1a}C_{1a}$ | 123.5(2) |
| $CrN_3C_{34}$ | 128.3(3) | $CrO_{1a}C_{3a}$ | 122.5(3) |
| | | $C_{1a}O_{1a}C_{3a}$ | 110.5(3) |
| $N_1C_{11}C_{12}$ | 110.3(4) | $CrO_{2a}C_{2a}$ | 107.4(2) |
| $C_{11}C_{12}C_{13}$ | 106.9(4) | $CrO_{2a}C_{4a}$ | 124.9(3) |
| $C_{12}C_{13}C_{14}$ | 106.5(4) | $C_{2a}O_{2a}C_{4a}$ | 111.8(3) |
| $N_1C_{14}C_{13}$ | 110.6(4) | $C_{1b}O_{1b}C_{3b}$ | 114.7(4) |
| $N_2C_{21}C_{22}$ | 109.7(4) | $C_{2b}O_{2b}C_{4b}$ | 115.6(5) |
| $C_{21}C_{22}C_{23}$ | 107.4(4) | $C_{1c}O_{1c}C_{3c}$ | 114.2(5) |
| $C_{22}C_{23}C_{24}$ | 107.1(4) | $C_{2c}O_{2c}C_{4c}$ | 116.0(5) |
| $N_2C_{24}C_{23}$ | 109.7(4) | | |
| $N_3C_{31}C_{32}$ | 110.3(4) | $O_{1a}C_{1a}C_{2a}$ | 105.8(3) |
| $C_{31}C_{32}C_{33}$ | 107.0(4) | $O_{2a}C_{2a}C_{1a}$ | 109.8(4) |
| $C_{32}C_{33}C_{34}$ | 106.6(4) | $O_{1b}C_{1b}C_{2b}$ | 112.8(5) |
| $N_3C_{34}C_{33}$ | 110.2(4) | $O_{2b}C_{2b}C_{1b}$ | 112.6(5) |
| | | $O_{1c}C_{1c}C_{2c}$ | 114.9(6) |
| $ClNaC_{g1}$[c] | 83.6(—) | $O_{2c}C_{2c}C_{1c}$ | 121.1(6) |
| $ClNaO_{1b}$ | 89.5(1) | $C_{g1}NaO_{1b}$[c] | 111.1(—) |
| $ClNaO_{2b}$ | 156.0(1) | $C_{g1}NaO_{2b}$[c] | 110.2(—) |
| $ClNaO_{1c}$ | 108.2(1) | $C_{g1}NMaO_{1c}$[c] | 99.4(—) |
| $ClNaO_{2c}$ | 84.2(1) | $C_{g1}NaO_{2c}$[c] | 155.9(—) |
| $ClNaN_1$ | 61.5(1) | $O_{1b}NaO_{2b}$ | 67.4(2) |
| $ClNaC_{11}$ | 73.3(2) | $O_{1b}NaO_{1c}$ | 146.4(2) |
| $ClNaC_{12}$ | 100.0(2) | $O_{1b}NaO_{2c}$ | 89.4(2) |
| $ClNaC_{13}$ | 104.4(2) | $O_{2b}NaO_{1c}$ | 89.3(2) |
| $ClNaC_{14}$ | 81.1(2) | $O_{2b}NaO_{2c}$ | 88.8(2) |

TABLE XXII-continued

Bond Angles Involving Nonhydrogen Atoms in Crystalline
$[Cr(NC_4H_4)_3(Cl)(O_2C_2H_4(CH_3)_2)_3Na]^a$

| Type[b] | Angle, deg. | Type[b] | Angle, deg. |
|---|---|---|---|
| | | $O_{1c}NaO_{2c}$ | 65.1(2) |
| $N_1NaC_{11}$ | 25.9(2) | | |
| $N_1NaC_{14}$ | 25.5(2) | $N_1NaC_{12}$ | 43.8(2) |
| $C_{11}NaC_{12}$ | 27.0(2) | $N_1NaC_{13}$ | 43.2(2) |
| $C_{12}NaC_{13}$ | 26.9(2) | $C_{11}NaC_{13}$ | 43.5(2) |
| $C_{13}NaC_{14}$ | 125.9(2) | $C_{12}NaC_{14}$ | 42.9(2) |
| | | $C_{11}NaC_{14}$ | 41.9(2) |

[a]The numbers in parentheses are the estimated standard deviations in the last significant digit.
[b]Atoms are labeled in agreement with FIG. 7.
[c]The symbol $C_{g1}$ is used to designate the center of gravity for the five-membered ring containing $N_1$, $C_{11}$, $C_{12}$, and $C_{14}$; this value is therefore listed without an estimated standard deviation.

EXAMPLE X

Run 1001

0.14 g (0.29 mmol) of chromium (III) 2-ethylhexanoate ($CrEH_3$), $[Cr(C_8H_{15}O_2)_3]$, was weighed into a 25 ml pressure tube. The tube was capped with a self sealing crown cap. 0.062 ml (0.89 mmol) pyrrole (PyH), $[C_4NH_5]$ and cyclohexane, used as a diluent, were added via syringe to form a solution, which was about 8 ml total volume.

0.9 ml of a 1.1M solution (0.99 mmol) of triethylaluminum (TEA), $[Al(C_2H_5)_3]$, in heptane and a 0.9 ml aliquot of the $CrEH_3$/PyH solution were added under a counterflow of ethylene (CP grade) to a 1 liter autoclave reactor, containing 300 mL cyclohexane, to form a catalyst system. The reactor was sealed and ethylene addition stopped until the reactor temperature reached a reaction temperature of 80° C. The ethylene pressure was increased to a total reactor pressure of 550 psig. Ethylene was then fed on demand for a 30 minute run time. At the end of the run, a sample of the liquid reaction product mixture was taken and analyzed via capillary gas chromatography. The remaining reaction product mixture was evaporated and the amount of solid product was determined. The results are summarized below in Table XXIII.

Run 1002

The procedure described in Run 1001 was followed except 8 ml of a 1.1M solution (8.8 mmol) of TEA in heptane was added directly to the $CrEH_3$/PyH solution to form a solution (10 ml total volume) and not to the reactor. A 0.7 ml aliquot of the $CrEH_3$ /PyH/TEA solution was added to the autoclave reactor. No additional TEA was introduced into the reactor. The results are summarized below in Table XXIII.

Run 1003

The procedure described in Run 1002 was followed except 0.10 g (0.29 mmol) chromium (III) acetylacetonate ($Cracac_3$), $[Cr(C_5H_7O_2)_3]$, was substituted for $CrEH_3$ and 6 ml of a 1.1M solution TEA (6.6 mmol) in heptane was used in the formation of a $Cracac_3$/PyH/TEA solution (8 ml total volume). A 1.4 ml aliquot of the $Cracac_3$/PyH/TEA solution was added to the autoclave reactor. The results are summarized below in Table XXIII.

Run 1004

The procedure described in Run 1001 was followed except 0.9 ml of a 1M solution (0.9 mmol) of diethylaluminum chloride (DEAC), [AlCi(C$_2$H,)$_2$], in hexanes was added to the CrEH$_3$/PyH solution to form a CrEH$_3$/PyH/DEAC solution. A 0.65 ml aliquot of the CrEH$_3$/PyH/DEAC solution and 0.9 ml of a 1.1M solution (0.99 mmol) of TEA in heptane were added to the autoclave reactor. The results are summarized below in Table XXIII.

Run 1005

The procedure described in Run 1001 was followed except 0.9 ml of a 1M solution (0.9 mmol) of DEAC in hexanes was added to the CrEH$_3$/PyH solution and the resultant CrEH$_3$/PyH/DEAC solution was aged for 1 day at ambient temperature and pressure, under dry nitrogen. A 0.65 ml aliquot of the aged CrEH$_3$/PyH/DEAC solution +0.9 ml of a 1.1M solution (0.99 mmol) of TEA in heptane were added to the autoclave reactor. The results are summarized below in Table XXIII.

Run 1006

The procedure described in Run 1001 was followed except a solution was prepared using 0.13 ml pyrrole. Additionally, 1.0 ml of a 0.1M solution (0.1 mmol) of DEAC in hexanes was added along with the TEA to the reactor. A 0.9 ml aliquot of the CrEH$_3$/PyH solution was used. The results are summarized below in Table XXIII.

Run 1007

The procedure described in Run 1003 was followed except 3 ml of a 1.9M solution (5.7mmol) of TEA in toluene was used and toluene was substituted for the cyclohexane diluent in the formation of the CrEH$_3$/PyH/TEA solution. Thus, an excess of toluene was present inthe reactor. A 0.9 ml aliquot of the CrEH$_3$/PyH/TEA solution was used. The results are summarized below in Table XXIII.

Run 1008

The procedure described in Run 1002 was followed except 0.10 g of a chromium (III) pyrrolide (CrPy$_3$), [Cr(C$_4$H$_4$N)$_3$ClNa(C$_4$H$_{10}$O$_2$)$_3$] (0.17 mmol) was substituted for CrEH$_3$, and a solution was prepared using 0.04 ml (0.52 mmol) PyH and 3.5 ml of a 1.1M TEA (3.85 mmol) in heptanes. The final solution volume was about 5 ml. A 1.0 ml aliquot of time CrPy$_3$/PyH/TEA solution was used. The results are summarized below in Table XXIII.

Run 1009

The procedure described in Run 1008 was followed except 1.8 ml of a 1.9M TEA solution (3.42 mmol) in toluene was used, and toluene was substituted for cyclohexane in the formation of the CrPya/PyH/TEA solution. Thus, an excess of toluene was present in the reactor. A 1.4 ml aliquot of the CrPy$_3$/PyH/TEA solution was used. The results are summarized below in Table XXIII.

Run 1010

The procedure described in Run 1008 was followed except no neat PyH was added during the preparation of a CrPy$_3$/TEA solution. A 1.4 ml aliquot of the CrPy$_3$/TEA solution, in cyclohexane, was used. The results are summarized below in Table XXIII.

Run 1011

The procedure described in Run 1009 was followed except no neat PyH was added during the preparation of a CrPy$_3$/TEA solution. A 1.4 ml aliquot of the CrPy$_3$/TEA solution, in toluene, was used. Thus, an excess of toluene was present in the reactor. The results are summarized below in Table XXIII.

TABLE XXIII

Homogeneous Catalyst Systems

| Run | mg Cr (Elemental) Charged | Activity (g product/ g Cr/Hr) | Total Product Yield, g | Wt. % Liquid | Wt. % Solid | Liquid Product Distribution, Weight Percent | | | | | | |
|---|---|---|---|---|---|---|---|---|---|---|---|---|
| | | | | | | C$_4$= | 1-C$_6$= | C$_6$= | C$_8$= | C$_{10}$= | C$_{12}$= | C$_{14}$= |
| 1001 | 1.6 | 11,000 | 8.8 | 94 | 6 | 2 | — | 89a | 2 | 6 | <1 | <1 |
| 1002 | 0.96 | 8,800 | 4.2 | 88 | 12 | 1 | 87 | 5 | 2 | 4 | <1 | <1 |
| 1003 | 2.6 | 9,800 | 12.8 | 64 | 36 | 2 | 81 | 4 | 4 | 5 | 1 | 1 |
| 1004 | 1.1 | 15,000 | 8.5 | 98 | 2 | <1 | - | 92a | 1 | 6 | <1 | <1 |
| 1005 | 1.1 | 26,000 | 14.9 | 98 | 2 | <1 | 88 | 4 | 6 | <1 | <1 | <1 |
| 1006 | 1.5 | 12,000 | 9.0 | 98 | 2 | <1 | - | 97a | 1 | 2 | <1 | <1 |
| 1007 | 2.6 | 3,500 | 4.6 | 50 | 50 | 2 | 86 | 4 | 3 | 3 | <1 | <1 |
| 1008 | 2.5 | 8,300 | 10.5 | >99 | <1 | 1 | 83 | .5 | <1 | 8 | <1 | 1 |
| 1009 | 2.5 | 4,100 | 5.2 | 99 | 1 | 1 | 88 | 4 | 1 | 6 | <1 | <1 |
| 1010 | 2.5 | 7,100 | 8.9 | 97 | 3 | <1 | 82 | 6 | 1 | 8 | <1 | 1 |
| 1011 | 2.5 | 3,300 | 4.2 | 98 | 2 | <1 | 89 | 4 | 1 | 5 | <1 | <1 |

*a*Total hexenes.

EXAMPLE XI

It should be noted that the results in Table XXIII, from Example X, and the results in Table XXIV, from Example XI, are not directly comparable, due to reactions conducted in different reactors, under different conditions by the use of different ethylene and cyclohexane feedstocks, as well as different diluents. However, direct comparisons within each Example can be made.

Run 2001

0.30 g (0.62 mmol) of chromium (III) 2-ethylhexanoate (CrEH$_3$) (10.15 wt % Cr) was combined with 0.12 mi (1.73 mmole) of neat pyrrole (PyH) in 10 ml of toluene. 2.8 ml of 1.9M triethylaluminum (TEA) solution (5.32 mmol) in toluene was added, and the CrEH$_3$/PyH/TEA solution was stirred for 30 minutes under dry nitrogen, at ambient temperature and pressure. The dark brown CrEH$_3$/PyH/TEA solution was filtered and excess toluene was removed by vacuum stripping, which resulted in 1.0 ml of a dark brown oil, used as catalyst system. Under a counterflow of ethylene, 0.5 ml (0.15 g CrEH$_3$; 15.2 mg Cr) of the catalyst system and 4.0 ml of nonane (reactor internal standard) were added to a 2 liter autoclave reactor at 80° C., which contained 1.2 liters of cyclohexane. The reactor was then pressurized with ethylene to 550 psig, and the reaction was run for 30 minutes, with ethylene being fed on demand.

The results are summarized below in Table XXIV.

Run 2002

The procedure described in Run 2001 was followed except diethylaluminum chloride was added in addition to the $CrEH_3/PyH/TEA$ solution.

0.53 g (1.10 mmol) of $CrEH_3$ (10.15 wt. % Cr) was combined with 0.52 ml (7.5 mmole) of neat PyH in 15 ml of toluene and stirred for 5 min. 9.0 ml of a 1.9M TEA solution (17.1 mmol) in toluene was added, and the $CrEH_3/PyH/TEA$ solution was stirred overnight under dry nitrogen at ambient temperature and pressure. Excess toluene was removed from the resultant dark brown solution via vacuum stripping, which resulted in 2.5 ml of a dark brown oil. 0.5 ml (10.8mg; 0.21 mmole Cr) of the dark brown oil was combined with 1.0 ml of a 0.87M (0.87 mmol) diethylaluminum chloride (DEAC) solution in nonane, and the $CrEH_3/PyH/TEA/DEAC$ solution was stirred overnight under dry nitrogen, at ambient temperature and pressure. The resultant product was used as the catalyst system. Under a counterflow of ethylene, 1.3 ml (9.4mg Cr; 0.18 mmole Cr) of the catalyst system and 4.0 ml of nonane (reactor internal standard) were charged directly to 2 a liter reactor at 80° C., which contained 1.2 liters of cyclohexane. The reactor was then pressurized with ethylene to 550 psig, and the reaction was run for 30 minutes with ethylene being fed on demand.

The results are summarized below in Table XXIV.

Run 2003

0.33 g (0.68 mmol) of $CrEt_3$ (10.15 wt. % Cr) was combined with 0.13 ml (1.87 mmole) of neat PyH in 10 ml of toluene and stirred 5 min. 1.9 ml of a 1M (1.9 mmol) DEAC solution in hexanes was added and the $CrEH_3/PyH/DEAC$ solution was stirred for 30 minutes under dry nitrogen, at ambient temperature and pressure, which resulted in a light yellow/ green solution. 5.1 ml of a 1.9M (9.7 mmol) diethylaluminum chloride (DEAC) solution in toluene was added, and the $CrEH_3/PyH/DEAC/TEA$ solution was stirred for 0.5 hr, which resulted in a dark yellow/brown solution. Excess toluene and hexane was removed from the dark yellow/brown $CrEH_3/PyH/DEAC/TEA$ solution via vacuum stripping, with a dark yellow/brown oil remaining. The yellow/brown oil was dissolved and brought to a total volume in 25 ml of cyclohexane and used as a catalyst system (1.32mg Cr/ml). Under a counterflow of ethylene, 7.0 ml (9.2mg Cr; 0.178 mmole Cr) of the catalyst system and 4.0 ml of nonane (reactor internal standard) were charged directly to a 2 liter reactor at 80° C., which contained 1.2 liters of cyclohexane. The reactor was then pressurized with ethylene to 550 psig and the reaction was run for 30 minutes with ethylene being fed on demand.

The results are summarized below in Table XXIV.

Run 2004

The procedure described in Run 2002 was followed, except the $CrEH_3/PyH/TEA/DEAC$ solution was diluted with cyclohexane prior to charging to the reactor, and dihydrogen gas ($H_2$) (50 psig) was added to the reactor prior to pressurizing the reactor with ethylene.

0.30 g (0.62 mmol) of $CrEH_3$ (10.15% Cr) was combined with 0.12 ml (1.73 mmole) of neat PyH in 10 ml of toluene. 1.7 ml of a 1M (1.7 mmol) DEAC solution in hexanes was added and the $CrEH/PyH/DEAC$ solution was stirred for 5 minutes under dry nitrogen, at ambient temperature and pressure. 1.8 ml of a 1.9M (3.42 mmol) TEA solution in toluene was added and the $CrEH_3/PyH/DEAC/TEA$ solution was stirred for 30 minutes under dry nitrogen, at ambient temperature and pressure. The resultant dark brown solution was filtered and excess toluene and hexanes were removed via vacuum stripping, which resulted in 0.8 ml of a dark yellow/brown oil and was used as a catalyst system. Under a counterflow of ethylene, 0.4 ml (15.2 mg Cr; 0.29 mmole Cr) of the catalyst system and 4.0 ml of nonane (reactor internal standard) were charged directly to the 2 liter reactor at 80° C., which contained 1.2 liters of cyclohexane. 50 psig of dihydrogen ($H_2$) gas was charged to the reactor, followed by pressurization with ethylene to 550 psig. The reaction was run for 30 minutes with ethylene being fed on demand.

The results are summarized below in Table XXIV.

Run 2005

In a 500 ml Schlenk flask 1.98 g (3.4 mmol) of $CrPy_3$ (11.1 wt. % Cr) was combined with 40 ml of toluene and 54 ml of a 1.9M (102.6 mmol) TEA solution in toluene. The resulting dark brown reaction mixture was stirred for 1 hour under dry nitrogen, at ambient temperature and pressure. Excess toluene was removed via vacuum stripping, which resulted in 13 ml of a dark yellow/brown oil and a small quantity of a light-colored precipitate. The dark yellow/brown oil was separated, collected by syringe from the precipitate, and used as the catalyst system. 2.0 ml of the catalyst system was diluted with 27 ml of cyclohexane and aged for 3 days under dry nitrogen, at ambient temperature and pressure before using.

Under a counterflow of ethylene, 8.0 ml (9.3mg; 0.18 mmole Cr) of the catalyst system/cyclohexane solution and 4.0 ml of nonane (reactor internal standard) were charged directly to a 2 liter autoclave reactor at 80° C., which contained 1.2 liters of cyclohexane. The reactor was then pressurized with ethylene to 550 psig and the reaction was run for 30 minutes with ethylene being fed on demand.

The results are summarized below in Table XXIV.

Run 2006

The procedure described in Run 2005 was followed except less reactants were used and less aging time was used.

In a 500 ml Schlenk flask 0.25 g (0.432 mmol) of $CrPy_3$ (11.1 wt. % Cr) was combined with 10 ml of toluene and 3.4 ml of a 1.9M (6.46 mmol) TEA solution in toluene. The resulting dark brown reaction mixture was stirred for 30 minutes under dry nitrogen, at ambient temperature and pressure. Excess toluene was removed via vacuum stripping, which resulted in a dark brown oil. All of the dark brown oil was diluted to a total volume of 25 ml with cyclohexane, resulting in a solution containing 1.11 mg Cr/ml, which was used as the catalyst system.

Under a counterflow of ethylene, 8.0 ml (8.88 mg; 0.171 mmole Cr) of the catalyst system/cyclohexane solution and 4.0 ml of nonane (reactor internal standard) were charged directly to a 2 liter autoclave reactor at 80° C., which contained 1.2 liters of cyclohexane. The reactor was then pressurized with ethylene to 550 psig and the reaction was run for 30 minutes with ethylene being fed on demand.

The results are summarized below in Table XXIV.

Run 2007

The procedure described in Run 2005 was followed except excess toluene was present in the trimerization reactor.

In a 500 ml Schlenk flask 1.98 g (3.4 mmol) of $CrPy_3$ (11.1 wt. % Cr) was combined with 40 ml of toluene and 54 ml of a 1.9M (102.6 mmol) TEA solution in toluene. The resulting dark brown reaction mixture was stirred for 1 hour under dry nitrogen, at ambient temperature and pressure. Excess toluene was removed via vacuum stripping, which resulted in 13 ml of a dark yellow/brown oil and a small quantity of a light-colored precipitate., The dark yellow/brown oil was separated, collected by syringe from the precipitate, and used as the catalyst system. 2.0 ml of the catalyst system was diluted with 27 ml of cyclohexane and aged for 3 days under dry nitrogen, at ambient temperature and pressure before using.

Under a counterflow of ethylene, 0.5 ml (8.5 mg; 0.163 mmole Cr) of the catalyst system/cyclohexane solution, 4.5 ml of toluene, and 4.0 ml of nonane (reactor internal standard) were charged directly to a 2 liter autoclave reactor at 80° C., which contained 1.2 liters of cyclohexane. The reactor was then pressurized with ethylene to 550 psig and the reaction was run for 30 minutes with ethylene being fed on demand.

The results are summarized below in Table XXIV.

Run 2008

0.28 g (0.802 mmol) of $Cracac_3$ was combined with 0.17 ml (2.45 mmol) of neat pyrrole in 10 ml of toluene and stirred under dry nitrogen, at ambient temperature and pressure for 5 minutes. Then, 6.3 ml of a 1.9M (12.0 mmol) TEA solution in toluene was added. The resulting dark brown reaction mixture was stirred for 30 minutes under dry nitrogen, at ambient temperature and pressure. Excess toluene was removed via vacuum stripping, which resulted in a dark yellow/brown oil. All of the dark yellow/brown oil was diluted to a volume of 25 ml with cyclohexane, resulting in a solution containing 0.0112 g $Cracac_3$/ml, which was used as the catalyst system.

Under a counterflow of ethylene, 7.0 ml (15.2 mg; 0.293 mmole Cr) of the catalyst system/cyclohexane solution and 4.0 ml of nonane (reactor internal standard) were charged directly to a 2 liter autoclave reactor at 80° C., which contained 1.2 liters of cyclohexane. The reactor was then pressurized with ethylene to 550 psig and the reaction was run for 30 minutes with ethylene being fed on demand.

The results are summarized below in Table XXIV.

Run 2009

The procedure described in Run 2008 was followed except chromium (III) naphthenate was the chromium source.

0.33 g (0.508 mmol) of $CrNapth_3$ (8.0 wt. % Cr) was combined with 0.12 (1.73 mmol) of neat pyrrole in 10 ml of toluene and stirred under dry nitrogen at ambient temperature and pressure for 5 minutes. Then, 4.6 ml of a 1.9M (8.74 mmol) TEA solution in toluene was added. The resulting dark brown reaction mixture was stirred for 30 minutes under dry nitrogen, at ambient temperature and pressure. Excess toluene was removed via vacuum stripping, which resulted in a dark yellow/brown oil. All of the dark yellow/brown oil was diluted to a total volume of 25 ml with cyclohexane, resulting in a solution containing 1.056 mg Cr/ml, which was used as the catalyst system.

Under a counterflow of ethylene, 7.0 ml (7.39 mg; 0.142 mmole Cr) of the catalyst system/cyclohexane solution and 4.0 ml of nonane (reactor internal standard) were charged directly to a 2 liter autoclave reactor at 80° C. which contained 12 liters of cyclohexane The reactor was then pressurized with ethylene to 550 psig and the reaction was run for 30 minutes with ethylene being fed on demand.

The results are summarized below in Table XXIV.

Run 2010

The procedure described in Run 2008 was followed except the chromium (III) chloride was the chromium source.

0.41 g (1.09 mmol) of $CrCl_3THF_3$ was combined with 0.23 ml (3.32 mmol) of neat pyrrole in 10 ml of toluene and stirred under dry nitrogen, at ambient temperature and pressure for 5 minutes. Then 8.6 ml of a 1.9M (16.3 mmol) TEA solution in toluene was added. The resulting dark brown reaction mixture was stirred for 30 minutes under dry nitrogen, at ambient temperature and pressure. Excess toluene was removed via vacuum stripping, which resulted in a dark yellow/brown oil. 7.5 ml of nonane was added to the dark yellow/brown oil and the resultant solution was diluted to a total volume of 25 ml with cyclohexane, resulting in a solution containing 0.0164 g $CrCl_3THF_3$/ml. The solution was filtered and the filtrate was used as the catalyst system.

Under a counterflow of ethylene, 5.0 ml (11.38 mg; 0.219 mmole Cr) of the catalyst system/cyclohexane/nonane solution and 2.5 ml of nonane (reactor internal standard) were charged directly to a 2 liter autoclave reactor at 80° C., which contained 1.2 liters of cyclohexane. The reactor was then pressurized with ethylene to 550 psig and the reaction was run for 30 minutes with ethylene being fed on demand.

The results are summarized below in Table XXIV.

Run 2011

The procedure described in Run 2005 was followed except excess hexene was charged to the trimerization reactor.

In a 500 ml Schlenk flask, 1.98 g (3.4 mmol) of $CrPy_3$ (11.1 wt. % Cr) was combined with 40 ml of toluene and 54 ml of a 1.9M (102.6 mmol) TEA solution in toluene. The resulting dark brown reaction mixture was stirred for 1 hour under dry nitrogen, at ambient temperature and pressure. Excess toluene was removed via vacuum stripping, which resulted in 13 ml of a dark yellow/brown oil and a small quantity of a light-colored precipitate. The dark yellow/brown oil was separated, collected by syringe from the precipitate, and used as the catalyst system. 2.0 ml of the catalyst system was diluted with 27 ml of cyclohexane and aged for 3 days under dry nitrogen, at ambient temperature and pressure before using.

Under a counterflow of ethylene, 1.0 ml (16.9 mg; 0.325 mmole Cr) of the catalyst system/cyclohexane solution, 55 ml of 1-hexene, and 4.0 ml of nonane (reactor internal standard) were charged directly to a 2 liter autoclave reactor at 80° C., which contained 1.2 liters of cyclohexane. The reactor was then pressurized with ethylene to 550 psig and the reaction was run for 30 minutes with ethylene being fed on demand.

The results are summarized below in Table XXIV.

Run 2012

The procedure described in Run 2005 was followed except chromium (II) pyrrolide (Compound I) was the chromium source.

0.30 g (about 0.85 mmol) of Compound I (CrPy$_{10}$THF$_4$) was combined with 10 ml of toluene and 6.7 ml of a 1.9M (12.7 mmol) TEA solution in toluene. The resulting dark brown reaction mixture was stirred for 30 minutes under dry nitrogen, at ambient temperature and pressure. Excess toluene was removed via vacuum stripping, which resulted in a dark yellow/brown oil and a small quantity of a light-colored precipitate. The dark yellow/brown oil was filtered and the filtrate was diluted to a total volume of 25 ml with cyclohexane, resulting in a solution containing 0.012 g Compound I (CrPy$_{10}$THF$_4$), which was used as the catalyst system.

Under a counterflow of ethylene, 7.0 ml of the catalyst system/cyclohexane solution and 4.0 ml of nonane (reactor internal standard) were charged directly to a 2 liter autoclave reactor at 80° C., which contained 1.2 liters of cyclohexane. The reactor was then pressurized with ethylene to 550 psig and the reaction was run for 30 minutes with ethylene being fed on demand.

The results are summarized below in Table XXIV.

TABLE XXIV

| | | | Catalyst Systems With Solvent Removal | | | | | | | | | |
|---|---|---|---|---|---|---|---|---|---|---|---|---|
| Run | mg Cr (Elemental) Charged | Molar Ratio Cr:Py: TEA:DEAC | Activity (g product/ g Cr/hr) | Total Product Yield, g | Wt. % Liquid | Wt. % Solid | $C_4^=$ | 1-$C_6^=$ | $C_6^=$ | $C_8^=$ | $C_{10}^=$ | $C_{12}^=$ | $C_{14}^=$ |
| 2001 | 5.2 | 1:3:9:0 | 4,000 | 30.5 | 74 | 26 | 9 | 53 | 2 | 9 | 9 | 5 | 4 |
| 2002 | 9.3 | 1:7:15.5:4 | 6,000 | 23.2 | 95 | 5 | <1 | 88 | 4 | 2 | 3 | <1 | <1 |
| 2003 | 9.2 | 1:3:15:15 | 8,300 | 38.5 | 88 | 12 | <1 | 86 | 3 | 2 | 5 | <1 | <1 |
| 2004 | 5.2 | 1:3:6:3 | 4,900 | 37.0 | 96 | 4 | <1 | 91 | 2 | 2 | 3 | <1 | <1 |
| 2005 | 7.5 | 1:3:30:0 | 10,600 | 40.0 | 98 | 2 | <1 | 82 | 9 | 1 | 7 | <1 | <1 |
| 2006 | 7.2 | 1:3:15:0 | 10,800 | 38.9 | 97 | 3 | <1 | 81 | 5 | 3 | 7 | <1 | 1 |
| 2007 | 6.8 | 1:3:30:0 | 1,100 | 3.2 | 94 | 6 | 4 | 84 | 6 | 1 | 4 | <1 | <1 |
| 2008 | 1.8 | 1:3:15 | 17,000 | 98.9 | 95 | 5 | <1 | 84 | 5 | 1 | 6 | <1 | <1 |
| 2009 | 7.4 | 1:3:15:0 | 15,700 | 57.8 | 72 | 28 | <1 | 88 | 2 | 2 | 5 | <1 | <1 |
| 2010 | 1.4 | 1:3:15 | 8,000 | 45.3 | 98 | 2 | <1 | 88 | 4 | 1 | 5 | <1 | <1 |
| 2011 | 3.7 | 1:30:0 | 4,600 | 31.3 | — | — | <1 | 76 | 11 | 1 | 10 | <1 | 1 |
| 2012 | 10.0 | 1:2:18.5:0 | 8,800 | 44.1 | 99 | 1 | <1 | 77 | 9 | 1 | 11 | <1 | 1 |

EXAMPLE XII

Run 300

0.21 g (0.601 mmol) of Cracac$_3$ was combined with 0.12 ml (1.73 mmol) of neat pyrrole and 15 ml of toluene. The resulting solution was stirred under dry nitrogen, at ambient temperature and pressure for 5 minutes. Then, 6.0 ml of a 1.9M (11.4 mmol) TEA solution in toluene was added. The resulting dark brown reaction mixture was stirred for 5 minutes under dry nitrogen, at ambient temperature and pressure. Then, 2.0 g of an aluminophosphate support (0.4 P/Al molar ratio, activated at 700° C.), prepared in accordance with U.S. Pat. No. 4,364,855 (1982), herein incorporated by reference, was added and the resulting slurry stirred for a period of approximately 12 hours. The product was collected by filtration, rinsed at least twice with 10 ml aliquots of toluene and pentane, until no color was observed in the filtrate and vacuum dried. The dried product was used as solid supported catalyst system.

A 2.1022 g aliquot of the solid catalyst system was added under a counterflow of ethylene to a 2 liter autoclave containing 1 liter of isobutane. Prior to the catalyst charge, 0.25 ml of a 16.5 wt % TEA solution in nonane was added to the reactor, in order to neutralize any ethylene feedstock poisons that might be present. The reactor was sealed and ethylene addition was stopped until the reactor temperature reached the desired run temperature, for example 90° C. The ethylene pressure was then increased to a total reactor pressure of 550 psig. Ethylene was fed on demand for a 30 minute run time. At the end of the run, a sample of the liquid reaction product mixture was collected and analyzed via gas chromatography. The remaining reaction mixture was evaporated and the amount of solid product was determined.

The results are summarized in Table XXV.

Run 3002

The procedure described in Run 3001 was followed except diethylaluminum chloride was added to the Cracac$_3$/PyH solution along with the TEA prior to the aluminophosphate inorganic oxide addition.

0.21 g Cracac$_3$ (0.60 mmol) was weighed into a 30 ml screw-capped vial. 0.12 ml of PyH (1.73 mmol) and 15 ml of toluene were added, and the resulting solution was capped and stirred for 5 minutes. Then, with continued stirring, 6 ml of a 1.9M (11.4 mmol) TEA solution in toluene was added. After the Cracac$_3$/PyH/TEA solution was stirred for 5 minutes, 2.4 ml of a 1M (2.4 mmol) DEAC solution in hexanes was added and the Cracac$_3$/PyH/TEA/DEAC/toluene solution was stirred for 5 minutes. 2.0 g of an aluminophosphate support (0.4 P/Al molar ratio, activated at 700° C.), prepared in accordance with U.S. Pat. No. 4,364,855 (1982), herein incorporated by reference, was added and the resulting slurry stirred for a period of approximately 12 hours. The product was collected by filtration and rinsed with at least two 10 ml aliquots of toluene and pentane, until no color was observed in the filtrate, and vacuum dried. The dried product was used as a solid, supported catalyst system.

A 0.5048 g aliquot of the solid catalyst system was added under a counterflow of ethylene to a 2 liter autoclave containing 1 liter of isobutane. Prior to the catalyst charge, 3.0 ml of a 1.6 wt % TEA solution in nonane was added in order to neutralize any ethylene feedstock poisons that might be present. The reactor was sealed and ethylene addition stopped until the reactor temperature reached the desired run temperature, for example 90° C. The ethylene pressure was increased to a total reactor pressure of 550 psig. Ethylene was then fed on demand for a 30 minutes run time. At the end of the run, a small sample of the liquid reaction product mixture was collected and analyzed via gas chromatography. The remaining reaction mixture was evaporated and the amount of solid product determined. Ethylene consumption was determined by a calibrated flow meter.

The results are summarized below in Table XXV.

Run 3003

The procedure described in Run 3002 was followed except CrEH$_3$ was the chromium source and no aromatic solvent was used during catalyst system preparation. Also, a supported catalyst system was prepared in-situ in the reactor.

A CrEH$_3$/PyH solution was prepared by mixing 0.33 g (0.69 mmole) CrEH$_3$ with 0.26 ml (3.75 mmole) PyH in 16 ml of pentane and aging for 4 days under dry nitrogen, at ambient temperature and pressure, prior to usage. 0.49 g of an aluminophosphate support (0.9 P/Al molar ratio, activated at 700° C.), prepared in accordance with U.S. Pat. No. 4,364,855 (1982), herein incorporated by reference, and 2.0 ml of a 1M (2.0 mmol) TEA solution in hexanes were charged under a counterflow of ethylene to a 2 liter autoclave reactor at ambient temperature. Then, 1 liter of cyclohexane, 2.1 ml (4.32mg; 0.083 mmole Cr) of the CrEH$_3$/PyH solution, and 50 psig dihydrogen gas (H$_2$) were charged to the reactor.

The results are summarized below in Table XXV.

EXAMPLE 4002

The procedure described in Run 4001 was followed except the solid catalyst component (88 mg collected) was prepared in a 25 ml pressure tube using 0.349 g (1 mmol) Cracac$_3$, 5 ml toluene, 0.14 ml (2 mmol) PyH, and 0.8 ml of a 2.5M (2.0 mmol) n-butyl lithium solution in hexane.

0.5 ml of a 1.1M (0.55 mmol) TEA solution in heptanes and a cyclohexane slurry containing 16 mg of the solid were used in a reaction under the conditions described in Run 1001.

The results are summarized below in Table XXVI.

Run 4003

1.0 g of aluminophosphate support (0.4 P/Al molar ratio, activated 700° C.), prepared in accordance with U.S. Pat. No. 4,364,855 (1982), herein incorporated by reference, and an 93 mg aliquot of the solid described in Run 4001, were weighed into a 25 ml pressure tube. The tube was capped. 5 ml toluene and 3 ml of a 1.9M (5.7 mmol) TEA solution in toluene were added to the tube via syringe. The resulting slurry was agitated for one day. The solid was isolated and washed with 10 ml aliquots of toluene and cyclohexane until no color was observed in the wash solution.

0.5 ml of a 1.1M (0.55 mmol) TEA solution in heptanes and a cyclohexane slurry containing 80 mg of the

TABLE XXV

| Run | Grams Catalyst System Charged | Molar Ratio Cr:Py: TEA:DEAC | Activity (g prod/g catalyst/ hr) | Total Product Yield, g | Wt % Liquid | Wt % Solid | Liquid Product Distribution, Weight Percent | | | | | | |
|---|---|---|---|---|---|---|---|---|---|---|---|---|---|
| | | | | | | | C$_4$= | 1-C$_6$= | C$_6$= | C$_8$= | C$_{10}$= | C$_{12}$= | C$_{14}$= |
| 3001 | 2.1022 | — | 210 | 223 | 82 | 18 | 1 | 76 | 7 | 2 | 11 | 1 | 2 |
| 3002 | 0.5048 | 1:3:19:4 | 340 | 87 | 99 | 1 | 1 | 82 | 7 | 1 | 8 | <1 | 1 |
| 3003 | 0.0426$^a$ | 1:5.5:22.6:0 | 450 | 224 | 88 | 12 | 6 | 61 | 6 | 5 | 13 | 2 | 3 |

$^a$Grams of onlyv Cr(EH)$_3$ charged: mass of catalyst system components are excluded.

EXAMPLE XIII

Run 4001

3.5 g (10 mmol) Cracac$_3$ was weighed into a 100 ml pressure tube. A stir bar was placed in the tube and the tube was capped with a self sealing crown cap. 40 ml toluene and 2.1 ml (30 mmol) PyH were added via syringe. 12 ml of a 2.5M (30.0 mmol) n-butyl lithium solution in hexanes was slowly added. A precipitate was formed, collected, and washed with one 10 ml aliquot of toluene and two 10 ml aliquots of cyclohexane, until no color was observed in the wash solution. A total of 5.59 g solid was obtained. 0.5 ml of a 1.1M (0.55 mmol) TEA solution in heptane and a slurry of 38 mg of the solid and cyclohexane were used in a reaction under the conditions described in Run 1001.

The results are summarized below in Table XXVI.

solid were used in a reaction under the conditions described in Run 1001.

The results are summarized below in Table XXVI.

Run 4004

0.7 g of aluminophosphate support (0.4 P/Al molar ratio, activated at 700° C.), prepared in accordance with U.S. Pat. No. 4,364,855 (1982), herein incorporated by reference, and an aliquot (53 mg) of the solid described in Run 402 were weighed into a 25 ml pressure tube. The tube was capped. 3.5 ml toluene and 2 ml of a 1.9M (3.8 mmol) TEA solution in toluene were added to the tube via syringe. The resulting slurry was agitated for one day. The solid was isolated and washed with 10 ml aliquots of toluene and cyclohexane until no color was observed in the wash solution.

0.5 ml of a 1.1M (0.55 mmol) TEA solution in heptane and a cyclohexane slurry containing 78 mg of the solid were used in a reaction under the conditions as described in Run 1001.

The results are summarized below in Table XXIV.

TABLE XXVI

| | | | | | | Lithium-Alkyls in Catalyst Preparation | | | | | | |
|---|---|---|---|---|---|---|---|---|---|---|---|---|
| Run | Grams Catalyst Charged | Activity (g prod/ g Cat/hr) | Total Product Yield, g | Wt. % Liquid | Wt. % Solid | Liquid Product Distribution, Weight Percent | | | | | | |
| | | | | | | C$_4$= | 1-C$_6$= | C$_6$= | C$_8$= | C$_{10}$= | C$_{12}$= | —C$_{14}$= |
| 4001 | 0.038 | 95 | 1.8 | 86 | 14 | 4 | 81 | 5 | 3 | 4 | <1 | <1 |
| 4002 | 0.016 | 540 | 4.3 | 82 | 18 | 3 | 83 | 5 | 3 | 4 | <1 | <1 |
| 4003 | 0.080 | 110 | 4.3 | 89 | 11 | 1 | 79 | 5 | 3 | 5 | 2 | 1 |

TABLE XXVI-continued

| | | | | | Lithium-Alkyls in Catalyst Preparation | | | | | | |
|---|---|---|---|---|---|---|---|---|---|---|---|
| | Grams | Activity | Total | | | | | Liquid Product Distribution, | | | |
| | Catalyst | (g prod/ | Product | Wt. % | Wt. % | | | Weight Percent | | | |
| Run | Charged | g Cat/hr) | Yield, g | Liquid | Solid | $C_4=$ | $1\text{-}C_6=$ | $C_6=$ | $C_8=$ | $C_{10}=$ | $C_{12}=$ | $\text{---}C_{14}=$ |
| 4004 | 0.078 | 310 | 12.2 | 84 | 16 | 1 | 78 | 6 | 2 | 8 | 1 | 1 |

EXAMPLE XIV

Run 5001

0.17 g chromium (III) 2,2,6,6-tetramethyl-3,5-heptanedionate (Cr(III)TMHD) (0.28 mmol) was weighed into a 25 ml pressure tube. The tube was capped with a self sealing crown cap. 0.06 ml of pyrrole (0.89 mmol) and 0.17 ml of neat (0.87 mmol) diisobutylaluminum chloride (DiBAlCl) were added via syringe to form a Cr(III)TMHD/DiBAlCl/Py solution, which was diluted to a total volume of about 8 ml with cyclohexane. 0.25 ml of a 1.1M (0.28 mmol) TEA solution in heptane and 0.75 ml of the Cr(III)TMHD/DiBAlCl/Py solution were added to a glass bottle containing 100 ml of cyclohexane and 10 g of butadiene. The glass bottle was placed in a controlled temperature bath at 70° C., at ambient pressure, and agitated for a period of 16 hours. After 16 hours, a small sample of the liquid reaction product mixture was collected and analyzed via gas chromatography. The remaining liquid reaction product mixture was evaporated and the amount of solid product was determined.

The results are summarized below in Table XXVII.

Run 5002

The procedure described in Run 5001 was followed except no excess alkyl aluminum compound was present in the reactor and the catalyst was derived using the procedure described in Run 3001, as follows.

0.21 g (0.601 mmol) of Cracac₃ was combined with 0.12 ml (1.73 mmol) of neat pyrrole and 15 ml of toluene. The resulting solution was stirred under dry nitrogen, at ambient temperature and pressure for 5 minutes. Then, 6.0 ml of a 1.9M (11.4 mmol) TEA solution in toluene was added. The resulting dark brown reaction mixture was stirred for 5 minutes under dry nitrogen, at ambient temperature and pressure. Then, 2.0 g of an aluminophosphate support (0.4 P/Al molar ratio, activated at 700° C.) prepared in accordance with U.S. Pat. No. 4,364,855 (1982), herein incorporated by reference, was added and the resulting slurry stirred for a period of approximately 12 hours. The product was collected by filtration, rinsed at least twice with 10 mL aliquots of toluene and pentane, until no color was observed in the filtrate and vacuum dried. the dried product was used as a solid, supported catalyst system.

A 0.28 g catalyst charge was used in the butadiene reaction. The results are summarized below in Table XXVII.

TABLE XXVII

| | | Butadiene Reaction | | |
|---|---|---|---|---|
| | % Butadiene | | | |
| | Conversion | Distribution of Products, Weight % | | |
| Run | to Products | 1,5-Cyclooctadiene | Other Liquids | Solid |
| 5001 | 97 | 91.9 | 0.3 | 7.8 |
| 5002 | 68 | 60.8 | 2.5 | 36.7 |

EXAMPLE XV

In the following Runs, all catalyst systems were prepared in a glove box, under dry nitrogen at ambient temperature and pressure. Transition metal compounds were weighed and combined with three (3) equivalents, (0.062) ml, pyrrole; 2 ml cyclohexane, as a solvent; and 6 ml of a 1.1M solution of triethylaluminum (TEA) in heptane. The resulting product was shaken for times varying from 5 minutes to 16 hours.

All runs were carried out in a 1 liter autoclave reactor containing 300 ml cyclohexane. 1.0 ml of the liquid catalyst systems were diluted in cyclohexane and were added to the reactor under a counter-flow of ethylene (CP grade). The reactor was sealed and ethylene addition stopped until the reactor temperature reached a reaction temperature of 80° C. The ethylene pressure was increased to a total reactor pressure of 550 psig. Ethylene was fed on demand for a 30 minute run time. If necessary, heat was applied to maintain a reactor temperature of 80° C.

At the end of each run, a sample of the liquid reaction product mixture was taken and analyzed via capillary gas chromatography, on a HP-5880 gas chromatograph equipped with an FID detector and a 60 meter DB-1 column, with a 0.25 mm ID and a 0.25M film. The gas chromatograph was ramped from 40° C. to 275° C. at a rate of 10° C./min, with a 20 minute hold time. Cyclohexane was used as an internal standard. The remaining reaction product mixture was evaporated and the amount of solid product produced was determined.

The results are given in Table XXVIII.

TABLE XXVIII

| Run | Metal Compound | Grams, Metal Compound | Catalyst System Appearance | Грамм Catalyst Charged | Activity, (g product/ g catalyst/ hr.) | Grams, total Prod. | Weight Percent Liquid | Weight Percent Solid | Liquid Product Distribution, Weight Percent | | | | |
|---|---|---|---|---|---|---|---|---|---|---|---|---|---|
| | | | | | | | | | $C_4=$ | $1C_6=$ | $C_6=$ | $C_8=$ | $C_{10}=$ |
| 6001 | Ni(acac)₂ | 0.075 | dark brown solution some solids | 0.0094 | 324 | 1.52 | 95.4 | 4.6 | 4 | 65 | 4 | 7 | 9 |
| 6002 | Ni(napth)₂ | 0.285 | dark brown solution | 0.356 | 8 | 0.14 | 29.5 | 70.5 | 74 | 0 | 0 | 4 | 0 |
| 6003 | Co(acac)₂ | 0.075 | brown | 0.0094 | 59 | 0.28 | 78.5 | 21.5 | 71 | 13 | 0 | 11 | 1 |

TABLE XXVIII-continued

| Run | Metal Compound | Grams, Metal Compound | Catalyst System Appearance | Grams Catalyst Charged | Activity, (g product/ g catalyst/ hr.) | Grams, total Prod. | Weight Percent Liquid | Weight Percent Solid | Liquid Product Distribution, Weight Percent | | | | |
|---|---|---|---|---|---|---|---|---|---|---|---|---|---|
| | | | | | | | | | $C_4=$ | $1C_6=$ | $C_6=$ | $C_8=$ | $C_{10}=$ |
| | | | solution, dark solid | | | | | | | | | | |
| 6004 | Mn(acac)$_2$ | 0.073 | brown-green solution | 0.0091 | 18 | 0.08 | 27.7 | 72.3 | 54 | 0 | 0 | 6 | 0 |
| 6005 | Mn(acac)$_2$ | 0.102 | brown solution | 0.0128 | 12 | 0.08 | 23.7 | 76.3 | 50 | 0 | 0 | 0 | 0 |
| 6006 | Cu(acac)$_2$ | 0.076 | dark green solution | 0.0095 | 97 | 0.46 | 89.2 | 10.8 | 5 | 0 | 0 | 0 | 0 |
| 6007 | MoO$_2$-(acac)$_2$ | 0.095 | green/ red solution some solid | 0.0119 | 16 | 0.10 | 47.7 | 52.3 | 41 | 0 | 0 | 34 | 5 |
| 6008 | TiO(acac)$_2$ | 0.075 | — | 0.0094 | 222 | 1.04 | 71.2 | 28.8 | 11 | 48 | 7 | 8 | 20 |
| 6009 | VO(acac)$_2$ | 0.077 | — | 0.0096 | 115 | 0.56 | 56.8 | 43.2 | 15 | 50 | 13 | 16 | 2 |
| 6010 | Zr(acac)$_2$ | 0.141 | — | 0.0176 | 29 | 0.26 | 26.8 | 73.2 | 0 | 27 | 0 | 44 | 4 |

The data in Table XXVIII show that other metal compounds can trimerize, oligomerize, and/or polymerize 1-olefins. Of these metal compounds, Ni(acac)$_2$, Run 6001, showed the best activity and selectivity toward trimerization.

EXAMPLE XVI

In the following Example, Runs 7001–7005 demonstrate the effect of hydrolyzing the metal alkyl prior to use and the effect of the presence and absence of a pyrrole-containing compound. Runs 7006–7009 compared to Runs 7010–7013 demonstrate the effect of preparation of a catalyst system in an unsaturated hydrocarbon.

Runs 7001–7005

In Runs 7001–7005, the molar ratio of elemental chromium to elemental aluminum to ligand (Cr:Al:L), the catalyst components added to the reactor are 1:30:10. In Runs 7001–7003, the chromium compound was Cr(EH)$_3$ and the chromium compound in Runs 7004 and 7005 was Cr(Py)$_3$. The aluminum compound was triisobutylaluminum (i-Al(Bu)$_3$) and was treated in the following manner. To an approximately ten percent, by weight, solution of triisobutylaluminum in heptane was added 1.0 mole equivalent of distilled water, steadily, but in one batch, while cooling the flask containing time solution with ice water to maintain a temperature of about 10° to about 20° C. The solution was stirred vigorously during and after water addition and continued until no further gas evolution was observed. The ligand was dimethoxyethane (DME).

Runs 7001–7005 were carried out in a 2 liter autoclave reactor. The chromium compound was dissolved in 400–500 ml anhydrous n-heptane and added to the reactor, under a dry nitrogen purge. Then the appropriate volume of a stirred, treated 0.31M solution of i-Al(Bu)$_3$ in heptane, as described above, was added. Then, the appropriate volume of DME was added, along with 5 ml of nonane (reactor internal standard). The reactor was sealed and brought to a temperature of 80° C. in Run 7001 and 95° C. in Runs 7002–7005 and a pressure of 550 psig with ethylene. Ethylene was fed on demand for a run time of 25 minutes in Run 7001, 30 minutes in Run 7002 and 45 minutes in Runs 7003–7005.

At the end of each run, a sample of the liquid reaction product mixture was taken and analyzed via capillary gas chromatography, on a HP-5800 gas chromatograph equipped with an FID detector and a 60 meter DB-1 column, with a 0.25 mm ID and a 0.25μ film. The gas chromatograph was ramped from 40° C. to 275° C. at a rate of 10° C./min, with a 20 minute hold time. The remaining reaction product mixture was evaporated and the amount of solid product produced was determined.

The catalyst systems used in Runs 7006–7013 were prepared according to the following procedures. Catalyst systems in Runs 7006–7009 were prepared in the presence of toluene, an unsaturated aromatic hydrocarbon. Catalyst systems in Runs 7010–7013 were prepared in the presence of 1-hexene, an unsaturated aliphatic hydrocarbon.

Run 7006

3.72 g of [Na(DME)$_2$] [CrCl(Py)$_3$DME] was combined with 50 ml toluene. Slowly, 26.4 ml of neat (93%) TEA was added and stirred for 30 minutes. The slurry turned dark brown. Excess solvent was removed by vacuum, resulting in a dark yellowish/brown oil and solid. About 70 ml cyclohexane was added. The resultant product was filtered and the filtrate was diluted to 200 ml with cyclohexane and 8.0 ml were charged to the reactor. The product contained 1.67 mg Cr/ml.

Run 7007

0.35 g of chromium(III) ethylhexonoate (CrEH$_3$) was combined with about 15 ml of toluene, forming a deep green solution. 0.22 ml of 2,5-dimethylpyrrole (2,5-DMP) and 0.20 ml of 1-bromobutane were added. Slowly, 5.7 ml of 1.9M TEA solution in toluene was added and stirred for 30 minutes to give a greenish, brown solution and a solid. Excess solvent was removed by vacuum and the liquid was extracted into about 15 ml cyclohexane. The resultant product was filtered and the filtrate was diluted to 25 ml with cyclohexane to form a golden colored solution, of which 7.0 ml were charged to the reactor. The product contained 0.014 g CrEH$_3$/ml.

Run 7008

The procedure described in Run 7007 was followed, except 0.22 g CrEH$_3$ and 0.13 ml of 2,5-DMP were used. Furthermore, 0.10 ml of GeCl$_4$ were substituted for the 1-bromobutane. 3.4 ml of 1.9M TEA solution in toluene was added to give a brown to brown/yellow solution and a precipitate. The final product after filtration and dilution to 25 ml with cyclohexane, was a bright gold-yellow color and contained 0.0088 g CrEH$_3$/ml. 3.0 ml were charged to the reactor.

Run 7009

2.070 g of CrPy$_3$Cl was added to 70 ml toluene and 62 ml of 1.9M TEA solution in toluene, mixed and filtered. The filtrate volume was reduced to about 20 ml by a dynamic vacuum. The viscous brown solution was filtered again. Then, about 30 ml of pentane was added to the filtrate. After about one day, the solution was vacuum stripped of excess solvent. Then 38.1 g of aluminophosphate (P/Al molar ratio of 0.9, activation at 700° C.), prepared in accordance with U.S. Pat. No. 4,364,855 were added. The slurry was stirred about 30 hours. The solid was collected by filtration and washed separately with toluene, cyclohexane and pentane. 0.4388 g of the solid catalyst system were charged to the reactor.

Run 7010

0.21 g of [Na(DME)$_2$][CrCl(Py)$_3$aDME] was combined with about 15 ml 1-hexene. Slowly, 0.75 ml of neat (93%) TEA was added, forming a brown solution and a sticky-looking precipitate, and stirred for 30 minutes. Excess solvent was removed by vacuum. The residue was extracted into about 15 ml cyclohexane, filtered and the filtrate was diluted to 25 ml with cyclohexane. 8.0 ml (0.067 g) were charged to the reactor.

Run 7011

The procedure described in Run 7010 was followed, except the final catalyst system, in cyclohexane, was aged for about 24 hours prior to use. 8.0 ml (0.067 g) were charged to the reactor.

Run 7012

0.26 g of CrEH$_3$ was dissolved in about 15 ml 1-hexene. 0.15 ml of 2,5-DMP and 0.13 ml of 1-bromobutane were added. Slowly, 1.0 ml of neat (93%) TEA was added and stirred for 30 minutes. Excess solvent was removed by vacuum and the liquid was extracted into about 15 ml cyclohexane. The resultant product was filtered and the filtrate was diluted to 25 ml with cyclohexane. 7.0 ml were charged to the reactor.

Run 7013

0.21 g [Na(DME)$_2$][CrCl(Py)$_3$DME] was combined with about 15 ml 1-hexene. Slowly, 1.0 ml of neat (93%) TEA was added, forming a dark brown solution and precipitate, and stirred for about 1 hour. The solution was decanted off and added to 1.5 g of aluminophosphate (P/Al molar ratio of 0.4, activation at 700° C.), prepared in accordance with U.S. 4,364,855, were added.

The supported catalyst system was collected by filtration, washed with 1-hexene and dried under a nitrogen purge. 0.6328 g of the solid catalyst system were charged to the reactor.

Runs 7006–7013 were carried out in a 1.2 liter autoclave reactor, containing cyclohexane. The heterogeneous, dried, supported catalyst systems (Runs 7009 and 7013) were slurried in cyclohexane to facilitate addition to the polymerization reactor, and were added to the polymerization reactor under a counter-flow of ethylene (CP grade). The homogeneous, liquid, unsupported catalyst systems (Runs 7006–7008 and 7010–7012) were diluted in cylcohexane and were added to the polymerization reactor under a counter-flow of ethylene (CP grade). The reactor was sealed and ethylene addition stopped until the reactor temperature reached a reaction temperature of 80° C. The ethylene pressure was increased to a total reactor pressure of 550 psig. Ethylene was then fed on demand for a 30 minute run time. At the end of the run, a sample of the liquid reaction product mixture was taken and analyzed via capillary gas chromatography, on a HP-5880 gas chromatograph equipped with a FID detector. The column was a 60 meter DB-1 column with a 0.25 mm ID and a 0.25p film. The gas chromatograph was ramped from 40° C. to 275° C. at a rate of 10° C./min, with a 20 minute hold time. The remaining reaction product mixture was evaporated and the amount of solid product produced was determined.

The results of the reactions are in Table XXIX, below.

TABLE XXIX

| Run | Catalyst System | mg Cr (elemental) Charged | Activity, g product/ g Cr/hr | Grams, Total Products | Weight Percent Liquid | Weight Percent Solid | Molar Ratios Cr/N/Al/L[a] | Liquid Product Distribution, Weight Percent | | | | |
|---|---|---|---|---|---|---|---|---|---|---|---|---|
| | | | | | | | | $C_4=$ | 1-$C_6=$ | $C_6=$ | $C_8=$ | $C_{10}=$ |
| 7001 | Cr(EH)$_3$, DME, i-Al(Bu)$_3$/ H$_2$O | 37.6 | 430 | 6.8 | 47 | 53 | 1/0/30/10 | 1 | 94 | <1 | 4 | <1 |
| 7002[b] | Cr(EH)$_3$, DME, i-Al(Bu)$_3$/ H$_2$O | 37.6 | 3,100 | 59.1 | 16 | 84 | 1/0/30/10 | 1 | 94 | 1 | 1 | 2 |
| 7003 | Cr(EH)$_3$, DME, i-Al(Bu)$_3$/ H$_2$O | 13.2 | 4,000 | 39.7 | 64 | 36 | 1/0/30/10 | 1 | 95 | <1 | 2 | 1 |
| 7004 | Cr(Py)$_3$[c] DME, i-Al(Bu)$_3$/ H$_2$O | 13.5 | 830 | 8.3 | 87 | 13 | 1/0/30/10 | 1 | 83 | 6 | 2 | 7 |
| 7005 | Cr(Py)$_3$[c] | 38.7 | 520 | 15.0 | 76 | 24 | 1/0/30/10 | 2 | 80 | 4 | 2 | 6 |

TABLE XXIX-continued

| Run | Catalyst System | mg Cr (elemental) Charged | Activity, g product/ g Cr/hr | Grams, Total Products | Weight Percent Liquid | Weight Percent Solid | Molar Ratios Cr/N/Al/L$^{(a)}$ | C$_4$= | 1-C$_6$= | C$_6$= | C$_8$= | C$_{10}$= |
|---|---|---|---|---|---|---|---|---|---|---|---|---|
| | DME, i-Al(Bu)$_3$/ H$_2$O | | | | | | | | | | | |
| 7006 | CrCl(Py)$_3$, DME, TEA | 13.5 | 7,800 | 52.6 | 99.4 | 0.6 | 1/3/30/0 | <1 | 82 | 10 | 1 | 7 |
| 7007 | Cr(EH)$_3$, 25 DMP, TEA, n-BuBr | 9.9 | 25,300 | 126.8 | 99.2 | 0.8 | 1/3/15/2.5 | <1 | 92 | 2 | <1 | 5 |
| 7008 | Cr(EH)$_3$, 25 DMP, TEA, GeCl$_4$ | 2.7 | 66,400 | 87.7 | 99.9 | 0.1 | 1/3/15/2.5 | <1 | 98 | <1 | <1 | <1 |
| 7009 | CrCl(Py)$_3$, DME, 0.9 P/Al | 0.397 g Catalyst | 69$^d$ | 14.0 | 97.1 | 2.9 | 1/3/30/0 | <1 | 87 | 7 | 1 | 3 |
| 7010 | CrCl(Py)$_3$, DME, TEA | 6 | 5,200 | 16.3 | 96.3 | 3.7 | 1/3/15/0 | 16 | 55 | 2 | 12 | 8 |
| 7011 | CrCl(Py)$_3$, DME, TEA | 6 | 5,070 | 15.9 | 96.2 | 3.8 | 1/3/15/0 | 15 | 55 | 2 | 12 | 8 |
| 7012 | Cr(EH)$_3$, 2,5 DMP, TEA, n-BuBr | 7.4 | 10,200 | 38.9 | 96.7 | 3.3 | 1/3/15/0 | 3 | 74 | 5 | 2 | 12 |
| 7013 | CrCl(Py)$_3$, DME, TEA, 0.4 P/Al | 0.6328 g Catalyst | 34$^d$ | 19.0 | 56.8 | 43.2 | 1/3/15/2.5 | 9 | 45 | 3 | 10 | 10 |

$^{a)}$N is nitrogen containing compound, i.e., pyrrole-containing compound; L is ligand.
$^{b)}$Reactor plugged with solids.
$^{c)}$CrCl(Py)$_3$ is equivalent to Cr(Py)$_3$, [Na(DME)$_2$] [CrCl(Py)$_3$DME].
$^{d)}$Activity is in units of g product/g catalyst/hr.

The data in Table XXIX shows that the presence of water (Runs 7001–7005) is detrimental to the formation of liquids, such as for example, 1-hexene. In fact, water in the reactor results in high solids formation.

Runs 7006–7013 show that catalyst systems prepared in the presence of any unsaturated hydrocarbon are effective toward trimerization. However, comparison of Runs 7006–7009, prepared in toluene, with Runs 7010–7013, prepared in 1-hexene, show that an unsaturated aromatic hydrocarbon is the preferred catalyst system preparation medium.

EXAMPLE XVIII

The following Example, Runs 8001–8017, demonstrates the effect of varying the pyrrole compound, halogen, and metal additive used.

Catalyst systems used in Runs 8001–8017 were all prepared in the same general procedure. In a typical preparation, chromium(III) 2-ethylhexanoate was dissolved in toluene. Next, 3 equivalents of 2,5-dimethylpyrrole (or hydrogen pyrrolide for Runs 8014–8017) was added to the solution. The desired amount of halide additive (2 to 3 molar equivalents) was then added, followed by 15 molar equivalents of triethylaluminum (TEA). The reaction mixture was stirred for 5–10 minutes and toluene was removed under vacuum. The liquid residue was diluted to a total volume of 10 ml with cyclohexane and an aliquot was charged to the reactor as the catalyst system.

The trimerization reaction runs were carried out in a 2-liter autoclave polymerization reactor containing 1.2 liters of 85% cyclohexane as the reactor diluent. Catalyst system was charged to the reactor followed by addition of cyclohexane. The reactor temperature was brought to 80° C. at which point ethylene was introduced. The pressure was maintained at 550 psig with ethylene fed on demand. Each reaction was run for 30 minutes before shutting off ethylene. Samples were taken at the end of the run and analyzed by gas chromatography, as described in other examples.

The results of the Runs and analyses are given in Table XXX.

TABLE XXX

| Run | Additive | mg Cr Charged | Molar Ratio Cr//Py/TEA/Add | Activity,$^a$ g liquid/g Cr/hour | Total Prod. Grams | Wt. % Liquid | Wt. % Solid | C$_4$= | 1-C$_6$= | C$_6$= | C$_8$= | C$_{10}$= |
|---|---|---|---|---|---|---|---|---|---|---|---|---|
| 8001 | None | 13.7 | 1/3/15/0 | 4700 | 33.7 | 95 | 5 | 30 | 43 | 6 | 5 | 13 |
| 8002 | DEAC | 14.2 | 1/3/15/3 | 16800 | 121.2 | 99 | 1 | <1 | 86 | 3 | 1 | 8 |
| 8003 | DEAB | 6.6 | 1/3/15/3 | 1800 | 61.5 | 98 | 2 | <1 | 93 | 2 | <1 | 4 |
| 8004 | DEAI-I | 13.7 | 1/3/15/3 | 630 | 5.0 | 86 | 14 | 4 | 72 | 8 | 2 | 12 |
| 8005 | n-BuCl | 6.8 | 1/3/15/3 | 6300 | 21.9 | 98 | 2 | 18 | 52 | 7 | 3 | 16 |
| 8006 | n-BuBr | 6.9 | 1/3/15/2.5 | 27500 | 95.0 | >99 | <1 | <1 | 91 | 2 | <1 | 5 |
| 8007 | n-BuBr | 9.9 | 1/3/15/2.5 | 25300 | 126.8 | >99 | <1 | <1 | 92 | 2 | <1 | 5 |
| 8008 | u-BuI | 6.1 | 1/3/15/3 | 2000 | 7.2 | 85 | 15 | 4 | 71 | 7 | 2 | 14 |
| 8009 | Me$_3$SiCl | 14.6 | 1/3/15/3 | 3600 | 26.9 | 97 | 3 | 16 | 57 | 6 | 4 | 14 |
| 8010 | Me$_3$SiBr | 6.6 | 1/3/15/3 | 14000 | 46.6 | >99 | <1 | <1 | 86 | 4 | <1 | 8 |
| 8011 | GeCl$_4$ | 6.6 | 1/3/15/2 | 55000 | 181.7 | >99 | <1 | <1 | 96 | <1 | <1 | 3 |

TABLE XXX-continued

| Run | Additive | mg Cr Charged | Molar Ratio Cr//Py/TEA/Add | Activity,[a] g liquid/g Cr/hour | Total Prod. Grams | Wt. % Liquid | Wt. % Solid | Liquid Product Distribution, Weight Percent | | | | |
|---|---|---|---|---|---|---|---|---|---|---|---|---|
| | | | | | | | | $C_4=$ | $1-C_6=$ | $C_6=$ | $C_8=$ | $C_{10}=$ |
| 8012 | $GeCl_4$ | 2.7 | 1/3/15/2 | 66400 | 87.7 | >99 | <1 | <1 | 98 | <1 | <1 | <1 |
| 8013 | $SnCl_4$ | 6.9 | 1/3/15/2 | 40600 | 140.4 | >99 | <1 | <1 | 96 | <1 | <1 | 2 |
| 8014 | DEAC | 10.8 | 1/3/15/2.5 | 6900 | 38.5 | 96 | 4 | <1 | 87 | 4 | 2 | 5 |
| 8015 | DEAB | 10.8 | 1/3/15/2.5 | 2600 | 14.3 | 97 | 3 | <1 | 89 | 3 | 2 | 4 |
| 8016 | DEAl-I | 10.8 | 1/3/15/2.5 | 70 | 0.4 | 44 | 56 | 19 | 60 | 6 | 3 | 4 |
| 8017 | $GeCl_4$ | 10.8 | 1/3/15/2.5 | 3300 | 19.0 | 94 | 6 | <1 | 95 | 2 | 1 | 2 |

[a]Based on grams liquid product only.

The data in Table XXX show that the selectivity towards 1-hexene increases in the order I<Cl<Br. The bromine-containing additives consistently have the highest selectivity for the formation of 1-hexene compared to the corresponding chloride or iodide additive. The increased production of 1-hexene also means that less byproducts ($C_4=$, $C_8=$, and $C_{10}=$) are being formed. The ratio of 1-hexene to internal hexenes also tends to increase in the order I<Cl<Br. Thus, the use of halides leads not only to more product, but a cleaner trimer product as well. The activity of the catalyst system increases in the order I<<Cl,Br. However, the activity between Br and Cl analogues appear to be unpredictable. For some additives ($SnX_4$, and $Al_3X_3SiX_4$) the Br is more active.

The data in Table XXX also show that the trend in selectivity to 1-hexene and activity can be extended to catalysts containing other pyrroles, as shown in Runs 8014–8017.

Overall, the best combination of activity and selectivity is obtained using $GeCl_4$ or $SnCl_4$ as the halide additives. However, it has been shown that the selectivity towards 1-hexene is also affected by the ratio of halide additive to triethylaluminum, making it possible to obtain high selectivity from other halide additives.

EXAMPLE XVIII

In the following Example, Runs 9001–9004 demonstrate that excess unsaturated aromatic hydrocarbon can be detrimental to trimerization and/or oligomerization. Thus, when a catalyst system is prepared in the presence of an aromatic hydrocarbon, such as, for example, toluene, removal of excess aromatic hydrocarbon is preferred. The resulting liquid is then extracted or dissolved into a desired solvent, such as, for example cyclohexane or heptane. While not wishing to be bound by theory, it is believed that an aromatic hydrocarbon can compete with a monomer to be trimerized and/or oligomerized, such as, for example, ethylene, for an active site of the catalyst system. Thus, it is believed that this competition can inhibit catalyst system activity.

The catalyst system used in Runs 9001–9004 was prepared using 1.35 g of chromium(III) 2-ethylhexanoate dissolved in toluene. Next, 0.86 mL (3.2 molar equivalents) of 2,5-dimethylpyrrole was added to the solution. Then 0.90 mL (3.2 molar equivalents) of n-butylbromide was added, followed by 7.60 mL (21 molar equivalents) of 93% triethylaluminum. The mixture mixture was stirred for 5–10 minutes and toluene was removed under vacuum. The liquid residue was dissolved into 30 mL of cyclohexane, filtered, and then diluted to a total volume of 50 mL with additional cyclohexane. Four (4) mL of this solution was charged along with the desired amount of anhydrous, degassed toluene (0, 5, 10 or 15 mL) to the reactor.

The trimerization reaction runs were carried out in a 2-liter autoclave polymerization reactor containing 1.2 liters of 85% cyclohexane as the reactor diluent. Catalyst system was charged to the reactor followed by addition of cyclohexane. The reactor temperature was brought to 80° C. at which point ethylene was introduced. The pressure was maintained at 550 psig with ethylene fed on demand. Each reaction was run for 30 minutes before shutting off ethylene. The total amount of ethylene consumed, i.e., fed, was measured.

The results of Runs 9001–9004 are given in Table XXXI.

TABLE XXXI

Effect of Aromatic Hydrocarbons on Catalyst System Activity

| Run | Toluene Added, ml | Toluene Added, Volume %[a] | Ethylene Consumed[b] After 30 mins, g |
|---|---|---|---|
| 9001 | 0 | 0.00 | 184 |
| 9002 | 5 | 0.42 | 160 |
| 9003 | 10 | 0.83 | 127 |
| 9004 | 15 | 1.25 | 109 |

[a]Based on total volume of reactor diluent.
[b]Not adjusted for solubility of ethylene in cyclohexane.

The data in Table XXXI show that the presence of an aromatic hydrocarbon, i.e., toluene, can result in a significant decrease in the activity of the catalyst system, as measured by ethylene consumption. This decrease is proportional to the amount of aromatic hydrocarbon added to the reactor.

EXAMPLE XIX

Ethylene-higher, alpha olefin copolymers were prepared in a continuous, particle form process by contacting ethylene with a polymerization catalyst system, prepared in accordance with U.S. Pat. No. 4,735,931, herein incorporated by reference, and a heterogeneous trimerization and/or oligomerization catalyst system. The trimerization/oligomerization catalyst system was prepared by combining in toluene 74 weight percent, based on the total weight of all components, of aluminophosphate (P/Al molar ratio of 0.9, activated at 700° C.), prepared in accordance with U.S. Pat. No. 4,364,855, herein incorporated by reference; 22 weight percent neat TEA; 4 weight percent ([Na(DME)$_2$][Cr-(Py)$_3$Cl(DME)]). The mixture was stirred for about 16 hours, filtered, and rinsed with aliquots of toluene and pentane until no color was observed in the filtrate. A light tan solid was recovered and used as the catalyst system. At all times, preparation of the resultant and trimerization/oligomerization catalyst system were done and kept under a dry, inert atmosphere at ambient temperature and pressure.

Copolymers were prepared by employing a full loop reactor, having a volume of 23 gallons (87 liters), with isobutane as a diluent. The reactor was operated to have a residence time of 1.25 hours. The reactor temperature was about 93° C. and pressure was about 540 psi. At steady state conditions, the isobutane feed rate was about 46 l/hr. The ethylene concentration in the reactor flash gas was between 9 and 10 mole percent, based on the contents of the flash gas, including diluent. The results of two Runs in a continuous, particle form, loop reactor are given in Table XXXII. Run 1101 was modified by the addition of dihydrogen ($H_2$) and TEA to the reactor. Run 1102 was modified by varying the trimerization catalyst system feed rates three times (Runs 1102a, 1102b, and 1102c), and thus the ratios of each catalyst system.

For comparative purposes, the trimerization and/or oligomerization catalyst system, alone, was contacted with ethylene. The trimerization run was carried out in a 2-liter autoclave polymerization reactor containing 1.2 liters of isobutane as the reactor diluent. Trimerization catalyst system was charged to the reactor followed by addition of isobutane. The reactor temperature was brought to 90° C. at which point ethylene was introduced. The pressure was maintained at 550 psig with ethylene fed on demand. The reaction was run for 30 minutes before shutting off ethylene. Samples were taken at the end of the run and analyzed by gas chromatography, as described in other examples.

Results of the trimerization Run are given in Table XXXIII.

TABLE XXXII

| Run | Weight Ratio Trimerization: Polymerization Catalysts | TEA Added to Reactor ppm[a] | $H_2$ in Flash Gas[b] | 1-$C_6$= in Flash Gas[b] | Polymer Density, g/cc[c] |
|---|---|---|---|---|---|
| 1101 | 0.85:1 | 1 | 1 | 0.45–0.5 | 0.948 |
| 1102a | 0.85:1 | None | None | 0.63 | 0.944 |
| 1102b | 1.28:1 | None | None | 0.8 | 0.939 |
| 1102c | 1.62:1 | None | None | 1.0 | 0.937 |

[a]Based on isobutane diluent feed
[b]Mole percent, based on contents of flash gas, including diluent
[c]Determined on a compression molded sample, cooled at about 15° C. per hour, and conditioned for about 40 hours at room temperature, in accordance with ASTM D1505 and ASTM D1928, condition C.

TABLE XXXIII

| | Weight Percent | Weight Percent | Liquid Product Distribution, Weight Percent | | | | | | |
|---|---|---|---|---|---|---|---|---|---|
| Run | Liquid | Solid | $C_4$= | 1-$C_6$= | $C_6$= | $C_8$= | $C_{10}$= | $C_{12}$= | $C_{14}$= |
| 1103 | 96 | 4 | 3 | 81 | 8 | 1 | 5 | <1 | <1 |

The data in Table XXXII show that a polymerization and trimerization catalyst systems can be used in the same reactor to generate comonomer(s) in-situ, and produce copolymers of ethylene and a higher, alpha olefin. Increasing the ratio of trimerization to polymerization catalyst system, :results in more 1-hexene production and, therefore, a lower polymer density.

EXAMPLE XX

All polymerization runs were carried out as described in Example VIII.

Density was determined in grams per cubic centimeter (g/cc) on a compression molded sample, cooled at about 15 C per hour, and conditioned for about 40 hours at room temperature in accordance with ASTM D1505 and ASTM D1928, condition C. The high load melt index (HLMI) was determined in accordance with ASTM D1238 at 190° C. with a 21,600 gram weight. Melt index (MI) was determined according to ASTM D1238 at 190° C. with a 2,160 gram weight.

Run 21: 0.100 g of Product V (prepared in the THF solvent), which was heated to 80° C. for 4 hours under nitrogen flush to remove residual THF, was slurried with 15 ml toluene at ambient temperature. 7.0 ml of a 1M TEA in hexanes solution was added and the solution stirred for 24 hours. The formation of a brown solution and the complete dissolution of Product V resulted immediately upon TEA addition. An $AlPO_3$ (P/Al mole ratio=0.4) (2.0 g) was added to the solution and stirred for 2 hours. The supported catalyst was filtered from the solution as a brown solid, rinsed twice with toluene, and then twice with pentane. 0.225 g of this catalyst was mixed with 0.89 g of a tergel-supported chromium catalyst as two free-flowing powders. The tergel-supported chromium catalyst was prepared in accordance with procedures in U.S. Pat. No. 3,887,494. 0.2576 g of this catalyst mixture was charged directly to the polymerization reactor. 3.0 ml of a 0.5% TEA in heptanes solution was charged to the reactor after the catalyst charge, but before the isobutane (reactor solvent) charge, to purge feedstock poisons. The reactor was pressurized to 550 psig with ethylene. After a 60.8 minute run time, 190 g of polymer was produced. The polymer had a MI=6.5, HLMI=366.2, and a density equal to 0.9132 g/cc. The catalyst activity was 730 g polymer/g catalyst/hr based on a 60.8 minute run time (run temperature 90° C., 550 psig total pressure).

Run 22: 0.100 g of Product V (prepared in the THF solvent), which was heated to 80° C. for 4 hours under nitrogen flush to remove residual THF, was slurried with 15 ml toluene at ambient temperature. 7.0 ml of a 1M TEA in hexanes solution was added and the solution stirred for 24 hours. The formation of a brown solution and the complete dissolution of Product V resulted immediately upon TEA addition. An $AlPO_3$ support (P/Al mole ratio=0.4) (2.0 g) was added to the solution and stirred for 2 hours. The supported catalyst was filtered from the solution as a brown solid, rinsed twice with toluene, and then twice with pentane. 0.2314 g of this catalyst was mixed with 0.0184 g of a titanium-containing catalyst as two free- flowing powders. The titanium-containing catalyst was prepared in accordance with procedures in U.S. Pat. Nos. 4,325,837 and U.S. Pat. No. 4,326,988 wherein ethylaluminumdichloride was the aluminum alkyl used. 0.2385 g of this catalyst mixture was charged directly to the polymerization reactor. 3.0 ml of a 0.5 percent TEA in heptanes solution was charged to the reactor after the catalyst charge, but before the isobutane (1 liter, to the reactor solvent) charge, to purge feedstock poisons. About 50 psig of dihydrogen ($H_2$) was then charged to the reactor, followed by pressurizing to 550 psig with ethylene. After a 31.0 minute run time, 82 g of polymer was produced. The polymer had a MI=0.011, HLMI=0.63, and a density equal to 0.9429 g/cc. The catalyst activity was 670 g polymer/g catalyst/hr based on a 31.0 run time (run temp. 90° C., 550 psig total pressure).

While this invention has been described in detail for the purpose of illustration, it is not to be construed as limited thereby but is intended to cover all changes and modifications within the spirit and scope thereof.

That which is claimed is:

1. A process comprising polymerizing olefins in the presence of a polymerization catalyst system and a trimerization cocatalyst system
   wherein said cocatalyst system is prepared by a process comprising forming a mixture of:
   (a) a metal source wherein said metal source is selected from the group consisting of chromium, nickel, cobalt, iron, molybdenum, and copper compounds;
   (b) a pyrrole-containing compound;
   (c) a non-hydrolyzed aluminum alkyl; and
   (d) an unsaturated hydrocarbon and wherein the weight ratio of the trimerization catalyst system to the polymerization catalyst system is sufficient to produce a polyolefin having a density of less than about 0.948 g/cc.

2. A process according to claim 1 wherein said cocatalyst system further comprises a support.

3. A process according to claim 1 wherein said metal source is a chromium source.

4. A process according to claim 1 wherein said pyrrole-containing compound is selected from the group consisting of hydrogen pyrrolide and 2,5-dimethylpyrrolide.

5. A process according to claim 1 wherein said non-hydrolyzed aluminum alkyl is a trialkyl aluminum compound.

6. A process according to claim 5 wherein said trialkyl aluminum compound is triethyl aluminum.

7. A process according to claim 1 wherein said unsaturated hydrocarbon is selected from the group consisting of aromatic and aliphatic hydrocarbons having less than about 70 carbon atoms per molecule.

8. A process according to claim 7 wherein said unsaturated hydrocarbon is an aromatic hydrocarbon having less than about 20 carbon atoms per molecule.

9. A process according to claim 8 wherein said aromatic unsaturated hydrocarbon is selected from the group consisting of toluene, benzene, xylene, mesitylene, and hexamethylbenzene.

10. A process according to claim 7 wherein said unsaturated hydrocarbon is selected from the group consisting of toluene, ethylene, and mixtures thereof.

11. A process according to claim 2 wherein said cocatalyst support is selected from the group consisting of zeolites and inorganic oxides.

12. A process according to claim 1 further wherein said cocatalyst system further comprises a halide selected from the group consisting of fluoride, chloride, bromide, iodide, and mixtures-thereof.

13. A process according to claim 12 wherein said halide is selected from the group consisting of chloride, bromide, and mixtures thereof.

14. A process according to claim 12 wherein said halide is provided by a compound having a formula of $R_mX_n$, wherein R can be any organic or inorganic radical, X can be a halide, and m+n can be any number greater than 0.

15. A process according to claim 14 wherein R is an inorganic radical selected from the group consisting of aluminum, silicon, germanium, hydrogen, boron, lithium, tin, gallium, indium, lead, and mixtures thereof.

16. A process according to claim 15 wherein R is selected from the group consisting of aluminum, tin, germanium, and mixtures thereof.

17. A process according to claim 1 wherein said cocatalyst system comprises:
    (a) about 1 mole of metal;
    (b) about 1 to 15 moles of pyrrole-containing compound;
    (c) about 5 to about 40 moles of non-hydrolyzed aluminum alkyl; and
    (d) an unsaturated hydrocarbon.

18. A composition according to 17 further comprising about 1 to about 30 moles of halide.

19. A process according to claim 1 wherein said cocatalyst system is prepared according to a process combining a metal source, a pyrrole-containing compound, a non-hydrolyzed aluminum alkyl, and an unsaturated hydrocarbon, under time, temperature, and pressure sufficient to form a catalyst system.

20. A process according to claim 19 wherein said cocatalyst preparation is carried out in the absence of oxygen and water.

21. A process according to claim 19 wherein said metal source and said pyrrole-containing compound are combined prior to the addition of said non-hydrolyzed aluminum.

22. A process according to claim 19 further comprising the addition of a halide source to said cocatalyst system.

23. A process according to claim 22 wherein said halide source is selected from the group consisting of chloride, bromide, and mixtures thereof.

24. A process according to claim 22 wherein:
    said metal source is a chromium-containing compound,
    said pyrrole-containing compound is selected from the group consisting of hydrogen pyrrolide, 2,5-dimethylpyrrolide, and mixtures thereof;
    said non-hydrolyzed aluminum alkyl is triethylaluminum;
    said unsaturated hydrocarbon compound is toluene; and
    said halide source is ethylaluminum dichloride.

25. A process according to claim 1 wherein said olefin is selected from the group consisting of compounds having from about 2 to about 30 carbon atoms per molecule and at least 1 olefinic double bond.

26. A process according to claim 25 wherein said olefin compound is selected from the group consisting of ethylene, 1-butene, 1-hexene, 1,3-butadiene, and mixtures thereof.

27. A process according to claim 26 wherein said olefin is ethylene.

28. A process according to claim 19 wherein:
    said metal source is a chromium-containing compound,
    said pyrrole-containing compound is selected from the group consisting of hydrogen pyrrolide, 2,5-dimethylpyrrolide, and mixtures thereof;
    said non-hydrolyzed aluminum alkyl is triethylaluminum;
    said unsaturated hydrocarbon compound is toluene; and
    said halide source is ethylaluminum dichloride.

29. A process according to claim 1 wherein said metal source and said pyrrole-containing compound are a chromium pyrrolide.

* * * * *